(12) United States Patent
Lock et al.

(10) Patent No.: US 9,970,942 B2
(45) Date of Patent: May 15, 2018

(54) SYSTEM AND METHOD FOR THE DETECTION OF ALLERGENS

(75) Inventors: Stephen J. Lock, West Yorkshire (GB); Subhasish Purkayastha, Acton, MA (US); Brian L. Williamson, Ashland, MA (US); Keling Dong, Westborough, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 518 days.

(21) Appl. No.: 14/342,079

(22) PCT Filed: Sep. 4, 2012

(86) PCT No.: PCT/US2012/053689
§ 371 (c)(1),
(2), (4) Date: Sep. 30, 2014

(87) PCT Pub. No.: WO2013/033713
PCT Pub. Date: Mar. 7, 2013

(65) Prior Publication Data
US 2016/0025741 A1    Jan. 28, 2016

Related U.S. Application Data

(60) Provisional application No. 61/530,612, filed on Sep. 2, 2011.

(51) Int. Cl.
| | | |
|---|---|---|
| *A61K 39/00* | (2006.01) |
| *A61K 39/35* | (2006.01) |
| *A61K 39/36* | (2006.01) |
| *C12Q 1/00* | (2006.01) |
| *C12Q 1/40* | (2006.01) |
| *G01N 33/00* | (2006.01) |
| *G01N 24/00* | (2006.01) |
| *G01N 1/00* | (2006.01) |
| *G01N 33/68* | (2006.01) |
| *G01N 30/72* | (2006.01) |
| *G01N 30/88* | (2006.01) |

(52) U.S. Cl.
CPC ..... *G01N 33/6848* (2013.01); *G01N 30/7233* (2013.01); *G01N 2030/8831* (2013.01); *G01N 2333/415* (2013.01); *G01N 2333/4713* (2013.01); *G01N 2333/4731* (2013.01); *G01N 2333/77* (2013.01); *G01N 2333/976* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 7,112,784 B2 | 9/2006 | Bateman et al. | |
| 7,901,942 B2 | 3/2011 | Kamiie et al. | |
| 2009/0197345 A1* | 8/2009 | Seppala | G01N 33/6848 436/89 |

FOREIGN PATENT DOCUMENTS

| | | |
|---|---|---|
| WO | 2007/031080 | 3/2007 |
| WO | 2010/119261 | 10/2010 |

OTHER PUBLICATIONS http://allergen.org/viewallergen.php?aid=166.*
http://allergen.org/viewallergen.php?aid=163.*
International Search Report from International Patent Application No. PCT/US2012/053689, dated Feb. 13, 2013.
Heick J et al. "First screening method for the simultaneous detection of seven allergens by liquid chromatography mass spectrometry", Journal of Chromatography A, Elsevier Science Publishers B.V., NL, vol. 1218 No. 7, Dec. 15, 2010 pp. 938-943.
Parisa Ansari et al. "Selection of possible marker peptides for the detection of major ruminant milk proteins in food by liquid chromatography-tandem mass spectrometry", Analytical and Bioanalytical Chemistry, vol. 399, No. 3, Nov. 2010, pp. 1105-1115.
Linda Monaci et al. "Feasibility of a capillary LC/ESI-Q-TOF MS method for the detection of milk allergens in an incurred model food matrix", Analytical Methods, vol. 2, No. 7, Jan. 2010, pp. 967-972.
Dorcas Weber et al. "Development of a Liquid Chromatography-Tandem Mass Spectrometry Method Using Capillary Liquid Chromatography and Nanoelectrospray Ionization-Quadrupole Time-of-Flight Hybrid Mass Spectrometer for the Detection of Milk Allergens", Journal of Agricultural and Food Chemistry, vol. 54, No. 5 Mar. 2006 pp. 1604-1610.

* cited by examiner

*Primary Examiner* — Nora Rooney

(57) ABSTRACT

Methods and systems for detecting allergens using mass spectrometry are provided herein. In some aspects, a sample can be screened for the presence or quantity of ovalbumin, lysozyme, casein (isoform S1 and S2), lactoglobulin, high and low glutens, wheat, rye, oats, barley, mustard, sesame, and various types of nuts including macadamia, pistachio, brazil, walnuts, peanuts and hazelnuts by detecting one or more peptides specific to the allergen of interest using selected MRM transitions.

6 Claims, 7 Drawing Sheets

SEQUENCE LISTING

<160> NUMBER OF SEQ ID NOS: 212

<210> SEQ ID NO 1
<211> LENGTH: 6
<212> TYPE: PRT
<213> ORGANISM: Gallus gallus

<400> SEQUENCE: 1

Leu Tyr Ala Glu Glu Arg
1               5

<210> SEQ ID NO 2
<211> LENGTH: 12
<212> TYPE: PRT
<213> ORGANISM: Gallus gallus

<400> SEQUENCE: 2

Tyr Pro Ile Leu Pro Glu Tyr Leu Gln Cys Val Lys
1               5                   10

<210> SEQ ID NO 3
<211> LENGTH: 10
<212> TYPE: PRT
<213> ORGANISM: Gallus gallus

<400> SEQUENCE: 3

Asp Glu Asp Thr Gln Ala Met Pro Phe Arg
1               5                   10

<210> SEQ ID NO 4
<211> LENGTH: 12
<212> TYPE: PRT
<213> ORGANISM: Gallus gallus

<400> SEQUENCE: 4

His Ile Ala Thr Asn Ala Val Leu Phe Phe Gly Arg
1               5                   10

<210> SEQ ID NO 5
<211> LENGTH: 13
<212> TYPE: PRT
<213> ORGANISM: Gallus gallus

<400> SEQUENCE: 5

Leu Thr Glu Trp Thr Ser Ser Asn Val Met Glu Glu Arg
1               5                   10

<210> SEQ ID NO 6
<211> LENGTH: 16
<212> TYPE: PRT
<213> ORGANISM: Gallus gallus

<400> SEQUENCE: 6

Gly Gly Leu Glu Pro Ile Asn Phe Gln Thr Ala Ala Asp Gln Ala Arg
1               5                   10                  15

<210> SEQ ID NO 7
<211> LENGTH: 16
<212> TYPE: PRT
<213> ORGANISM: Gallus gallus

<400> SEQUENCE: 7

Glu Leu Ile Asn Ser Trp Val Glu Ser Gln Thr Asn Gly Ile Ile Arg
1               5                   10                  15

-continued

<210> SEQ ID NO 8
<211> LENGTH: 7
<212> TYPE: PRT
<213> ORGANISM: Gallus gallus

<400> SEQUENCE: 8

His Gly Leu Asp Asn Tyr Arg
1               5

<210> SEQ ID NO 9
<211> LENGTH: 7
<212> TYPE: PRT
<213> ORGANISM: Gallus gallus

<400> SEQUENCE: 9

Trp Trp Cys Asn Asp Gly Arg
1               5

<210> SEQ ID NO 10
<211> LENGTH: 12
<212> TYPE: PRT
<213> ORGANISM: Gallus gallus

<400> SEQUENCE: 10

Phe Glu Ser Asn Phe Asn Thr Gln Ala Thr Asn Arg
1               5                   10

<210> SEQ ID NO 11
<211> LENGTH: 16
<212> TYPE: PRT
<213> ORGANISM: Gallus gallus

<400> SEQUENCE: 11

Asn Thr Asp Gly Ser Thr Asp Tyr Gly Ile Leu Gln Ile Asn Ser Arg
1               5                   10                  15

<210> SEQ ID NO 12
<211> LENGTH: 12
<212> TYPE: PRT
<213> ORGANISM: Bos taurus

<400> SEQUENCE: 12

Phe Phe Val Ala Pro Phe Pro Glu Val Phe Gly Lys
1               5                   10

<210> SEQ ID NO 13
<211> LENGTH: 16
<212> TYPE: PRT
<213> ORGANISM: Bos taurus

<400> SEQUENCE: 13

Leu Leu Ile Leu Thr Cys Leu Val Ala Val Ala Leu Ala Arg Pro Lys
1               5                   10                  15

<210> SEQ ID NO 14
<211> LENGTH: 7
<212> TYPE: PRT
<213> ORGANISM: Bos taurus

<400> SEQUENCE: 14

Glu Asp Val Pro Ser Glu Arg
1               5

<210> SEQ ID NO 15

```
<211> LENGTH: 10
<212> TYPE: PRT
<213> ORGANISM: Bos taurus

<400> SEQUENCE: 15

Tyr Leu Gly Tyr Leu Glu Gln Leu Leu Arg
1               5                   10

<210> SEQ ID NO 16
<211> LENGTH: 15
<212> TYPE: PRT
<213> ORGANISM: Bos taurus

<400> SEQUENCE: 16

His Gln Gly Leu Pro Gln Glu Val Leu Asn Glu Asn Leu Leu Arg
1               5                   10                  15

<210> SEQ ID NO 17
<211> LENGTH: 6
<212> TYPE: PRT
<213> ORGANISM: Bos taurus

<400> SEQUENCE: 17

Val Asn Glu Leu Ser Lys
1               5

<210> SEQ ID NO 18
<211> LENGTH: 7
<212> TYPE: PRT
<213> ORGANISM: Bos taurus

<400> SEQUENCE: 18

Glu Asp Val Pro Ser Glu Arg
1               5

<210> SEQ ID NO 19
<211> LENGTH: 6
<212> TYPE: PRT
<213> ORGANISM: Bos taurus

<400> SEQUENCE: 19

Val Ile Pro Tyr Val Arg
1               5

<210> SEQ ID NO 20
<211> LENGTH: 11
<212> TYPE: PRT
<213> ORGANISM: Bos taurus

<400> SEQUENCE: 20

Asn Ala Val Pro Ile Thr Pro Thr Leu Asn Arg
1               5                   10

<210> SEQ ID NO 21
<211> LENGTH: 8
<212> TYPE: PRT
<213> ORGANISM: Bos taurus

<400> SEQUENCE: 21

Asn Met Ala Ile Asn Pro Ser Lys
1               5

<210> SEQ ID NO 22
<211> LENGTH: 8
<212> TYPE: PRT
```

-continued

<213> ORGANISM: Bos taurus

<400> SEQUENCE: 22

Phe Ala Leu Pro Gln Tyr Leu Lys
1               5

<210> SEQ ID NO 23
<211> LENGTH: 12
<212> TYPE: PRT
<213> ORGANISM: Bos taurus

<400> SEQUENCE: 23

Thr Val Asp Met Glu Ser Thr Glu Val Phe Thr Lys
1               5                   10

<210> SEQ ID NO 24
<211> LENGTH: 9
<212> TYPE: PRT
<213> ORGANISM: Bos taurus

<400> SEQUENCE: 24

Val Leu Val Leu Asp Thr Asp Tyr Lys
1               5

<210> SEQ ID NO 25
<211> LENGTH: 8
<212> TYPE: PRT
<213> ORGANISM: Bos taurus

<400> SEQUENCE: 25

Ile Asp Ala Leu Asn Glu Asn Lys
1               5

<210> SEQ ID NO 26
<211> LENGTH: 20
<212> TYPE: PRT
<213> ORGANISM: Bos taurus

<400> SEQUENCE: 26

Val Tyr Val Glu Glu Leu Lys Pro Thr Pro Glu Gly Asp Leu Glu Ile
1               5                   10                  15

Leu Leu Gln Lys
            20

<210> SEQ ID NO 27
<211> LENGTH: 11
<212> TYPE: PRT
<213> ORGANISM: Bos taurus

<400> SEQUENCE: 27

Thr Pro Glu Val Asp Asp Glu Ala Leu Glu Lys
1               5                   10

<210> SEQ ID NO 28
<211> LENGTH: 9
<212> TYPE: PRT
<213> ORGANISM: Bos taurus

<400> SEQUENCE: 28

Trp Glu Asn Gly Glu Cys Ala Gln Lys
1               5

<210> SEQ ID NO 29
<211> LENGTH: 7

```
<212> TYPE: PRT
<213> ORGANISM: Bos taurus

<400> SEQUENCE: 29

Ala Leu Pro Met His Ile Arg
1               5

<210> SEQ ID NO 30
<211> LENGTH: 14
<212> TYPE: PRT
<213> ORGANISM: Unknown
<220> FEATURE:
<223> OTHER INFORMATION: Obtained from Hordeum vulgare

<400> SEQUENCE: 30

Thr Leu Pro Met Met Cys Ser Val Asn Val Pro Leu Tyr Arg
1               5                   10

<210> SEQ ID NO 31
<211> LENGTH: 8
<212> TYPE: PRT
<213> ORGANISM: Unknown
<220> FEATURE:
<223> OTHER INFORMATION: Obtained from Hordeum vulgare

<400> SEQUENCE: 31

Gly Val Gly Pro Ser Val Gly Val
1               5

<210> SEQ ID NO 32
<211> LENGTH: 14
<212> TYPE: PRT
<213> ORGANISM: Unknown
<220> FEATURE:
<223> OTHER INFORMATION: Obtained from Hordeum vulgare

<400> SEQUENCE: 32

Thr Leu Pro Thr Met Cys Ser Val Asn Val Pro Leu Tyr Arg
1               5                   10

<210> SEQ ID NO 33
<211> LENGTH: 16
<212> TYPE: PRT
<213> ORGANISM: Unknown
<220> FEATURE:
<223> OTHER INFORMATION: Obtained from Hordeum vulgare

<400> SEQUENCE: 33

Asn Thr Asp Gly Ser Thr Asp Tyr Gly Ile Leu Gln Ile Asn Ser Arg
1               5                   10                  15

<210> SEQ ID NO 34
<211> LENGTH: 7
<212> TYPE: PRT
<213> ORGANISM: Unknown
<220> FEATURE:
<223> OTHER INFORMATION: Obtained from genus Triticum species

<400> SEQUENCE: 34

Ser Asp Cys Gln Val Met Arg
1               5

<210> SEQ ID NO 35
<211> LENGTH: 13
<212> TYPE: PRT
<213> ORGANISM: Unknown
<220> FEATURE:
```

-continued

```
<223> OTHER INFORMATION: Obtained from genus Triticum species

<400> SEQUENCE: 35

Ala Pro Phe Ala Ser Ile Val Ala Ser Ile Gly Gly Gln
1               5                   10

<210> SEQ ID NO 36
<211> LENGTH: 23
<212> TYPE: PRT
<213> ORGANISM: Unknown
<220> FEATURE:
<223> OTHER INFORMATION: Obtained from genus Triticum species

<400> SEQUENCE: 36

Ser Leu Val Leu Gln Thr Leu Pro Thr Met Cys Asn Val Tyr Val Pro
1               5                   10                  15

Pro Tyr Cys Ser Thr Ile Arg
            20

<210> SEQ ID NO 37
<211> LENGTH: 23
<212> TYPE: PRT
<213> ORGANISM: Unknown
<220> FEATURE:
<223> OTHER INFORMATION: Obtained from genus Triticum species

<400> SEQUENCE: 37

Ser Leu Val Leu Gln Thr Leu Pro Thr Met Cys Asn Val Tyr Val Pro
1               5                   10                  15

Pro Tyr Cys Ser Thr Ile Arg
            20

<210> SEQ ID NO 38
<211> LENGTH: 33
<212> TYPE: PRT
<213> ORGANISM: Unknown
<220> FEATURE:
<223> OTHER INFORMATION: Obtained from genus Triticum species

<400> SEQUENCE: 38

Gln Pro Phe Pro Gln Gln Pro Gln Gln Pro Tyr Pro Gln Gln Pro Gln
1               5                   10                  15

Gln Pro Phe Pro Gln Thr Gln Gln Pro Gln Gln Pro Phe Pro Gln Ser
            20                  25                  30

Lys

<210> SEQ ID NO 39
<211> LENGTH: 7
<212> TYPE: PRT
<213> ORGANISM: Unknown
<220> FEATURE:
<223> OTHER INFORMATION: Obtained from genus Triticum species

<400> SEQUENCE: 39

Val Ser Ile Ile Leu Pro Arg
1               5

<210> SEQ ID NO 40
<211> LENGTH: 15
<212> TYPE: PRT
<213> ORGANISM: Unknown
<220> FEATURE:
<223> OTHER INFORMATION: Obtained from genus Triticum species

<400> SEQUENCE: 40
```

-continued

```
Gly Ile Ile Gln Pro Gln Gln Pro Ala Gln Leu Glu Gly Ile Arg
1               5                   10                  15

<210> SEQ ID NO 41
<211> LENGTH: 19
<212> TYPE: PRT
<213> ORGANISM: Unknown
<220> FEATURE:
<223> OTHER INFORMATION: Obtained from genus Triticum species

<400> SEQUENCE: 41

Ala Gln Gly Leu Gly Ile Ile Gln Pro Gln Gln Pro Ala Gln Leu Glu
1               5                   10                  15

Gly Ile Arg

<210> SEQ ID NO 42
<211> LENGTH: 23
<212> TYPE: PRT
<213> ORGANISM: Unknown
<220> FEATURE:
<223> OTHER INFORMATION: Obtained from genus Triticum species

<400> SEQUENCE: 42

Asn Phe Leu Leu Gln Gln Cys Asn His Val Ser Leu Val Ser Ser Leu
1               5                   10                  15

Val Ser Ile Ile Leu Pro Arg
            20

<210> SEQ ID NO 43
<211> LENGTH: 26
<212> TYPE: PRT
<213> ORGANISM: Unknown
<220> FEATURE:
<223> OTHER INFORMATION: Obtained from genus Triticum species

<400> SEQUENCE: 43

Pro Ser Gly Gln Val Gln Trp Pro Gln Gln Pro Phe Pro Gln Pro
1               5                   10                  15

Gln Gln Pro Phe Cys Gln Gln Pro Gln Arg
            20                  25

<210> SEQ ID NO 44
<211> LENGTH: 7
<212> TYPE: PRT
<213> ORGANISM: Unknown
<220> FEATURE:
<223> OTHER INFORMATION: Obtained from genus Triticum species

<400> SEQUENCE: 44

Val Asn Val Pro Leu Tyr Arg
1               5

<210> SEQ ID NO 45
<211> LENGTH: 10
<212> TYPE: PRT
<213> ORGANISM: Unknown
<220> FEATURE:
<223> OTHER INFORMATION: Obtained from genus Triticum species

<400> SEQUENCE: 45

Leu Glu Val Met Thr Ser Ile Ala Leu Arg
1               5                   10

<210> SEQ ID NO 46
```

-continued

```
<211> LENGTH: 14
<212> TYPE: PRT
<213> ORGANISM: Unknown
<220> FEATURE:
<223> OTHER INFORMATION: Obtained from genus Triticum species

<400> SEQUENCE: 46

Thr Thr Thr Ser Val Pro Phe Gly Val Gly Thr Gly Val Gly
1               5                   10

<210> SEQ ID NO 47
<211> LENGTH: 15
<212> TYPE: PRT
<213> ORGANISM: Unknown
<220> FEATURE:
<223> OTHER INFORMATION: Obtained from genus Triticum species

<400> SEQUENCE: 47

Thr Thr Thr Ser Val Pro Phe Gly Val Gly Thr Gly Val Gly Ala
1               5                   10                  15

<210> SEQ ID NO 48
<211> LENGTH: 16
<212> TYPE: PRT
<213> ORGANISM: Unknown
<220> FEATURE:
<223> OTHER INFORMATION: Obtained from genus Triticum species

<400> SEQUENCE: 48

Thr Thr Thr Ser Val Pro Phe Gly Val Gly Thr Gly Val Gly Ala Tyr
1               5                   10                  15

<210> SEQ ID NO 49
<211> LENGTH: 14
<212> TYPE: PRT
<213> ORGANISM: Unknown
<220> FEATURE:
<223> OTHER INFORMATION: Obtained from genus Triticum species

<400> SEQUENCE: 49

Ile Leu Pro Thr Met Cys Ser Val Asn Val Pro Leu Tyr Arg
1               5                   10

<210> SEQ ID NO 50
<211> LENGTH: 28
<212> TYPE: PRT
<213> ORGANISM: Unknown
<220> FEATURE:
<223> OTHER INFORMATION: Obtained from genus Triticum species

<400> SEQUENCE: 50

Ser Gln Met Leu Gln Gln Ser Ser Cys His Val Met Gln Gln Gln Cys
1               5                   10                  15

Cys Gln Gln Leu Pro Gln Ile Pro Gln Gln Ser Arg
            20                  25

<210> SEQ ID NO 51
<211> LENGTH: 33
<212> TYPE: PRT
<213> ORGANISM: Unknown
<220> FEATURE:
<223> OTHER INFORMATION: Obtained from genus Triticum species

<400> SEQUENCE: 51

Ser Gln Met Leu Gln Gln Ser Ser Cys His Val Met Gln Gln Gln Cys
1               5                   10                  15
```

-continued

Cys Gln Gln Leu Pro Gln Ile Pro Gln Ser Arg Tyr Glu Ala Ile
            20                  25                  30
Arg

<210> SEQ ID NO 52
<211> LENGTH: 13
<212> TYPE: PRT
<213> ORGANISM: Unknown
<220> FEATURE:
<223> OTHER INFORMATION: Obtained from genus Triticum species

<400> SEQUENCE: 52

Ala Pro Phe Ala Ser Ile Val Ala Gly Ile Gly Gly Gln
1               5                   10

<210> SEQ ID NO 53
<211> LENGTH: 13
<212> TYPE: PRT
<213> ORGANISM: Unknown
<220> FEATURE:
<223> OTHER INFORMATION: Obtained from genus Triticum species

<400> SEQUENCE: 53

Ala Pro Phe Ala Ser Ile Val Ala Gly Ile Gly Gly Gln
1               5                   10

<210> SEQ ID NO 54
<211> LENGTH: 14
<212> TYPE: PRT
<213> ORGANISM: Unknown
<220> FEATURE:
<223> OTHER INFORMATION: Obtained from genus Triticum species

<400> SEQUENCE: 54

Arg Ala Pro Phe Ala Ser Ile Val Ala Gly Ile Gly Gly Gln
1               5                   10

<210> SEQ ID NO 55
<211> LENGTH: 23
<212> TYPE: PRT
<213> ORGANISM: Unknown
<220> FEATURE:
<223> OTHER INFORMATION: Obtained from genus Triticum species

<400> SEQUENCE: 55

Ser Leu Val Leu Gln Thr Leu Pro Ser Met Cys Asn Val Tyr Val Pro
1               5                   10                  15

Pro Glu Cys Ser Ile Met Arg
            20

<210> SEQ ID NO 56
<211> LENGTH: 28
<212> TYPE: PRT
<213> ORGANISM: Unknown
<220> FEATURE:
<223> OTHER INFORMATION: Obtained from genus Triticum species

<400> SEQUENCE: 56

Gln Gln Pro Phe Pro Gln Thr Gln Gln Pro Gln Gln Pro Phe Pro Gln
1               5                   10                  15

Gln Pro Gln Gln Pro Phe Pro Gln Thr Gln Gln Pro
            20                  25

<210> SEQ ID NO 57
<211> LENGTH: 12

```
<212> TYPE: PRT
<213> ORGANISM: Unknown
<220> FEATURE:
<223> OTHER INFORMATION: Obtained from genus Tritic

```
<211> LENGTH: 10
<212> TYPE: PRT
<213> ORGANISM: Unknown
<220> FEATURE:
<223> OTHER INFORMATION: Obtained from genus Triticum species

<400> SEQUENCE: 63

Ile Phe Trp Gly Ile Pro Ala Leu Leu Lys
1               5                   10

<210> SEQ ID NO 64
<211> LENGTH: 11
<212> TYPE: PRT
<213> ORGANISM: Unknown
<220> FEATURE:
<223> OTHER INFORMATION: Obtained from genus Triticum species

<400> SEQUENCE: 64

Ile Phe Trp Gly Ile Pro Ala Leu Leu Lys Arg
1               5                   10

<210> SEQ ID NO 65
<211> LENGTH: 11
<212> TYPE: PRT
<213> ORGANISM: Unknown
<220> FEATURE:
<223> OTHER INFORMATION: Obtained from genus Triticum species

<400> SEQUENCE: 65

Gly Glu Ala Ser Glu Gln Leu Gln Cys Glu Arg
1               5                   10

<210> SEQ ID NO 66
<211> LENGTH: 11
<212> TYPE: PRT
<213> ORGANISM: Unknown
<220> FEATURE:
<223> OTHER INFORMATION: Obtained from genus Triticum species

<400> SEQUENCE: 66

Ile Phe Trp Gly Ile Pro Ala Leu Leu Lys Arg
1               5                   10

<210> SEQ ID NO 67
<211> LENGTH: 12
<212> TYPE: PRT
<213> ORGANISM: Unknown
<220> FEATURE:
<223> OTHER INFORMATION: Obtained from genus Triticum species

<400> SEQUENCE: 67

Glu Gly Glu Ala Ser Glu Gln Leu Gln Cys Glu Arg
1               5                   10

<210> SEQ ID NO 68
<211> LENGTH: 13
<212> TYPE: PRT
<213> ORGANISM: Unknown
<220> FEATURE:
<223> OTHER INFORMATION: Obtained from genus Triticum species

<400> SEQUENCE: 68

Ala Gln Gln Leu Ala Ala Gln Leu Pro Ala Met Cys Arg
1               5                   10

<210> SEQ ID NO 69
<211> LENGTH: 9
```

```
<212> TYPE: PRT
<213> ORGANISM: Unknown
<220> FEATURE:
<223> OTHER INFORMATION: Obtained from genus Triticum species

<400> SEQUENCE: 69

Ser Val Ala Val Ser Gln Val Ala Arg
1               5

<210> SEQ ID NO 70
<211> LENGTH: 10
<212> TYPE: PRT
<213> ORGANISM: Unknown
<220> FEATURE:
<223> OTHER INFORMATION: Obtained from genus Triticum species

<400> SEQUENCE: 70

Gln Val Val Asp Gln Gln Leu Ala Gly Arg
1               5                   10

<210> SEQ ID NO 71
<211> LENGTH: 11
<212> TYPE: PRT
<213> ORGANISM: Unknown
<220> FEATURE:
<223> OTHER INFORMATION: Obtained from genus Triticum species

<400> SEQUENCE: 71

Glu Leu Gln Glu Ser Ser Leu Glu Ala Cys Arg
1               5                   10

<210> SEQ ID NO 72
<211> LENGTH: 13
<212> TYPE: PRT
<213> ORGANISM: Unknown
<220> FEATURE:
<223> OTHER INFORMATION: Obtained from genus Triticum species

<400> SEQUENCE: 72

Ala Gln Gln Pro Ala Thr Gln Leu Pro Thr Val Cys Arg
1               5                   10

<210> SEQ ID NO 73
<211> LENGTH: 17
<212> TYPE: PRT
<213> ORGANISM: Unknown
<220> FEATURE:
<223> OTHER INFORMATION: Obtained from genus Triticum species

<400> SEQUENCE: 73

Gln Leu Gln Cys Glu Arg Glu Leu Gln Glu Ser Ser Leu Glu Ala Cys
1               5                   10                  15

Arg

<210> SEQ ID NO 74
<211> LENGTH: 20
<212> TYPE: PRT
<213> ORGANISM: Unknown
<220> FEATURE:
<223> OTHER INFORMATION: Obtained from genus Triticum species

<400> SEQUENCE: 74

Gln Val Val Asp Gln Gln Leu Ala Gly Arg Leu Pro Trp Ser Thr Gly
1               5                   10                  15

Leu Gln Met Arg
            20
```

<210> SEQ ID NO 75
<211> LENGTH: 37
<212> TYPE: PRT
<213> ORGANISM: Unknown
<220> FEATURE:
<223> OTHER INFORMATION: Obtained from genus Triticum species

<400> SEQUENCE: 75

Gln Gln Pro Val Gln Gly Gln Gln Pro Glu Gln Gly Gln Gln Pro Gly
1               5                   10                  15

Gln Trp Gln Gln Gly Tyr Tyr Pro Thr Ser Pro Gln Gln Leu Gly Gln
            20                  25                  30

Gly Gln Gln Pro Arg
        35

<210> SEQ ID NO 76
<211> LENGTH: 35
<212> TYPE: PRT
<213> ORGANISM: Unknown
<220> FEATURE:
<223> OTHER INFORMATION: Obtained from genus Triticum species

<400> SEQUENCE: 76

Gln Gly Tyr Tyr Pro Thr Ser Leu Gln Gln Pro Gly Gln Gly Gln Gln
1               5                   10                  15

Ile Gly Gln Gly Gln Gln Gly Tyr Tyr Pro Thr Ser Pro Gln His Thr
            20                  25                  30

Gly Gln Arg
        35

<210> SEQ ID NO 77
<211> LENGTH: 6
<212> TYPE: PRT
<213> ORGANISM: Unknown
<220> FEATURE:
<223> OTHER INFORMATION: Obtained from genus Triticum species

<400> SEQUENCE: 77

Gln Trp Leu Gln Pro Arg
1               5

<210> SEQ ID NO 78
<211> LENGTH: 11
<212> TYPE: PRT
<213> ORGANISM: Unknown
<220> FEATURE:
<223> OTHER INFORMATION: Obtained from genus Triticum species

<400> SEQUENCE: 78

Leu Glu Gly Gly Asp Ala Leu Leu Ala Ser Gln
1               5                   10

<210> SEQ ID NO 79
<211> LENGTH: 11
<212> TYPE: PRT
<213> ORGANISM: Unknown
<220> FEATURE:
<223> OTHER INFORMATION: Obtained from genus Triticum species

<400> SEQUENCE: 79

Leu Glu Gly Gly Asp Ala Leu Leu Ala Ser Gln
1               5                   10

```
<210> SEQ ID NO 80
<211> LENGTH: 6
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 80

Pro Ala Gly Pro Phe Arg
1               5

<210> SEQ ID NO 81
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 81

Pro Ala Gly Pro Phe Arg Ile Pro Lys
1               5

<210> SEQ ID NO 82
<211> LENGTH: 10
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 82

Ile Tyr Gln Thr Ala Thr His Leu Pro Lys
1               5                   10

<210> SEQ ID NO 83
<211> LENGTH: 8
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 83

Gln Val Ser Val Cys Pro Phe Lys
1               5

<210> SEQ ID NO 84
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 84

Gln Val Ser Val Cys Pro Phe Lys Lys
1               5

<210> SEQ ID NO 85
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 85
```

```
Gln Val Ser Val Cys Pro Phe Lys Lys
1               5

<210> SEQ ID NO 86
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 86

Pro Ala Gly Pro Phe Gly Ile Pro Lys
1               5

<210> SEQ ID NO 87
<211> LENGTH: 19
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 87

Gln Gln Leu Glu Gln Gln Gly Gln Gln Gly Pro His Leu Gln His Val
1               5                   10                  15

Ile Ser Arg

<210> SEQ ID NO 88
<211> LENGTH: 19
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 88

Gln Gln Leu Glu Gln Gln Gly Gln Gln Gly Pro His Leu Gln His Val
1               5                   10                  15

Ile Ser Arg

<210> SEQ ID NO 89
<211> LENGTH: 10
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 89

Ile Tyr Gln Thr Ala Thr His Leu Pro Arg
1               5                   10

<210> SEQ ID NO 90
<211> LENGTH: 10
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 90

Ile Tyr Gln Thr Ala Thr His Leu Pro Arg
1               5                   10
```

```
<210> SEQ ID NO 91
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 91

Gln Val Ser Val Cys Pro Phe Gln Lys
1               5

<210> SEQ ID NO 92
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 92

Gln Val Ser Val Cys Pro Phe Gln Lys
1               5

<210> SEQ ID NO 93
<211> LENGTH: 13
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 93

Val Cys Asn Ile Pro Gln Val Ser Val Cys Pro Phe Lys
1               5                   10

<210> SEQ ID NO 94
<211> LENGTH: 13
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 94

Val Cys Asn Ile Pro Gln Val Ser Val Cys Pro Phe Lys
1               5                   10

<210> SEQ ID NO 95
<211> LENGTH: 14
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 95

Val Cys Asn Ile Pro Gln Val Ser Val Cys Pro Phe Lys Lys
1               5                   10

<210> SEQ ID NO 96
<211> LENGTH: 14
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 96
```

```
Val Cys Asn Ile Pro Gln Val Ser Val Cys Pro Phe Lys Lys
1               5                   10
```

```
<210> SEQ ID NO 97
<211> LENGTH: 19
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 97

Gln Gln Leu Gly Gln Gln Gly Gln Gln Gly Pro Gln Val Gln His Val
1               5                   10                  15

Ile Ser Arg
```

```
<210> SEQ ID NO 98
<211> LENGTH: 19
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 98

Gln Gln Leu Gly Gln Gln Gly Gln Gln Gly Pro Gln Val Gln His Val
1               5                   10                  15

Ile Ser Arg
```

```
<210> SEQ ID NO 99
<211> LENGTH: 10
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 99

Ile Tyr Gln Thr Ala Thr His Leu Pro Arg
1               5                   10
```

```
<210> SEQ ID NO 100
<211> LENGTH: 5
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 100

Ala Gly Pro Phe Arg
1               5
```

```
<210> SEQ ID NO 101
<211> LENGTH: 7
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 101

Ala Val Lys Gln Gln Ile Arg
1               5
```

```
<210> SEQ ID NO 102
<211> LENGTH: 19
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 102

Gln Gln Gly Gln Gln Gln Gly Gln Gln Gly Gln Gln Leu Gln His Glu
1               5                   10                  15

Ile Ser Arg

<210> SEQ ID NO 103
<211> LENGTH: 6
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 103

Val Cys Asn Ile Pro Arg
1               5

<210> SEQ ID NO 104
<211> LENGTH: 8
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 104

Val Ser Ile Cys Pro Phe Gln Lys
1               5

<210> SEQ ID NO 105
<211> LENGTH: 8
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 105

Val Ser Ile Cys Pro Phe Gln Lys
1               5

<210> SEQ ID NO 106
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 106

Glu Phe Arg Gln Ala Gln His Leu Arg
1               5

<210> SEQ ID NO 107
<211> LENGTH: 9
<212> TYPE: PRT
<213> ORGANISM: Unknown
<220> FEATURE:
<223> OTHER INFORMATION: Obtained from mix of genus Brassica species and
      genus Sinapis species
```

```
<400> SEQUENCE: 107

Glu Phe Arg Gln Ala Gln His Leu Arg
1               5

<210> SEQ ID NO 108
<211> LENGTH: 6
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 108

Gln Ala Gln His Leu Arg
1               5

<210> SEQ ID NO 109
<211> LENGTH: 8
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 109

Ala Cys Gln Gln Trp Leu His Arg
1               5

<210> SEQ ID NO 110
<211> LENGTH: 18
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 110

Gln Gln Val Arg Gln Gln Gly His Gln Gln Gln Met Gln His Val Ile
1               5                   10                  15

Ser Arg

<210> SEQ ID NO 111
<211> LENGTH: 18
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 111

Gln Gln Val Arg Gln Gln Gly His Gln Gln Gln Met Gln His Val Ile
1               5                   10                  15

Ser Arg

<210> SEQ ID NO 112
<211> LENGTH: 10
<212> TYPE: PRT
<213> ORGANISM: Unknown
<220> FEATURE:
<223> OTHER INFORMATION: Obtained from mix of genus Brassica species and
      genus Sinapis species

<400> SEQUENCE: 112

Ile Tyr Gln Thr Ala Thr His Leu Pro Arg
1               5                   10
```

<210> SEQ ID NO 113
<211> LENGTH: 17
<212> TYPE: PRT
<213> ORGANISM: Unknown
<220> FEATURE:
<223> OTHER INFORMATION: Obtained from Avena sativa

<400> SEQUENCE: 113

Gln Phe Leu Val Gln Gln Cys Ser Pro Val Ala Val Val Pro Phe Leu
1               5                   10                  15

Arg

<210> SEQ ID NO 114
<211> LENGTH: 13
<212> TYPE: PRT
<213> ORGANISM: Unknown
<220> FEATURE:
<223> OTHER INFORMATION: Obtained from Avena sativa

<400> SEQUENCE: 114

Ser Gln Ile Leu Gln Gln Ser Ser Cys Gln Val Met Arg
1               5                   10

<210> SEQ ID NO 115
<211> LENGTH: 10
<212> TYPE: PRT
<213> ORGANISM: Unknown
<220> FEATURE:
<223> OTHER INFORMATION: Obtained from Avena sativa

<400> SEQUENCE: 115

Gln Leu Glu Gln Ile Pro Glu Gln Leu Arg
1               5                   10

<210> SEQ ID NO 116
<211> LENGTH: 10
<212> TYPE: PRT
<213> ORGANISM: Unknown
<220> FEATURE:
<223> OTHER INFORMATION: Obtained from Avena sativa

<400> SEQUENCE: 116

Gln Leu Glu Gln Ile Pro Glu Gln Leu Arg
1               5                   10

<210> SEQ ID NO 117
<211> LENGTH: 17
<212> TYPE: PRT
<213> ORGANISM: Unknown
<220> FEATURE:
<223> OTHER INFORMATION: Obtained from genus Secalin

<400> SEQUENCE: 117

Asn Val Leu Leu Gln Gln Cys Ser Pro Val Ala Leu Val Ser Ser Leu
1               5                   10                  15

Arg

<210> SEQ ID NO 118
<211> LENGTH: 17
<212> TYPE: PRT
<213> ORGANISM: Unknown
<220> FEATURE:
<223> OTHER INFORMATION: Obtained from genus Secalin

<400> SEQUENCE: 118

Asn Val Leu Leu Gln Gln Cys Ser Pro Val Ala Leu Val Ser Ser Leu
1               5                   10                  15

Arg

<210> SEQ ID NO 119
<211> LENGTH: 39
<212> TYPE: PRT
<213> ORGANISM: Unknown
<220> FEATURE:
<223> OTHER INFORMATION: Obtained from genus Secalin

<400> SEQUENCE: 119

Glu Gly Val Gln Ile Leu Leu Pro Gln Ser His Gln Gln His Val Gly
1               5                   10                  15

Gln Gly Ala Leu Ala Gln Val Gln Gly Ile Ile Gln Pro Gln Gln Leu
            20                  25                  30

Ser Gln Leu Glu Val Val Arg
        35

<210> SEQ ID NO 120
<211> LENGTH: 17
<212> TYPE: PRT
<213> ORGANISM: Unknown
<220> FEATURE:
<223> OTHER INFORMATION: Obtained from genus Secalin

<400> SEQUENCE: 120

Ser Leu Val Leu Gln Asn Leu Pro Thr Met Cys Asn Val Tyr Val Pro
1               5                   10                  15

Arg

<210> SEQ ID NO 121
<211> LENGTH: 17
<212> TYPE: PRT
<213> ORGANISM: Unknown
<220> FEATURE:
<223> OTHER INFORMATION: Obtained from genus Secalin

<400> SEQUENCE: 121

Ser Leu Val Leu Gln Asn Leu Pro Thr Met Cys Asn Val Tyr Val Pro
1               5                   10                  15

Arg

<210> SEQ ID NO 122
<211> LENGTH: 19
<212> TYPE: PRT
<213> ORGANISM: Unknown
<220> FEATURE:
<223> OTHER INFORMATION: Obtained from genus Secalin

<400> SEQUENCE: 122

Gln Cys Ser Thr Ile Gln Ala Pro Phe Ala Ser Ile Val Thr Gly Ile
1               5                   10                  15

Val Gly His

<210> SEQ ID NO 123
<211> LENGTH: 19
<212> TYPE: PRT
<213> ORGANISM: Unknown
<220> FEATURE:
<223> OTHER INFORMATION: Obtained from genus Secalin

<400> SEQUENCE: 123

```
Gln Cys Ser Thr Ile Gln Ala Pro Phe Ala Ser Ile Val Thr Gly Ile
1               5                   10                  15

Val Gly His

<210> SEQ ID NO 124
<211> LENGTH: 9
<212> TYPE: PRT
<213> ORGANISM: Unknown
<220> FEATURE:
<223> OTHER INFORMATION: Obtained from genus Sesamum

<400> SEQUENCE: 124

Ile Ser Gly Ala Gln Pro Ser Leu Arg
1               5

<210> SEQ ID NO 125
<211> LENGTH: 6
<212> TYPE: PRT
<213> ORGANISM: Unknown
<220> FEATURE:
<223> OTHER INFORMATION: Obtained from genus Sesamum

<400> SEQUENCE: 125

Leu Val Tyr Ile Glu Arg
1               5

<210> SEQ ID NO 126
<211> LENGTH: 19
<212> TYPE: PRT
<213> ORGANISM: Unknown
<220> FEATURE:
<223> OTHER INFORMATION: Obtained from genus Sesamum

<400> SEQUENCE: 126

Ala Phe Asp Ala Glu Leu Leu Ser Glu Ala Phe Asn Val Pro Gln Glu
1               5                   10                  15

Thr Ile Arg

<210> SEQ ID NO 127
<211> LENGTH: 7
<212> TYPE: PRT
<213> ORGANISM: Unknown
<220> FEATURE:
<223> OTHER INFORMATION: Obtained from genus Sesamum

<400> SEQUENCE: 127

Gly Leu Ile Val Met Ala Arg
1               5

<210> SEQ ID NO 128
<211> LENGTH: 7
<212> TYPE: PRT
<213> ORGANISM: Unknown
<220> FEATURE:
<223> OTHER INFORMATION: Obtained from genus Sesamum

<400> SEQUENCE: 128

Glu Ala Asp Ile Phe Ser Arg
1               5

<210> SEQ ID NO 129
<211> LENGTH: 11
<212> TYPE: PRT
<213> ORGANISM: Unknown
<220> FEATURE:
```

<223> OTHER INFORMATION: Obtained from genus Sesamum

<400> SEQUENCE: 129

Ser Pro Leu Ala Gly Tyr Thr Ser Val Ile Arg
1               5                   10

<210> SEQ ID NO 130
<211> LENGTH: 22
<212> TYPE: PRT
<213> ORGANISM: Unknown
<220> FEATURE:
<223> OTHER INFORMATION: Obtained from genus Sesamum

<400> SEQUENCE: 130

Ala Met Pro Leu Gln Val Ile Thr Asn Ser Tyr Gln Ile Ser Pro Asn
1               5                   10                  15

Gln Ala Gln Ala Leu Lys
            20

<210> SEQ ID NO 131
<211> LENGTH: 7
<212> TYPE: PRT
<213> ORGANISM: Unknown
<220> FEATURE:
<223> OTHER INFORMATION: Obtained from genus Sesamum

<400> SEQUENCE: 131

His Cys Met Gln Trp Met Arg
1               5

<210> SEQ ID NO 132
<211> LENGTH: 11
<212> TYPE: PRT
<213> ORGANISM: Unknown
<220> FEATURE:
<223> OTHER INFORMATION: Obtained from genus Sesamum

<400> SEQUENCE: 132

Met Cys Gly Met Ser Tyr Pro Thr Glu Cys Arg
1               5                   10

<210> SEQ ID NO 133
<211> LENGTH: 9
<212> TYPE: PRT
<213> ORGANISM: Unknown
<220> FEATURE:
<223> OTHER INFORMATION: Obtained from genus Triticum

<400> SEQUENCE: 133

Ser Val Ala Val Ser Gln Val Ala Arg
1               5

<210> SEQ ID NO 134
<211> LENGTH: 16
<212> TYPE: PRT
<213> ORGANISM: Unknown
<220> FEATURE:
<223> OTHER INFORMATION: Obtained from genus Triticum

<400> SEQUENCE: 134

Glu His Gly Ala Gln Glu Gly Gln Ala Gly Thr Gly Ala Phe Pro Arg
1               5                   10                  15

<210> SEQ ID NO 135
<211> LENGTH: 10
<212> TYPE: PRT

```
<213> ORGANISM: Unknown
<220> FEATURE:
<223> OTHER INFORMATION: Obtained from genus Triticum

<400> SEQUENCE: 135

Gln Val Val Asp Gln Gln Leu Ala Gly Arg
1               5                   10

<210> SEQ ID NO 136
<211> LENGTH: 10
<212> TYPE: PRT
<213> ORGANISM: Unknown
<220> FEATURE:
<223> OTHER INFORMATION: Obtained from genus Triticum

<400> SEQUENCE: 136

Ile Phe Trp Gly Ile Pro Ala Leu Leu Lys
1               5                   10

<210> SEQ ID NO 137
<211> LENGTH: 10
<212> TYPE: PRT
<213> ORGANISM: Unknown
<220> FEATURE:
<223> OTHER INFORMATION: Obtained from genus Triticum

<400> SEQUENCE: 137

Leu Pro Trp Ser Thr Gly Leu Gln Met Arg
1               5                   10

<210> SEQ ID NO 138
<211> LENGTH: 11
<212> TYPE: PRT
<213> ORGANISM: Unknown
<220> FEATURE:
<223> OTHER INFORMATION: Obtained from genus Triticum

<400> SEQUENCE: 138

Tyr Asp Pro Thr Ala Tyr Asn Thr Ile Leu Arg
1               5                   10

<210> SEQ ID NO 139
<211> LENGTH: 8
<212> TYPE: PRT
<213> ORGANISM: Unknown
<220> FEATURE:
<223> OTHER INFORMATION: Obtained from Bertolletia excelsa

<400> SEQUENCE: 139

Gln Gln Met Leu Ser His Cys Arg
1               5

<210> SEQ ID NO 140
<211> LENGTH: 21
<212> TYPE: PRT
<213> ORGANISM: Unknown
<220> FEATURE:
<223> OTHER INFORMATION: Obtained from Bertolletia excelsa

<400> SEQUENCE: 140

Gly Met Glu Pro His Met Ser Glu Cys Cys Glu Gln Leu Glu Gly Met
1               5                   10                  15

Asp Glu Ser Cys Arg
            20

<210> SEQ ID NO 141
```

```
<211> LENGTH: 5
<212> TYPE: PRT
<213> ORGANISM: Unknown
<220> FEATURE:
<223> OTHER INFORMATION: Obtained from Bertolletia excelsa

<400> SEQUENCE: 141

Met Met Met Met Arg
1               5

<210> SEQ ID NO 142
<211> LENGTH: 9
<212> TYPE: PRT
<213> ORGANISM: Unknown
<220> FEATURE:
<223> OTHER INFORMATION: Obtained from Bertolletia excelsa

<400> SEQUENCE: 142

Met Gln Gln Glu Glu Met Gln Pro Arg
1               5

<210> SEQ ID NO 143
<211> LENGTH: 8
<212> TYPE: PRT
<213> ORGANISM: Unknown
<220> FEATURE:
<223> OTHER INFORMATION: Obtained from Bertolletia excelsa

<400> SEQUENCE: 143

Leu Ala Glu Asn Ile Pro Ser Arg
1               5

<210> SEQ ID NO 144
<211> LENGTH: 7
<212> TYPE: PRT
<213> ORGANISM: Unknown
<220> FEATURE:
<223> OTHER INFORMATION: Obtained from Bertolletia excelsa

<400> SEQUENCE: 144

Cys Asn Leu Ser Pro Met Arg
1               5

<210> SEQ ID NO 145
<211> LENGTH: 8
<212> TYPE: PRT
<213> ORGANISM: Unknown
<220> FEATURE:
<223> OTHER INFORMATION: Obtained from Bertolletia excelsa

<400> SEQUENCE: 145

Gln Gln Gln Leu Asn His Cys Arg
1               5

<210> SEQ ID NO 146
<211> LENGTH: 6
<212> TYPE: PRT
<213> ORGANISM: Unknown
<220> FEATURE:
<223> OTHER INFORMATION: Obtained from Bertolletia excelsa

<400> SEQUENCE: 146

Met Asp Glu Met Cys Arg
1               5

<210> SEQ ID NO 147
<211> LENGTH: 7
```

```
<212> TYPE: PRT
<213> ORGANISM: Unknown
<220> FEATURE:
<223> OTHER INFORMATION: Obtained from Bertolletia excelsa

<400> SEQUENCE: 147

Cys Asn Leu Ser Pro Gln Arg
1               5

<210> SEQ ID NO 148
<211> LENGTH: 8
<212> TYPE: PRT
<213> ORGANISM: Unknown
<220> FEATURE:
<223> OTHER INFORMATION: Obtained from Bertolletia excelsa

<400> SEQUENCE: 148

Cys Ala Gly Val Ala Ala Leu Arg
1               5

<210> SEQ ID NO 149
<211> LENGTH: 8
<212> TYPE: PRT
<213> ORGANISM: Unknown
<220> FEATURE:
<223> OTHER INFORMATION: Obtained from Bertolletia excelsa

<400> SEQUENCE: 149

Leu Tyr Tyr Val Thr Gln Gly Arg
1               5

<210> SEQ ID NO 150
<211> LENGTH: 10
<212> TYPE: PRT
<213> ORGANISM: Unknown
<220> FEATURE:
<223> OTHER INFORMATION: Obtained from Bertolletia excelsa

<400> SEQUENCE: 150

His Phe Phe Leu Ala Gly Asn Ile Gln Arg
1               5                   10

<210> SEQ ID NO 151
<211> LENGTH: 12
<212> TYPE: PRT
<213> ORGANISM: Unknown
<220> FEATURE:
<223> OTHER INFORMATION: Obtained from Bertolletia excelsa

<400> SEQUENCE: 151

Gly Gly Gln Gln Ile Leu Ala Asp Asn Val Phe Lys
1               5                   10

<210> SEQ ID NO 152
<211> LENGTH: 21
<212> TYPE: PRT
<213> ORGANISM: Unknown
<220> FEATURE:
<223> OTHER INFORMATION: Obtained from Bertolletia excelsa

<400> SEQUENCE: 152

Gly Phe Asn Met Glu Ala Leu Ala Asp Val Leu Gly Phe Gly Met Asp
1               5                   10                  15

Thr Glu Thr Ala Arg
            20
```

```
<210> SEQ ID NO 153
<211> LENGTH: 14
<212> TYPE: PRT
<213> ORGANISM: Unknown
<220> FEATURE:
<223> OTHER INFORMATION: Obtained from Bertolletia excelsa

<400> SEQUENCE: 153

Gly Val Leu Tyr Glu Asn Ala Met Met Ala Pro Leu Trp Arg
1               5                   10

<210> SEQ ID NO 154
<211> LENGTH: 12
<212> TYPE: PRT
<213> ORGANISM: Unknown
<220> FEATURE:
<223> OTHER INFORMATION: Obtained from Bertolletia excelsa

<400> SEQUENCE: 154

Gly Ile Pro Val Gly Val Leu Ala Asn Ala Tyr Arg
1               5                   10

<210> SEQ ID NO 155
<211> LENGTH: 11
<212> TYPE: PRT
<213> ORGANISM: Unknown
<220> FEATURE:
<223> OTHER INFORMATION: Obtained from Bertolletia excelsa

<400> SEQUENCE: 155

Asp Glu Ala Val Leu Phe Gln Pro Gly Ser Arg
1               5                   10

<210> SEQ ID NO 156
<211> LENGTH: 9
<212> TYPE: PRT
<213> ORGANISM: Unknown
<220> FEATURE:
<223> OTHER INFORMATION: Obtained from Corylus avellana

<400> SEQUENCE: 156

Tyr Phe Gly Glu Cys Asn Leu Asp Arg
1               5

<210> SEQ ID NO 157
<211> LENGTH: 9
<212> TYPE: PRT
<213> ORGANISM: Unknown
<220> FEATURE:
<223> OTHER INFORMATION: Obtained from genus Corylus

<400> SEQUENCE: 157

Leu Asn Ala Leu Glu Pro Thr Asn Arg
1               5

<210> SEQ ID NO 158
<211> LENGTH: 23
<212> TYPE: PRT
<213> ORGANISM: Unknown
<220> FEATURE:
<223> OTHER INFORMATION: Obtained from genus Corylus

<400> SEQUENCE: 158

Thr Ile Glu Pro Asn Gly Leu Leu Pro Gln Tyr Ser Asn Ala Pro
1               5                   10                  15

Glu Leu Ile Tyr Ile Glu Arg
            20
```

```
<210> SEQ ID NO 159
<211> LENGTH: 14
<212> TYPE: PRT
<213> ORGANISM: Unknown
<220> FEATURE:
<223> OTHER INFORMATION: Obtained from genus Corylus

<400> SEQUENCE: 159

His Phe Tyr Leu Ala Gly Asn Pro Asp Asp Glu His Gln Arg
1               5                   10

<210> SEQ ID NO 160
<211> LENGTH: 9
<212> TYPE: PRT
<213> ORGANISM: Unknown
<220> FEATURE:
<223> OTHER INFORMATION: Obtained from genus Corylus

<400> SEQUENCE: 160

Gln Gly Gln Gln Gln Phe Gly Gln Arg
1               5

<210> SEQ ID NO 161
<211> LENGTH: 5
<212> TYPE: PRT
<213> ORGANISM: Unknown
<220> FEATURE:
<223> OTHER INFORMATION: Obtained from genus Corylus

<400> SEQUENCE: 161

Gln Glu Trp Glu Arg
1               5

<210> SEQ ID NO 162
<211> LENGTH: 10
<212> TYPE: PRT
<213> ORGANISM: Unknown
<220> FEATURE:
<223> OTHER INFORMATION: Obtained from genus Corylus

<400> SEQUENCE: 162

Ala Asp Ile Tyr Thr Glu Gln Val Gly Arg
1               5                   10

<210> SEQ ID NO 163
<211> LENGTH: 13
<212> TYPE: PRT
<213> ORGANISM: Unknown
<220> FEATURE:
<223> OTHER INFORMATION: Obtained from genus Corylus

<400> SEQUENCE: 163

Ile Asn Thr Val Asn Ser Asn Thr Leu Pro Val Leu Arg
1               5                   10

<210> SEQ ID NO 164
<211> LENGTH: 8
<212> TYPE: PRT
<213> ORGANISM: Unknown
<220> FEATURE:
<223> OTHER INFORMATION: Obtained from genus Corylus

<400> SEQUENCE: 164

Trp Leu Gln Leu Ser Ala Glu Arg
1               5
```

```
<210> SEQ ID NO 165
<211> LENGTH: 15
<212> TYPE: PRT
<213> ORGANISM: Unknown
<220> FEATURE:
<223> OTHER INFORMATION: Obtained from genus Corylus

<400> SEQUENCE: 165

Gln Gly Gln Val Leu Thr Ile Pro Gln Asn Phe Ala Val Ala Lys
1               5                   10                  15

<210> SEQ ID NO 166
<211> LENGTH: 12
<212> TYPE: PRT
<213> ORGANISM: Unknown
<220> FEATURE:
<223> OTHER INFORMATION: Obtained from genus Corylus

<400> SEQUENCE: 166

Ala Glu Ser Glu Gly Phe Glu Trp Val Ala Phe Lys
1               5                   10

<210> SEQ ID NO 167
<211> LENGTH: 13
<212> TYPE: PRT
<213> ORGANISM: Unknown
<220> FEATURE:
<223> OTHER INFORMATION: Obtained from genus Corylus

<400> SEQUENCE: 167

Thr Asn Asp Asn Ala Gln Ile Ser Pro Leu Ala Gly Arg
1               5                   10

<210> SEQ ID NO 168
<211> LENGTH: 15
<212> TYPE: PRT
<213> ORGANISM: Unknown
<220> FEATURE:
<223> OTHER INFORMATION: Obtained from genus Corylus

<400> SEQUENCE: 168

Ala Leu Pro Asp Asp Val Leu Ala Asn Ala Phe Gln Ile Ser Arg
1               5                   10                  15

<210> SEQ ID NO 169
<211> LENGTH: 7
<212> TYPE: PRT
<213> ORGANISM: Unknown
<220> FEATURE:
<223> OTHER INFORMATION: Obtained from genus Corylus

<400> SEQUENCE: 169

Gln Glu Thr Thr Leu Val Arg
1               5

<210> SEQ ID NO 170
<211> LENGTH: 10
<212> TYPE: PRT
<213> ORGANISM: Unknown
<220> FEATURE:
<223> OTHER INFORMATION: Obtained from genus Corylus

<400> SEQUENCE: 170

Val Glu Glu Ile Asp His Ala Asn Phe Lys
1               5                   10
```

```
<210> SEQ ID NO 171
<211> LENGTH: 14
<212> TYPE: PRT
<213> ORGANISM: Unknown
<220> FEATURE:
<223> OTHER INFORMATION: Obtained from genus Corylus

<400> SEQUENCE: 171

Ala Val Glu Ala Tyr Leu Leu Ala His Pro Asp Ala Tyr Cys
1               5                   10

<210> SEQ ID NO 172
<211> LENGTH: 14
<212> TYPE: PRT
<213> ORGANISM: Unknown
<220> FEATURE:
<223> OTHER INFORMATION: Obtained from genus Corylus

<400> SEQUENCE: 172

Ala Val Glu Ala Tyr Leu Leu Ala His Pro Asp Ala Tyr Cys
1               5                   10

<210> SEQ ID NO 173
<211> LENGTH: 12
<212> TYPE: PRT
<213> ORGANISM: Unknown
<220> FEATURE:
<223> OTHER INFORMATION: Obtained from genus Macadamia

<400> SEQUENCE: 173

Gln Cys Met Gln Leu Glu Thr Ser Gly Gln Met Arg
1               5                   10

<210> SEQ ID NO 174
<211> LENGTH: 7
<212> TYPE: PRT
<213> ORGANISM: Unknown
<220> FEATURE:
<223> OTHER INFORMATION: Obtained from genus Macadamia

<400> SEQUENCE: 174

Cys Val Ser Gln Cys Asp Lys
1               5

<210> SEQ ID NO 175
<211> LENGTH: 9
<212> TYPE: PRT
<213> ORGANISM: Unknown
<220> FEATURE:
<223> OTHER INFORMATION: Obtained from genus Macadamia

<400> SEQUENCE: 175

Phe Glu Glu Asp Ile Asp Trp Ser Lys
1               5

<210> SEQ ID NO 176
<211> LENGTH: 8
<212> TYPE: PRT
<213> ORGANISM: Unknown
<220> FEATURE:
<223> OTHER INFORMATION: Obtained from genus Macadamia

<400> SEQUENCE: 176

His Met Gln Ile Cys Gln Gln Arg
1               5

<210> SEQ ID NO 177
```

```
<211> LENGTH: 8
<212> TYPE: PRT
<213> ORGANISM: Unknown
<220> FEATURE:
<223> OTHER INFORMATION: Obtained from genus Macadamia

<400> SEQUENCE: 177

His Cys Glu Gln Gln Glu Pro Arg
1               5

<210> SEQ ID NO 178
<211> LENGTH: 7
<212> TYPE: PRT
<213> ORGANISM: Unknown
<220> FEATURE:
<223> OTHER INFORMATION: Obtained from genus Macadamia

<400> SEQUENCE: 178

Leu Gln Tyr Gln Cys Gln Arg
1               5

<210> SEQ ID NO 179
<211> LENGTH: 6
<212> TYPE: PRT
<213> ORGANISM: Unknown
<220> FEATURE:
<223> OTHER INFORMATION: Obtained from genus Macadamia

<400> SEQUENCE: 179

Glu Gly Val Ile Ile Arg
1               5

<210> SEQ ID NO 180
<211> LENGTH: 6
<212> TYPE: PRT
<213> ORGANISM: Unknown
<220> FEATURE:
<223> OTHER INFORMATION: Obtained from genus Macadamia

<400> SEQUENCE: 180

Glu Ser Glu Phe Asp Arg
1               5

<210> SEQ ID NO 181
<211> LENGTH: 7
<212> TYPE: PRT
<213> ORGANISM: Unknown
<220> FEATURE:
<223> OTHER INFORMATION: Obtained from genus Macadamia

<400> SEQUENCE: 181

Gln Gln Tyr Gln Cys Gln Arg
1               5

<210> SEQ ID NO 182
<211> LENGTH: 9
<212> TYPE: PRT
<213> ORGANISM: Unknown
<220> FEATURE:
<223> OTHER INFORMATION: Obtained from Arachis hypogaea

<400> SEQUENCE: 182

Asn Leu Pro Gln Gln Cys Gly Leu Arg
1               5

<210> SEQ ID NO 183
<211> LENGTH: 9
```

<212> TYPE: PRT
<213> ORGANISM: Unknown
<220> FEATURE:
<223> OTHER INFORMATION: Obtained from Arachis hypogaea

<400> SEQUENCE: 183

Asn Asn Pro Phe Tyr Phe Pro Ser Arg
1               5

<210> SEQ ID NO 184
<211> LENGTH: 11
<212> TYPE: PRT
<213> ORGANISM: Unknown
<220> FEATURE:
<223> OTHER INFORMATION: Obtained from Arachis hypogaea

<400> SEQUENCE: 184

Thr Ala Asn Asp Leu Asn Leu Leu Ile Leu Arg
1               5                   10

<210> SEQ ID NO 185
<211> LENGTH: 13
<212> TYPE: PRT
<213> ORGANISM: Unknown
<220> FEATURE:
<223> OTHER INFORMATION: Obtained from Arachis hypogaea

<400> SEQUENCE: 185

Asp Leu Ala Phe Pro Gly Ser Gly Glu Gln Val Glu Lys
1               5                   10

<210> SEQ ID NO 186
<211> LENGTH: 13
<212> TYPE: PRT
<213> ORGANISM: Unknown
<220> FEATURE:
<223> OTHER INFORMATION: Obtained from Arachis hypogaea

<400> SEQUENCE: 186

Ser Pro Asp Ile Tyr Asn Pro Gln Ala Gly Ser Leu Lys
1               5                   10

<210> SEQ ID NO 187
<211> LENGTH: 14
<212> TYPE: PRT
<213> ORGANISM: Unknown
<220> FEATURE:
<223> OTHER INFORMATION: Obtained from Arachis hypogaea

<400> SEQUENCE: 187

Val Leu Leu Glu Glu Asn Ala Gly Gly Glu Gln Glu Glu Arg
1               5                   10

<210> SEQ ID NO 188
<211> LENGTH: 8
<212> TYPE: PRT
<213> ORGANISM: Unknown
<220> FEATURE:
<223> OTHER INFORMATION: Obtained from Pistacia vera

<400> SEQUENCE: 188

Cys Ala Gly Val Ala Val Ala Arg
1               5

<210> SEQ ID NO 189
<211> LENGTH: 9
<212> TYPE: PRT

```
<213> ORGANISM: Unknown
<220> FEATURE:
<223> OTHER INFORMATION: Obtained from Pistacia vera

<400> SEQUENCE: 189

His Thr Ile Gln Pro Asn Gly Leu Arg
1               5

<210> SEQ ID NO 190
<211> LENGTH: 14
<212> TYPE: PRT
<213> ORGANISM: Unknown
<220> FEATURE:
<223> OTHER INFORMATION: Obtained from Pistacia vera

<400> SEQUENCE: 190

Ile Leu Ala Glu Val Phe Gln Val Glu Gln Ser Leu Val Lys
1               5                   10

<210> SEQ ID NO 191
<211> LENGTH: 12
<212> TYPE: PRT
<213> ORGANISM: Unknown
<220> FEATURE:
<223> OTHER INFORMATION: Obtained from Pistacia vera

<400> SEQUENCE: 191

Gly Phe Glu Ser Glu Glu Glu Ser Glu Tyr Glu Arg
1               5                   10

<210> SEQ ID NO 192
<211> LENGTH: 10
<212> TYPE: PRT
<213> ORGANISM: Unknown
<220> FEATURE:
<223> OTHER INFORMATION: Obtained from Pistacia vera

<400> SEQUENCE: 192

Ser Asp Ile Tyr Thr Pro Glu Val Gly Arg
1               5                   10

<210> SEQ ID NO 193
<211> LENGTH: 13
<212> TYPE: PRT
<213> ORGANISM: Unknown
<220> FEATURE:
<223> OTHER INFORMATION: Obtained from Pistacia vera

<400> SEQUENCE: 193

Ile Thr Ser Leu Asn Ser Leu Asn Leu Pro Ile Leu Lys
1               5                   10

<210> SEQ ID NO 194
<211> LENGTH: 8
<212> TYPE: PRT
<213> ORGANISM: Unknown
<220> FEATURE:
<223> OTHER INFORMATION: Obtained from Pistacia vera

<400> SEQUENCE: 194

Trp Leu Gln Leu Ser Ala Glu Arg
1               5

<210> SEQ ID NO 195
<211> LENGTH: 7
<212> TYPE: PRT
<213> ORGANISM: Unknown
```

```
<220> FEATURE:
<223> OTHER INFORMATION: Obtained from Pistacia veram

<400> SEQUENCE: 195

Phe Glu Trp Ile Ser Phe Lys
1               5

<210> SEQ ID NO 196
<211> LENGTH: 14
<212> TYPE: PRT
<213> ORGANISM: Unknown
<220> FEATURE:
<223> OTHER INFORMATION: Obtained from Pistacia vera

<400> SEQUENCE: 196

Ala Met Ile Ser Pro Leu Ala Gly Ser Thr Ser Val Leu Arg
1               5                   10

<210> SEQ ID NO 197
<211> LENGTH: 15
<212> TYPE: PRT
<213> ORGANISM: Unknown
<220> FEATURE:
<223> OTHER INFORMATION: Obtained from Pistacia vera

<400> SEQUENCE: 197

Ala Met Pro Glu Glu Val Leu Ala Asn Ala Phe Gln Ile Ser Arg
1               5                   10                  15

<210> SEQ ID NO 198
<211> LENGTH: 16
<212> TYPE: PRT
<213> ORGANISM: Unknown
<220> FEATURE:
<223> OTHER INFORMATION: Obtained from Pistacia vera

<400> SEQUENCE: 198

Phe Gln Thr Gln Cys Gln Ile Gln Asn Leu Asn Ala Leu Glu Pro Lys
1               5                   10                  15

<210> SEQ ID NO 199
<211> LENGTH: 27
<212> TYPE: PRT
<213> ORGANISM: Unknown
<220> FEATURE:
<223> OTHER INFORMATION: Obtained from Pistacia vera

<400> SEQUENCE: 199

Ile Glu Ser Glu Ala Gly Val Thr Glu Phe Trp Asp Gln Asn Glu Glu
1               5                   10                  15

Gln Leu Gln Cys Ala Asn Val Ala Val Phe Arg
            20                  25

<210> SEQ ID NO 200
<211> LENGTH: 21
<212> TYPE: PRT
<213> ORGANISM: Unknown
<220> FEATURE:
<223> OTHER INFORMATION: Obtained from Pistacia vera

<400> SEQUENCE: 200

Leu Val Leu Val Ala Leu Ala Asp Val Gly Asn Ser Glu Asn Gln Leu
1               5                   10                  15

Asp Gln Tyr Leu Arg
            20
```

<210> SEQ ID NO 201
<211> LENGTH: 5
<212> TYPE: PRT
<213> ORGANISM: Unknown
<220> FEATURE:
<223> OTHER INFORMATION: Obtained from Pistacia vera

<400> SEQUENCE: 201

Gly Ile Ile Val Arg
1               5

<210> SEQ ID NO 202
<211> LENGTH: 15
<212> TYPE: PRT
<213> ORGANISM: Unknown
<220> FEATURE:
<223> OTHER INFORMATION: Obtained from Pistacia vera

<400> SEQUENCE: 202

Gly Leu Pro Leu Asp Val Ile Gln Asn Ser Phe Asp Ile Ser Arg
1               5                   10                  15

<210> SEQ ID NO 203
<211> LENGTH: 11
<212> TYPE: PRT
<213> ORGANISM: Unknown
<220> FEATURE:
<223> OTHER INFORMATION: Obtained from Pistacia vera

<400> SEQUENCE: 203

Ser Glu Met Thr Ile Phe Ala Pro Gly Ser Arg
1               5                   10

<210> SEQ ID NO 204
<211> LENGTH: 12
<212> TYPE: PRT
<213> ORGANISM: Unknown
<220> FEATURE:
<223> OTHER INFORMATION: Obtained from Juglans regia

<400> SEQUENCE: 204

Gln Gln Asn Leu Asn His Cys Gln Tyr Tyr Leu Arg
1               5                   10

<210> SEQ ID NO 205
<211> LENGTH: 19
<212> TYPE: PRT
<213> ORGANISM: Unknown
<220> FEATURE:
<223> OTHER INFORMATION: Obtained from Juglans regia

<400> SEQUENCE: 205

Gln Cys Cys Gln Gln Leu Ser Gln Met Asp Glu Gln Cys Gln Cys Glu
1               5                   10                  15

Gly Leu Arg

<210> SEQ ID NO 206
<211> LENGTH: 12
<212> TYPE: PRT
<213> ORGANISM: Unknown
<220> FEATURE:
<223> OTHER INFORMATION: Obtained from Juglans regia

<400> SEQUENCE: 206

Gly Glu Glu Met Glu Glu Met Val Gln Ser Ala Arg
1               5                   10

<210> SEQ ID NO 207
<211> LENGTH: 12
<212> TYPE: PRT
<213> ORGANISM: Unknown
<220> FEATURE:
<223> OTHER INFORMATION: Obtained from Juglans regia

<400> SEQUENCE: 207

Asp Leu Pro Asn Glu Cys Gly Ile Ser Ser Gln Arg
1               5                   10

<210> SEQ ID NO 208
<211> LENGTH: 9
<212> TYPE: PRT
<213> ORGANISM: Unknown
<220> FEATURE:
<223> OTHER INFORMATION: Obtained from Juglans regia

<400> SEQUENCE: 208

Leu Asp Ala Leu Glu Pro Thr Asn Arg
1               5

<210> SEQ ID NO 209
<211> LENGTH: 27
<212> TYPE: PRT
<213> ORGANISM: Unknown
<220> FEATURE:
<223> OTHER INFORMATION: Obtained from Juglans regia

<400> SEQUENCE: 209

Gly Leu Gly Asn Asn Val Phe Ser Gly Phe Asp Ala Asp Phe Leu Ala
1               5                   10                  15

Asp Ala Phe Asn Val Asp Thr Glu Thr Ala Arg
            20                  25

<210> SEQ ID NO 210
<211> LENGTH: 8
<212> TYPE: PRT
<213> ORGANISM: Unknown
<220> FEATURE:
<223> OTHER INFORMATION: Obtained from Juglans regia

<400> SEQUENCE: 210

Trp Leu Gln Leu Ser Ala Glu Arg
1               5

<210> SEQ ID NO 211
<211> LENGTH: 15
<212> TYPE: PRT
<213> ORGANISM: Unknown
<220> FEATURE:
<223> OTHER INFORMATION: Obtained from Juglans regia

<400> SEQUENCE: 211

Ala Leu Pro Glu Glu Val Leu Ala Thr Ala Phe Gln Ile Pro Arg
1               5                   10                  15

<210> SEQ ID NO 212
<211> LENGTH: 15
<212> TYPE: PRT
<213> ORGANISM: Unknown

```
<220> FEATURE:
<223> OTHER INFORMATION: Obtained from Juglans regia

<400> SEQUENCE: 212

Ala Leu Pro Glu Glu Val Leu Ala Thr Ala Phe Gln Ile Pro Arg
1               5                   10                  15
```

SYSTEM AND METHOD FOR THE DETECTION OF ALLERGENS

RELATED APPLICATION

This application claims the benefit of U.S. Provisional Application Ser. No. 61/530,612, filed Sep. 4, 2012, the content of which is incorporated by reference herein in its entirety.

FIELD

The invention relates generally to kits and methods for detecting and quantifying allergens in samples, such as food samples, using mass spectrometry.

BACKGROUND

Food allergy can elicit harmful immune responses, e.g., as dermatitis, asthma, gastrointestinal impairment, anaphylaxis shock, etc. Conventional methods for detecting and/or quantifying allergens in food samples generally employ immunoassays, which can suffer from a number of shortcomings. For example, one such method known as Enzyme Linked Immunosorbent Assay (ELISA) requires the use of expensive kits and is semi-quantitative at best. Additionally, conventional immunoassays are generally limited to a single allergen in each screen and frequently result in false positives due to a lack of specificity.

Accordingly, there is a need for improved kits and methods for detecting and quantifying allergens in food samples.

SUMMARY

According to various embodiments, methods and kits for detecting and/or quantifying allergens in a sample using mass spectrometry are provided herein. As described below, these methods and kits can enable the detection and/or quantitation of at least one allergen (e.g., ovalbumin, lysozyme, casein, lactoglobulin, high and low molecular weight glutenins, wheat, rye, oats, barley, mustard, sesame and various nuts including macadamia, pistachio, brazil, walnuts, peanuts and hazelnuts) in a sample by taking advantage of one or more amino acid sequences specific to the allergen of interest. For example, allergen-specific tryptic peptides can be detected using Liquid Chromatography-Tandem Mass Spectrometry (LC-MS/MS). In many embodiments, selected Multiple Reaction Monitoring (MRM) transitions can be observed for each peptide to enable a reliable quantitation of the allergen in a food sample, for example.

According to various embodiments, a set of peptides specific to various allergens is disclosed. For example, each of the allergens ovalbumin, lysozyme, casein (isoform S1 and S2), lactoglobulin, glutens containing high and low molecular weight glutenins, wheat, rye, oats, barley, mustard, sesame and various nuts can be detected and/or quantified using an isolated peptide specific to that allergen. In some cases, these allergen terms are broad definitions which encompasses various types of peptides from different proteins and in some cases different genus and/or species of allergens. For example, the term mustard encompasses allergens obtained from species in both the genus *Brassica* and Genus *Sinapis*, both understood to be forms of mustard. By way of example, an isolated peptide specific to ovalbumin, an allergen found in chicken eggs, can have one or more of the amino acid sequence of SEQ ID NOS: 1-7. An isolated peptide specific to lysozyme, an allergen also found in chicken eggs, can have one or more of the amino acid sequence of SEQ ID NOS: 8-11. An isolated peptide specific to casein S1, a milk protein, can have one or more of the amino acid sequence of SEQ. ID NOS. 12-18. An isolated peptide specific to casein S2, another isoform of the milk protein casein, can have one or more of the amino acid sequence of SEQ. ID NOS. 19-23. Isolated peptides specific to lactoglobulin, another allergen found in milk, can have one or more of the amino acid sequences of SEQ. ID NOS. 24-29. An isolated peptide specific to barley proteins, can have one or more of the amino acid sequence of SEQ. ID NOS. 30-33. An isolated peptide specific to low molecular weight glutenin, can have one or more of the amino acid sequence of SEQ. ID NOS. 34-59. An isolated peptide specific to high molecular weight glutenin, can have one or more of the amino acid sequence of SEQ. ID NOS. 60-79. An isolated peptide specific to proteins of various species classified as mustard, can have one or more of the amino acid sequence of SEQ. ID NOS. 80-112. An isolated peptide specific to oat proteins, can have one or more of the amino acid sequence of SEQ. ID NOS. 113-116. An isolated peptide specific to rye proteins, can have one or more of the amino acid sequence of SEQ. ID NOS. 117-123. An isolated peptide specific to sesame proteins, can have one or more of the amino acid sequence of SEQ. ID NOS. 124-132. An isolated peptide specific to wheat proteins, can have one or more of the amino acid sequence of SEQ. ID NOS. 133-138. An isolated peptide specific to brazil nut proteins, can have one or more of the amino acid sequence of SEQ. ID NOS. 139-155. An isolated peptide specific to hazelnut proteins, can have one or more of the amino acid sequence of SEQ. ID NOS. 156-172. An isolated peptide specific to macadamia nut proteins, can have one or more of the amino acid sequence of SEQ. ID NOS. 173-181. An isolated peptide specific to peanut proteins, can have one or more of the amino acid sequence of SEQ. ID NOS. 182-187. An isolated peptide specific to pistachio nut proteins, can have one or more of the amino acid sequence of SEQ. ID NOS. 188-203 and finally an isolated peptide specific to walnut proteins, can have one or more of the amino acid sequence of SEQ. ID NOS 204-212.

Each of the above-described peptides can be detected and/or quantified using specific MRM transitions associated with each of the allergen-specific peptides. Optimized MRM transitions for each of the peptides, according to various embodiments, is discussed below in Tables 1-19.

In one aspect, a method of screening a sample for an allergen is provided. The method includes obtaining a sample and digesting the sample with at least one proteolytic enzyme (e.g., trypsin) to fragment at least one allergen present in the sample, if any, into a plurality of peptides. The allergen can be at least one of ovalbumin, lysozyme, casein, lactoglobulin, high and low glutenins, and proteins obtained from wheat, rye, oats, barley, mustard, sesame, and various types of nuts including macadamia, pistachio, brazil, walnuts, peanuts and hazelnuts. The method additionally includes quantifying at least one of the allergens by determining an amount of at least one of the peptides using liquid chromatography tandem mass spectrometry (LC-MS/MS). At least one of the plurality of peptides has an amino acid sequence of SEQ ID NOS: 1-212, as shown in the Sequence Listing, which are hereby incorporated by reference in their entireties.

In some embodiments, two or more of the above allergens are detected and/or quantified by detecting, via LC-MS/MS, multiple peptides such as those discussed above, where for each peptide fragment multiple MRM transitions, such as those discussed above, are monitored. It has been discovered that accurate identification and/or quantification of allergens (e.g., egg proteins such as ovalbumin, lysozyme or milk proteins such as casein and lactoglobulin, high and low glutenins, proteins obtained from wheat, rye, oats, barley, mustard, sesame and various nuts) can be achieved by monitoring and quantifying at least one and preferably several (e.g., all) of a set of specific peptides of the allergen (such as those disclosed herein) and specific MRM transitions for each peptide (such as those disclosed herein) using LC-MS/MS.

In one embodiment, at least one selected MRM transition can be monitored for each of the plurality of peptides. For example, two, three, or any other number of MRM transitions can be monitored for each of said peptides. In one embodiment, two or more allergens can be detected and/or quantified, for example, using the same run of a tandem mass spectrometer. In another embodiment, the amount of two or more peptides is determined to quantify the allergen of interest.

In some embodiments, the method can comprise adding a known amount of at least one of ovalbumin, lysozyme, casein, lactoglobulin, high and low glutenins, proteins from wheat, rye, oats, barley, mustard, sesame, macadamia nuts, pistachio, brazil, walnuts, peanuts and hazelnuts prior to digesting the sample. For example, a known amount of each of ovalbumin, lysozyme, casein, and lactoglobulin can be added to the sample prior to digesting the sample.

Also disclosed herein is a method of detecting ovalbumin in a sample. The method can include adding a proteolytic enzyme (e.g., trypsin) to the sample to lyse at least a portion of the ovalbumin present in the sample, if any, into a plurality of peptides having at least one peptide having an amino acid sequence of SEQ ID NOS: 1-7. Liquid chromatography tandem mass spectrometry (LC-MS/MS) is then utilized to determine whether the at least one peptide is in the sample.

In one aspect, selected MRM transitions can be monitored to detect and/or quantify selected peptides of the ovalbumin. For example, one selected precursor-product ion pair transitions can be monitored. Optimized MRM transitions for each of the peptides corresponding to SEQ ID NOS: 1-7 are provided below in Table 1. Any number of the optimized transitions for peptides of ovalbumin can be monitored via LC-MS/MS. For example, one, two, three, or optionally, all of the optimized MRM transitions can be monitored.

Also disclosed herein is a method of detecting lysozyme in a sample. The method can include adding a proteolytic enzyme (e.g., trypsin) to the sample to lyse at least a portion of the lysozyme present in the sample, if any, into a plurality of peptides having at least one peptide having an amino acid sequence of SEQ ID NOS: 8-11. Liquid chromatography tandem mass spectrometry (LC-MS/MS) is then utilized to determine whether the at least one peptide is in the sample.

In one aspect, selected MRM transitions can be monitored to detect or quantify selected peptides of the lysozyme. For example, selected precursor-product ion pair transitions can be monitored. Optimized MRM transitions for each of the peptides corresponding to SEQ ID NOS: 8-11 are provided below in Table 2. Any number of the optimized transitions for peptides of lysozyme can be monitored via LC-MS/MS. For example, one, two, three, or optionally, all of the optimized MRM transitions can be monitored.

Also disclosed herein is a method of detecting casein (e.g., casein isoform S1 or S2) in a sample. In one embodiment, the method can include adding a proteolytic enzyme (e.g., trypsin) to the sample to lyse at least a portion of the casein isoform S1 present in the sample, if any, into a plurality of peptides having at least one peptide having an amino acid sequence of SEQ ID NOS: 12-18. In another embodiment, the method can include adding a proteolytic enzyme to the sample to lyse at least a portion of the casein isoform S2 present in the sample, if any, into a plurality of peptides having at least one peptide having an amino acid sequence of SEQ ID NOS: 19-23. Liquid chromatography tandem mass spectrometry (LC-MS/MS) is then utilized to determine whether the at least one peptide is in the sample.

In one aspect, selected MRM transitions can be monitored to detect or quantify selected peptides of the casein. For example, selected precursor-product ion pair transitions can be monitored. Optimized MRM transitions for each of the peptides corresponding to SEQ ID NOS: 12-23 are provided below in Tables 3 or 4. Any number of the optimized transitions for peptides of casein can be monitored via LC-MS/MS. For example, one, two, three, or optionally, all of the optimized MRM transitions can be monitored.

Also disclosed herein is a method of detecting lactoglobulin in a sample. The method can include adding a proteolytic enzyme (e.g., trypsin) to the sample to lyse at least a portion of the lactoglobulin present in the sample, if any, into a plurality of peptides having at least one peptide having an amino acid sequence of SEQ ID NOS: 24-29. Liquid chromatography tandem mass spectrometry (LC-MS/MS) is then utilized to determine whether the at least one peptide is in the sample.

In one aspect, selected MRM transitions can be monitored to detect or quantify selected peptides of the lactoglobulin. For example, selected precursor-product ion pair transitions can be monitored. Optimized MRM transitions for each of the peptides corresponding to SEQ ID NOS: 24-29 are provided below in Table 5. Any number of the optimized transitions for peptides of lactoglobulin can be monitored via LC-MS/MS. For example, one, two, three, or optionally, all of the optimized MRM transitions can be monitored.

Also disclosed herein is a method of detecting barley in a sample. The method can include adding a proteolytic enzyme (e.g., trypsin) to the sample to lyse at least a portion of the proteins of barley present in the sample, if any, into a plurality of peptides having at least one peptide having an amino acid sequence of SEQ ID NOS: 30-33. Liquid chromatography tandem mass spectrometry (LC-MS/MS) is then utilized to determine whether the at least one peptide is in the sample.

In one aspect, selected MRM transitions can be monitored to detect or quantify selected peptides of the barley proteins. For example, selected precursor-product ion pair transitions can be monitored. Optimized MRM transitions for each of the peptides corresponding to SEQ ID NOS: 30-33 are provided below in Table 6. Any number of the optimized transitions for peptides of barley can be monitored via LC-MS/MS. For example, one, two, three, or optionally, all of the optimized MRM transitions can be monitored.

Also disclosed herein is a method of detecting high and low molecular weight glutenins in a sample. In one embodiment, the method can include adding a proteolytic enzyme (e.g., trypsin) to the sample to lyse at least a portion of the high or low molecular weight glutenins present in the sample, if any, into a plurality of peptides having at least one peptide having an amino acid sequence of SEQ ID 34-79. Liquid chromatography tandem mass spectrometry (LC-MS/MS) is then utilized to determine whether the at least one peptide is in the sample.

In one aspect, selected MRM transitions can be monitored to detect or quantify selected peptides of the low or high molecular weight glutenins. For example, selected precursor-product ion pair transitions can be monitored. Optimized MRM transitions for each of the peptides corresponding to SEQ ID NOS: 34-79 are provided below in Tables 7 and 8. Any number of the optimized transitions for peptides of the high or low glutens can be monitored via LC-MS/MS. For example, one, two, three, or optionally, all of the optimized MRM transitions can be monitored for the high or low molecular weight glutenins.

Also disclosed herein is a method of detecting mustard in a sample. The method can include adding a proteolytic enzyme (e.g., trypsin) to the sample to lyse at least a portion of the mustard proteins present in the sample, if any, into a plurality of peptides having at least one peptide having an amino acid sequence of SEQ ID NOS: 80-112. Liquid chromatography tandem mass spectrometry (LC-MS/MS) is then utilized to determine whether the at least one peptide is in the sample.

In one aspect, selected MRM transitions can be monitored to detect or quantify selected peptides of the mustard proteins. For example, selected precursor-product ion pair transitions can be monitored. Optimized MRM transitions for each of the peptides corresponding to SEQ ID NOS: 80-112 are provided below in Table 9. Any number of the optimized transitions for peptides of mustard can be monitored via LC-MS/MS. For example, one, two, three, or optionally, all of the optimized MRM transitions can be monitored.

Also disclosed herein is a method of detecting oats in a sample. The method can include adding a proteolytic enzyme (e.g., trypsin) to the sample to lyse at least a portion of the oat proteins present in the sample, if any, into a plurality of peptides having at least one peptide having an amino acid sequence of SEQ ID NOS: 113-116. Liquid chromatography tandem mass spectrometry (LC-MS/MS) is then utilized to determine whether the at least one peptide is in the sample.

In one aspect, selected MRM transitions can be monitored to detect or quantify selected peptides of the oat proteins. For example, selected precursor-product ion pair transitions can be monitored. Optimized MRM transitions for each of the peptides corresponding to SEQ ID NOS: 113-116 are provided below in Table 10. Any number of the optimized transitions for peptides of oats can be monitored via LC-MS/MS. For example, one, two, three, or optionally, all of the optimized MRM transitions can be monitored.

Also disclosed herein is a method of detecting rye in a sample. The method can include adding a proteolytic enzyme (e.g., trypsin) to the sample to lyse at least a portion of the rye proteins present in the sample, if any, into a plurality of peptides having at least one peptide having an amino acid sequence of SEQ ID NOS: 117-123. Liquid chromatography tandem mass spectrometry (LC-MS/MS) is then utilized to determine whether the at least one peptide is in the sample.

In one aspect, selected MRM transitions can be monitored to detect or quantify selected peptides of the rye proteins. For example, selected precursor-product ion pair transitions can be monitored. Optimized MRM transitions for each of the peptides corresponding to SEQ ID NOS: 117-123 are provided below in Table 11. Any number of the optimized transitions for peptides of rye can be monitored via LC-MS/MS. For example, one, two, three, or optionally, all of the optimized MRM transitions can be monitored.

Also disclosed herein is a method of detecting sesame in a sample. The method can include adding a proteolytic enzyme (e.g., trypsin) to the sample to lyse at least a portion of the sesame proteins present in the sample, if any, into a plurality of peptides having at least one peptide having an amino acid sequence of SEQ ID NOS: 124-132. Liquid chromatography tandem mass spectrometry (LC-MS/MS) is then utilized to determine whether the at least one peptide is in the sample.

In one aspect, selected MRM transitions can be monitored to detect or quantify selected peptides of the sesame proteins. For example, selected precursor-product ion pair transitions can be monitored. Optimized MRM transitions for each of the peptides corresponding to SEQ ID NOS: 124-132 are provided below in Table 12. Any number of the optimized transitions for peptides of sesame can be monitored via LC-MS/MS. For example, one, two, three, or optionally, all of the optimized MRM transitions can be monitored.

Also disclosed herein is a method of detecting wheat in a sample. The method can include adding a proteolytic enzyme (e.g., trypsin) to the sample to lyse at least a portion of the wheat proteins present in the sample, if any, into a plurality of peptides having at least one peptide having an amino acid sequence of SEQ ID NOS: 133-138. Liquid chromatography tandem mass spectrometry (LC-MS/MS) is then utilized to determine whether the at least one peptide is in the sample.

In one aspect, selected MRM transitions can be monitored to detect or quantify selected peptides of the wheat proteins. For example, selected precursor-product ion pair transitions can be monitored. Optimized MRM transitions for each of the peptides corresponding to SEQ ID NOS: 133-138 are provided below in Table 13. Any number of the optimized transitions for peptides of wheat can be monitored via LC-MS/MS. For example, one, two, three, or optionally, all of the optimized MRM transitions can be monitored.

Also disclosed herein is a method of detecting brazil nuts in a sample. The method can include adding a proteolytic enzyme (e.g., trypsin) to the sample to lyse at least a portion of the brazil nut proteins present in the sample, if any, into a plurality of peptides having at least one peptide having an amino acid sequence of SEQ ID NOS: 139-155. Liquid chromatography tandem mass spectrometry (LC-MS/MS) is then utilized to determine whether the at least one peptide is in the sample.

In one aspect, selected MRM transitions can be monitored to detect or quantify selected peptides of the brazil nut proteins. For example, selected precursor-product ion pair transitions can be monitored. Optimized MRM transitions for each of the peptides corresponding to SEQ ID NOS: 139-155 are provided below in Table 14. Any number of the optimized transitions for peptides of brazil nuts can be monitored via LC-MS/MS. For example, one, two, three, or optionally, all of the optimized MRM transitions can be monitored.

Also disclosed herein is a method of detecting hazelnuts in a sample. The method can include adding a proteolytic enzyme (e.g., trypsin) to the sample to lyse at least a portion of the hazelnut proteins present in the sample, if any, into a plurality of peptides having at least one peptide having an amino acid sequence of SEQ ID NOS: 156-172. Liquid chromatography tandem mass spectrometry (LC-MS/MS) is then utilized to determine whether the at least one peptide is in the sample.

In one aspect, selected MRM transitions can be monitored to detect or quantify selected peptides of the hazelnut proteins. For example, selected precursor-product ion pair transitions can be monitored. Optimized MRM transitions for each of the peptides corresponding to SEQ ID NOS: 156-172 are provided below in Table 15. Any number of the optimized transitions for peptides of hazelnuts can be monitored via LC-MS/MS. For example, one, two, three, or optionally, all of the optimized MRM transitions can be monitored.

Also disclosed herein is a method of detecting macadamia nuts in a sample. The method can include adding a proteolytic enzyme (e.g., trypsin) to the sample to lyse at least a portion of the macadamia nut proteins present in the sample, if any, into a plurality of peptides having at least one peptide having an amino acid sequence of SEQ ID NOS: 173-181. Liquid chromatography tandem mass spectrometry (LC-MS/MS) is then utilized to determine whether the at least one peptide is in the sample.

In one aspect, selected MRM transitions can be monitored to detect or quantify selected peptides of the macadamia nut proteins. For example, selected precursor-product ion pair transitions can be monitored. Optimized MRM transitions for each of the peptides corresponding to SEQ ID NOS: 173-181 are provided below in Table 16. Any number of the optimized transitions for peptides of macadamia nuts can be monitored via LC-MS/MS. For example, one, two, three, or optionally, all of the optimized MRM transitions can be monitored.

Also disclosed herein is a method of detecting peanuts in a sample. The method can include adding a proteolytic enzyme (e.g., trypsin) to the sample to lyse at least a portion of the peanut proteins present in the sample, if any, into a plurality of peptides having at least one peptide having an amino acid sequence of SEQ ID NOS: 182-187. Liquid chromatography tandem mass spectrometry (LC-MS/MS) is then utilized to determine whether the at least one peptide is in the sample.

In one aspect, selected MRM transitions can be monitored to detect or quantify selected peptides of the peanut proteins. For example, selected precursor-product ion pair transitions can be monitored. Optimized MRM transitions for each of the peptides corresponding to SEQ ID NOS: 182-187 are provided below in Table 17. Any number of the optimized transitions for peptides of peanuts can be monitored via LC-MS/MS. For example, one, two, three, or optionally, all of the optimized MRM transitions can be monitored.

Also disclosed herein is a method of detecting pistachio nuts in a sample. The method can include adding a proteolytic enzyme (e.g., trypsin) to the sample to lyse at least a portion of the pistachio nut proteins present in the sample, if any, into a plurality of peptides having at least one peptide having an amino acid sequence of SEQ ID NOS: 188-203. Liquid chromatography tandem mass spectrometry (LC-MS/MS) is then utilized to determine whether the at least one peptide is in the sample.

In one aspect, selected MRM transitions can be monitored to detect or quantify selected peptides of the pistachio nut proteins. For example, selected precursor-product ion pair transitions can be monitored. Optimized MRM transitions for each of the peptides corresponding to SEQ ID NOS: 188-203 are provided below in Table 18. Any number of the optimized transitions for peptides of pistachio nuts can be monitored via LC-MS/MS. For example, one, two, three, or optionally, all of the optimized MRM transitions can be monitored.

Also disclosed herein is a method of detecting walnuts in a sample. The method can include adding a proteolytic enzyme (e.g., trypsin) to the sample to lyse at least a portion of the brazil nut proteins present in the sample, if any, into a plurality of peptides having at least one peptide having an amino acid sequence of SEQ ID NOS: 203-212. Liquid chromatography tandem mass spectrometry (LC-MS/MS) is then utilized to determine whether the at least one peptide is in the sample.

In one aspect, selected MRM transitions can be monitored to detect or quantify selected peptides of the walnut proteins. For example, selected precursor-product ion pair transitions can be monitored. Optimized MRM transitions for each of the peptides corresponding to SEQ ID NOS: 203-212 are provided below in Table 19. Any number of the optimized transitions for peptides of walnuts can be monitored via LC-MS/MS. For example, one, two, three, or optionally, all of the optimized MRM transitions can be monitored.

In some embodiments, the above methods can utilize at least one isotopically-enriched peptide having the same amino acid sequence as that of the selected peptide to calibrate the quantitation of that peptide. In some embodiments, a standard having a known concentration of a selected peptide can be utilized to calibrate the quantitation of the selected peptide. In some embodiments, a known amount of the allergen of interest (e.g., ovalbumin, lysozyme, casein, lactoglobulin, high and low glutenins or proteins from wheat, rye, oats, barley, mustard, sesame and various nuts including macadamia, pistachio, brazil, walnuts, peanuts and hazelnuts) can be added to the sample prior to adding the proteolytic enzyme to calibrate the quantitation of the selected peptide and/or protein of interest. In some embodiments, a known amount of each of ovalbumin, lysozyme, casein, lactoglobulin, high and low glutenins, proteins from wheat, rye, oats, barley, mustard, sesame and various nuts including macadamia, pistachio, brazil, walnuts, peanuts and hazelnuts can be added to the sample prior to adding the proteolytic enzyme.

The sample can be from a variety of sources. In one embodiment, for example, the sample can be a food sample.

In another embodiment, the method comprises monitoring at least one precursor-product ion pair transition with specified m/z value associated with a specific amino acid sequence selected from the group consisting of: i) SEQ ID NO: 113, m/z value of about 989/998, 989/1085, or 989/1234; ii) SEQ ID NO: 114, m/z value of about 777/984, 777/1112, or 777/1226; iii) SEQ ID NO: 115, m/z value of about 627/642, or 627/1013; iv) SEQ ID NO: 116, m/z value of about 419/642.

In yet another embodiment, the method comprises monitoring at least one precursor-product ion pair transition with specified m/z value associated with a specific amino acid sequence selected from the group consisting of: i) SEQ ID NO: 124, m/z value of about 465/472, 465/728, or 465/815; ii) SEQ ID NO: 125, m/z value of about 397/679, 397/417, or 397/580; iii) SEQ ID NO: 126, m/z value of about 717/743, 717/957 or 717/372; iv) SEQ ID NO: 127, m/z value of about 380/589, 380/476, or 380/377; v) SEQ ID NO: 128, m/z value of about 419/522, 419/637, or 419/409; vi) SEQ ID NO: 129, m/z value of about 582/795, 582/866, or 582/980; vii) SEQ ID NO: 130, m/z value of about 806/869, 806/1070, or 806/957; viii) SEQ ID NO: 132, m/z value of about 685/901, 685/1089, or 685/1238.

In yet another embodiment, the method comprises monitoring at least one precursor-product ion pair transition with specified m/z value associated with a specific amino acid sequence selected from the group consisting of: i) SEQ ID NO: 156, m/z value of about 582/666, 582/852, or 582/999; ii) SEQ ID NO: 157, m/z value of about 514/729, 514/800, or 514/914; iii) SEQ ID NO: 158, m/z value of about 882/1033, 882/580, or 882/806; iv) SEQ ID NO: 159, m/z value of about 567/449, 567/684, or 567/799; v) SEQ ID NO: 160, m/z value of about 539/763, 539/948, or 539/635; vi) SEQ ID NO: 161, m/z value of about 374/619, 374/490, or 374/304; vii) SEQ ID NO: 162, m/z value of about 576/689, 576/852, or 576/588; viii) SEQ ID NO: 163, m/z value of about 721/900, 721/1014, or 721/484; ix) SEQ ID NO: 164, m/z value of about 502/703, 502/816, or 502/575; x) SEQ ID NO: 165, m/z value of about 807/874, 807/988, or 807/1089; xi) SEQ ID NO: 166, m/z value of about 700/984, 700/464, or 700/365; xii) SEQ ID NO: 167, m/z value of about 679/841, 679/600, or 679/713; xiii) SEQ ID NO: 168, m/z value of about 815/906, 815/835, or 815/724; xiv) SEQ ID NO: 169, m/z value of about 424/589, 424/718, or 424/488; xv) SEQ ID NO: 170, m/z value of about 601/973, 601/616, or 601/731; xvi) SEQ ID NO: 171, m/z value of about 791/935, or 791/1212; and xvii) SEQ ID NO: 172, m/z value of about 528/614.

In yet another embodiment, the method comprises monitoring at least one precursor-product ion pair transition with specified m/z value associated with a specific amino acid sequence selected from the group consisting of: i) SEQ ID NO: 173, m/z value of about 729/921, or 729/1050; ii) SEQ ID NO: 174, m/z value of about 438/626, or 438/725; iii) SEQ ID NO: 175, m/z value of about 585/892, or 585/763; iv) SEQ ID NO: 176, m/z value of about 545/821, or 545/952; v) SEQ ID NO: 177, m/z value of about 537/786, or 537/935; vi) SEQ ID NO: 178, m/z value of about 493/743, or 493/580; vii) SEQ ID NO: 179, m/z value of about 344/500, or 344/401; viii) SEQ ID NO: 180, m/z value of about 392/566, or 392/437; and ix) SEQ ID NO: 181, m/z value of about 500/743, or 500/580.

In yet another embodiment, the method comprises monitoring at least one precursor-product ion pair transition with specified m/z value associated with a specific amino acid sequence selected from the group consisting of: i) SEQ ID NO: 188, m/z value of about 397/515, 397/572, or 397/416; ii) SEQ ID NO: 189, m/z value of about 518/556, or 518/797; iii) SEQ ID NO: 190, m/z value of about 802/1078, 802/802, or 802/931; iv) SEQ ID NO: 191, m/z value of about 746/1157, 746/941, or 746/683; v) SEQ ID NO: 192, m/z value of about 569/821, 569/557, 569/658; vi) SEQ ID NO: 193, m/z value of about 713/1012, or 713/470; vii) SEQ ID NO: 194, m/z value of about 502/703, 502/816, or 502/575; viii) SEQ ID NO: 195, m/z value of about 479/680, 479/809, or 479/381; ix) SEQ ID NO: 196, m/z value of about 702/790, 702/904, or 702/1088; x) SEQ ID NO: 197, m/z value of about 838/1020, 838/835, or 838/906; xi) SEQ ID NO: 198, m/z value of about 961/1027, 961/899, or 961/671; xii) SEQ ID NO: 199, m/z value of about 790/1054, 790/492, or 790/925; xiii) SEQ ID NO: 200, m/z value of about 777/694, 777/807, or 777/579; xiv) SEQ ID NO: 201, m/z value of about 279/500, or 279/274; xv) SEQ ID NO: 202, m/z value of about 837/1080, 837/966, 837/753; and xvi) SEQ ID NO: 203, m/z value of about 598/747, 598/848, 598/634.

In yet another embodiment, the method comprises monitoring at least one precursor-product ion pair transition with specified m/z value associated with a specific amino acid sequence selected from the group consisting of: i) SEQ ID NO: 204, m/z value of about 813/1142; ii) SEQ ID NO: 205, m/z value of about 805/900, 805/623, or 805/345; iii) SEQ ID NO: 206, m/z value of about 698/820, 698/949, or 698/461; iv) SEQ ID NO: 207, m/z value of about 683/1136, 683/796, 683/925, 683/1039, or 683/569; v) SEQ ID NO: 208, m/z value of about 515/729, 515/487, or 515/616; vi) SEQ ID NO: 209, m/z value of about 955/692, 955/905, or 955/577; vii) SEQ ID NO: 210, m/z value of about 502/703, 502/816, or 502/575; viii) SEQ ID NO: 211, m/z value of about 792/904, or 792/1017; ix) SEQ ID NO: 212, m/z value of about 529/1017;

Also disclosed herein is a kit for use in the mass spectrometric testing of a sample for an allergen. The kit can include at least one proteolytic enzyme (e.g., trypsin) for fragmenting at least one allergen present in the sample, if any, into a plurality of peptides. The allergen can be, for example, ovalbumin, lysozyme, casein, lactoglobulin, high and low molecular weight glutenins, proteins from wheat, rye, oats, barley, mustard, sesame and various nuts including macadamia, pistachio, brazil, walnuts, peanuts and hazelnuts and the at least one of the plurality of peptides can be a peptide having an amino acid sequence of SEQ ID NO: 1-212. The kit can also include at least one reagent for quantifying at least one of said plurality of peptides using a mass spectrometer.

In one aspect, the reagent for quantifying at least one of the plurality of peptides can be an isotopically-enriched peptide having the same amino acid sequence as that of one of the plurality of peptides. In one embodiment, the isotopically-enriched peptide can include, for example, at least one of C13 or N15. In another aspect, the reagent for quantifying at least one said plurality of peptides can include a selected concentration of at least one of the plurality of peptides for calibrating the mass spectrometer. In some embodiments, the reagent for quantifying at least one said plurality of peptides can comprise at least one of ovalbumin, lysozyme, casein, lactoglobulin, high or low molecular weight glutenins, proteins from wheat, rye, oats, barley, mustard, sesame and various nuts including macadamia, pistachio, brazil, walnuts, peanuts and hazelnuts for calibrating the mass spectrometer. For example, the kit can include a known amount of each of ovalbumin, lysozyme, casein, lactoglobulin, high or low molecular weight glutenins, proteins from wheat, rye, oats, barley, mustard, sesame and various nuts including macadamia, pistachio, brazil, walnuts, peanuts and hazelnuts. In other embodiments, only some of the allergens are included.

The kit can additionally include various agents used in preparing a sample to be analyzed using a mass spectrometer, running the prepared sample through a LC column, or performing mass spectrometry. By way of non-limiting example, the kit can include one of ovalbumin, lysozyme, casein, lactoglobulin, high or low glutenins, proteins from wheat, rye, oats, barley, mustard, sesame and various nuts including macadamia, pistachio, brazil, walnuts, peanuts and hazelnuts to be used as a standard, for example. The kit can also include an alkylating agent (e.g., Methyl methanethiosulfonate (MMTS), iodoacetamide) and/or a reducing agent.

In one aspect, the kit can include instructions for quantifying the at least one allergen using a mass spectrometer. By way of example, the kit can include information pertaining to transition pairs to be used as settings in a mass spectrometer or the fragment ions that are expected.

According to various aspects, software is provided which can control the processes and/or perform the calculations described herein. For example, the software can provide instructions to a mass spectrometer to monitor one or more specific precursor-product ion pair transitions or fragment ions.

DETAILED DESCRIPTION

Those skilled in the art will understand that the methods and kits described herein are non-limiting exemplary embodiments and that the scope of the applicants' disclosure is defined solely by the claims. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art. The features illustrated or described in connection with one exemplary embodiment may be combined with the features of other embodiments. Such modifications and variations are intended to be included within the scope of the applicants' disclosure.

According to various embodiments, methods are provided for screening a sample for the presence or quantity of ovalbumin, lysozyme, casein (isoform S1 and S2), lactoglobulin, high or low glutenins, and proteins from wheat, rye, oats, barley, mustard, sesame and various nuts including macadamia, pistachio, brazil, walnuts, peanuts and hazelnuts using mass spectrometry by detecting one or more amino acid sequences specific to the allergen of interest. For example, allergen-specific peptides can be detected using Liquid Chromatography-Tandem Mass Spectrometry (LC-MS/MS). Selected MRM transitions can be observed for each peptide to enable quantitation of the allergen in the sample.

The methods can utilize a variety of mass spectrometry techniques known in the art. For example, the mass spectrometry technique can be a tandem mass spectrometry (MS/MS) technique and/or a liquid chromatography tandem mass spectrometry (LC-MS/MS) technique. In some embodiments, the technique comprises an LC-MS/MS technique and the use of a triple quadrupole instrument and Multiple Reaction Monitoring (MRM).

According to some embodiments, the method can comprise detecting and/or quantifying ovalbumin in the sample by detecting at least one isolated peptide specific to ovalbumin, for example, one or more of the peptides having an amino acid sequence of SEQ ID NOS: 1-7 identified herein. For example, LC-MS/MS can be used to determine the presence and/or quantity of ovalbumin-specific peptides in the sample. In one exemplary embodiment, a triple quadrupole mass spectrometer can be used to monitor selected Multiple Reaction Monitoring (MRM) transitions. In some embodiments, the ovalbumin-specific peptide can have the amino acid sequence of SEQ ID NO: 1 identified herein, and the method can include monitoring at least one precursor-product ion pair transition having an m/z value of about 391/504, 391/667, or 391/433, wherein the term "about" as used herein means within a range of +/− one (1) atomic mass unit. In other embodiments, the ovalbumin-specific peptide can have the amino acid sequence of SEQ ID NO: 2 identified herein, and the method can include monitoring at least one precursor-product ion pair transition having an m/z value of about 762/1036, 762/487, 762/1150. In other embodiments, the ovalbumin-specific peptide can have the amino acid sequence of SEQ ID NO: 3 identified herein, and the method can include monitoring at least one precursor-product ion pair transition having an m/z value of about 605/419, 605/621, or 605,749. In other embodiments, the ovalbumin-specific peptide can have the amino acid sequence of SEQ ID NO: 4, and the method can include monitoring at least one precursor-product ion pair transition having an m/z value of about 673/1096, 673/1024, 673/1209, 449/526, 449/608, or 449/639. In other embodiments, the ovalbumin-specific peptide can have the amino acid sequence of SEQ ID NO: 5 identified herein, and the method can include monitoring at least one precursor-product ion pair transition having an m/z value of about 791/1052, 791/951, or 791/1239. In other embodiments, the ovalbumin-specific peptide can have the amino acid sequence of SEQ ID NO: 6 identified herein, and the method can include monitoring at least one precursor-product ion pair transition having an m/z value of about 844/666, 844/1332, or 844/1121. In other embodiments, the ovalbumin-specific peptide can have the amino acid sequence of SEQ ID NO: 7, and the method can include monitoring at least one precursor-product ion pair transition having an m/z value of about 930/1017, 930/1118, 930/1303, or 930/888.

In one exemplary embodiment, the method can include monitoring multiple precursor-product ion pair transitions associated with each ovalbumin-specific peptide. By way of example, the ovalbumin-specific peptide having the amino acid sequence of SEQ ID NO: 1 can be identified by monitoring any two of the precursor-product ion pair transitions having an m/z value of about 391/504, 391/667, or 391/433. In one embodiment, all three of the identified precursor-product ion pairs can be monitored.

In one embodiment, the method for detecting or quantifying ovalbumin in the sample can include detecting multiple ovalbumin-specific peptides. By way of non-limiting example, ovalbumin can be quantified by using any combination, or all, of the peptides having the amino acid sequences of SEQ ID NOS: 1-7 identified herein. As discussed above, for each peptide, one or more of the precursor-product ion pair transitions can be monitored.

Table 1 below shows sequences SEQ ID NOS: 1-7 of the peptides determined, according to applicants' teachings, to be specific to ovalbumin, along with their optimal MRM Q1, Q3 transitions. According to various embodiments, these observed peptides and transitions can be used to enable a reliable quantitation of the ovalbumin present in the sample. Additional MRM transitions specific to ovalbumin are shown in Appendix A, B, and D, which are hereby incorporated by reference in their entireties.

In the following tables the Fragment Ion has a reference to the charge as well as the conventional fragmentation nomenclature. For example, the label of 2y4 would indicate a fragment that is doubly charged and is the y4 fragment (four units from the C-terminus). Likewise a label of 2b4 would indicate a fragment that is doubly charged and is the b4 fragment (four units from the N-terminus). These nomenclature rules are known to those skilled in the art.

TABLE 1

| Ovalbumin (Chicken) | Q1 | Q3 | Fragment Ion |
|---|---|---|---|
| LYAEER | 391.1 | 504.3 | 2y4 |
| (SEQ ID NO: 1) | 391.1 | 667.4 | 2y5 |
| doubly-charged | 391.1 | 433.2 | 2y3 |
| YPILPEYLQCVK | 762.3 | 1036.7 | 2y8 |
| (SEQ ID NO: 2) | 762.3 | 487.4 | 2b4 |
| doubly-charged | 762.3 | 1149.9 | 2y9 |
| DEDTQAMPFR | 605.7 | 419.3 | 2y3 |
| (SEQ ID NO: 3) | 605.7 | 621.6 | 2y5 |
| doubly-charged | 605.7 | 749.5 | 2y6 |
| HIATNAVLFFGR | 673.5 | 1095.9 | 2y10 |
| (SEQ ID NO: 4) | 673.5 | 1024.7 | 2y9 |
| doubly-charged | 673.5 | 1209 | 2y11 |
| HIATNAVLFFGR | 449.2 | 526.5 | 2y10 |
| (SEQ ID NO: 4) | 449.2 | 608.5 | 2y9 |
| triply-charged | 449.2 | 639.5 | 2y11 |

TABLE 1-continued

| Ovalbumin (Chicken) | Q1 | Q3 | Fragment Ion |
|---|---|---|---|
| LTEWTSSNVMEER | 791.7 | 1052.7 | 2y10 |
| (SEQ ID NO: 5) | 791.7 | 951.6 | 2y9 |
| doubly-charged | 791.7 | 1238.8 | 2y11 |
| GGLEPINFQTAADQAR | 844.6 | 666.7 | 2y10 |
| (SEQ ID NO: 6) | 844.6 | 1331.9 | 2y9 |
| doubly-charged | 844.6 | 1121.6 | 2y11 |
| ELINSWVESQTNGIIR | 930.5 | 1017.5 | 2y12d |
| (SEQ ID NO: 7) | 930.5 | 1117.8 | 2y11 |
| doubly-charged | 930.5 | 1302.9 | 2y10 |
|  | 930 | 888.5 |  |

According to some embodiments, the method can comprise detecting and/or quantifying lysozyme in the sample by detecting at least one isolated peptide specific to lysozyme, for example, one or more of the peptides having an amino acid sequence of SEQ ID NOS: 8-11 identified herein. For example, a triple quadrupole mass spectrometer can be used to monitor selected Multiple Reaction Monitoring (MRM) transitions to determine the presence and/or quantity of lysozyme-specific peptides in the sample. In some embodiments, the lysozyme-specific peptide can have the amino acid sequence of SEQ ID NO: 8 identified herein, and the method can include monitoring at least one precursor-product ion pair transition having an m/z value of about 438/737, 438/452, or 438/680. In other embodiments, the lysozyme-specific peptide can have the amino acid sequence of SEQ ID NO: 9 identified herein, and the method can include monitoring at least one precursor-product ion pair transition having an m/z value of about 497/621, 497/847, or 497/807. In other embodiments, the lysozyme-specific peptide can have the amino acid sequence of SEQ ID NO: 10 identified herein, and the method can include monitoring at least one precursor-product ion pair transition having an m/z value of about 715/804, 715/951, or 715/1065. In other embodiments, the lysozyme-specific peptide can have the amino acid sequence of SEQ ID NO: 11, and the method can include monitoring at least one precursor-product ion pair transition having an m/z value of about 878/901, 878/1064, or 878/1178.

In one exemplary embodiment, the method can include monitoring multiple precursor-product ion pair transitions associated with each lysozyme-specific peptide. By way of example, the lysozyme-specific peptide having the amino acid sequence of SEQ ID NO: 8 can be identified by monitoring any two of the precursor-product ion pair transitions having an m/z value of about 438/737, 438/452, or 438/680. In one embodiment, all three of the identified precursor-product ion pairs can be monitored.

In one embodiment, the method for detecting or quantifying lysozyme in the sample can include detecting multiple lysozyme-specific peptides. By way of non-limiting example, lysozyme can be quantified by using any combination, or all, of the peptides having the amino acid sequences of SEQ ID NOS: 8-11 identified herein. As discussed above, for each peptide, one or more of the precursor-product ion pair transitions can be monitored.

Table 2 below shows sequences SEQ ID NOS: 8-11 of the peptides determined, according to the present teachings, to be specific to lysozyme, along with their optimal MRM Q1, Q3 transitions. According to various embodiments, these observed peptides and transitions can be used to enable a reliable quantitation of the lysozyme present in the sample. Additional MRM transitions specific to lysozyme are shown in Appendix A, B, and D, which are hereby incorporated by reference in their entireties.

TABLE 2

| Lysozyme (Chicken) | Q1 | Q3 | Fragment Ion |
|---|---|---|---|
| HGLDNYR | 438 | 737.5 | 2y6 |
| (SEQ ID NO: 8) | 438 | 452.3 | 2y3 |
| doubly-charged | 438 | 680.3 | 2y5 |
| WWCNDGR | 497.6 | 621.4 | 2y5 |
| (SEQ ID NO: 9) | 497.6 | 847.5 |  |
| doubly-charged | 497.6 | 807.5 | 2y6 |
| FESNFNTQATNR | 715 | 804.7 | 2y7 |
| (SEQ ID NO: 10) | 715 | 951.6 | 2y8 |
| doubly-charged | 715 | 1065.7 | 2y9 |
| NTDGSTDYGILQINSR | 878 | 901 | 2y8 |
| SEQ ID NO: 11) | 878 | 1064.3 | 2y9 |
| doubly-charged | 878 | 1178.7 | 2y10 |

According to some embodiments, the method can comprise detecting and/or quantifying the casein in the sample by detecting at least one isolated peptide specific to casein, for example, one or more of the peptides having an amino acid sequence of SEQ ID NOS: 12-23 identified herein. For example, the method can comprise detecting or quantifying the S1 isoform of casein in the sample by detecting an isolated peptide specific to casein S1, e.g., one or more of the peptides having am amino acid sequence of SEQ ID NOS: 12-18 identified herein. By way of example, a triple quadrupole mass spectrometer can be used to monitor selected Multiple Reaction Monitoring (MRM) transitions to determine the presence and/or quantity of casein S1-specific peptides in the sample. In some embodiments, the casein S1-specific peptide can have the amino acid sequence of SEQ ID NO: 12 identified herein, and the method can include monitoring at least one precursor-product ion pair transition having an m/z value of about 693/921, 693/992, or 693/1091. In other embodiments, the casein S1-specific peptide can have the amino acid sequence of SEQ ID NO: 13 identified herein, and the method can include monitoring at least one precursor-product ion pair transition having an m/z value of about 584/763, 584/706, 584/650, or 438/600. In other embodiments, the casein S1-specific peptide can have the amino acid sequence of SEQ ID NO: 14 identified herein, and the method can include monitoring at least one precursor-product ion pair transition having an m/z value of about 416/488, 416/587, or 416/702. In other embodiments, the casein S1-specific peptide can have the amino acid sequence of SEQ ID NO: 15, and the method can include monitoring at least one precursor-product ion pair transition having an m/z value of about 634/992, 634/771, or 634/934. In other embodiments, the casein S1-specific peptide can have the amino acid sequence of SEQ ID NO: 16 identified herein, and the method can include monitoring at least one precursor-product ion pair transition having an m/z value of about 880/1325, 880/1495, 880/1438, 880/436, 587/758, 587/871, or 587/790. In other embodiments, the casein S1-specific peptide can have the amino acid sequence of SEQ ID NO: 17 identified herein, and the method can include monitoring at least one precursor-product ion pair transition having an m/z value of about 345/590, 345/476, or 345/573. In other embodiments, the casein S1-specific peptide can have the amino acid sequence of SEQ ID NO: 18, and the method can include monitoring at least one precursor-product ion pair transition having an m/z value of about 416/488, 416/587, or 416/702.

In one exemplary embodiment, the method can include monitoring multiple precursor-product ion pair transitions associated with each casein S1-specific peptide. By way of example, the casein S1-specific peptide having the amino acid sequence of SEQ ID NO: 12 can be identified by monitoring any two of the precursor-product ion pair transitions having an m/z value of about 693/921, 693/992, or 693/1091. In one embodiment, all three of the identified precursor-product ion pairs can be monitored.

In one embodiment, the method for detecting or quantifying the S1 isoform of casein in the sample can include detecting multiple casein S1-specific peptides. By way of non-limiting example, casein S1 can be quantified by using any combination, or all, of the peptides having the amino acid sequences of SEQ ID NOS: 12-18 identified herein. As discussed above, for each peptide, one or more of the precursor-product ion pair transitions can be monitored.

Table 3 below shows sequences SEQ ID NOS: 12-18 of the peptides determined, according to the applicants' teachings, to be specific to the S1 isoform of casein, along with their optimal MRM Q1, Q3 transitions. According to various embodiments, these observed peptides and transitions can be used to enable a reliable quantitation of the S1 isoform of casein present in the sample. Additional MRM transitions specific to the S1 isoform of casein are shown in Appendix A, B, and D, which are hereby incorporated by reference in their entireties.

TABLE 3

| Casein S1 (Bovine) | Q1 | Q3 | Fragment Ion |
|---|---|---|---|
| FFVAPFPEVFGK | 693.3 | 921.6 | 2y8 |
| (SEQ ID NO: 12) | 693.3 | 991.9 | 2y9 |
| doubly-charged | 693.3 | 1091.5 | 2y10 |
| LLILTCLVAVALARPK | 584.4 | 763.5 | 3y14d |
| (SEQ ID NO: 13) | 584.4 | 706.3 | 3y13d |
| triply-charged | 584.4 | 650.4 | 3y12d |
| LLILTCLVAVALARPK | 438 | 599.9 | 4y11d |
| (SEQ ID NO: 13) | | | |
| quadrupally-charged | | | |
| EDVPSER | 416.4 | 488.3 | 2y4 |
| (SEQ ID NO: 14) | 416.4 | 587.4 | 2y5 |
| doubly-charged | 416.4 | 702.7 | 2y6 |
| YLGYLEQLLR | 634.5 | 991.8 | 2y8 |
| (SEQ ID NO: 15) | 634.5 | 771.7 | 2y6 |
| doubly-charged | 634.5 | 934.9 | 2y7 |
| HQGLPQEVLNENLLR | 880.6 | 1325 | 2y11 |
| (SEQ ID NO: 16) | 880.6 | 1495 | 2y13 |
| doubly-charged | 880.6 | 1438 | 2y12 |
| | 880.5 | 436.2 | |
| HQGLPQEVLNENLLR | 587.3 | 758.4 | |
| (SEQ ID NO: 16) | 587.3 | 871.5 | |
| triply-charged | 587.3 | 790.4 | |
| VNELSK | 345.3 | 590.5 | 2y5 |
| (SEQ ID NO: 17) | 345.3 | 476.3 | 2y4 |
| doubly-charged | 345.3 | 573.3 | 2y5w |
| EDVPSER | 416.4 | 488.3 | 2y4 |
| (SEQ ID NO: 18) | 416.4 | 587.4 | 2y5 |
| doubly-charged | 416.4 | 702.7 | 2y6 |

According to some embodiments, the method can comprise detecting and/or quantifying the S2 isoform of casein in the sample by detecting at least one isolated peptide specific to casein S2, e.g., one or more of the peptides having an amino acid sequence of SEQ ID NOS: 19-23 identified herein. By way of example, a triple quadrupole mass spectrometer can be used to monitor selected Multiple Reaction Monitoring (MRM) transitions to determine the presence and/or quantity of casein S1-specific peptides in the sample. In some embodiments, the casein S2-specific peptide can have the amino acid sequence of SEQ ID NO: 19 identified herein, and the method can include monitoring at least one precursor-product ion pair transition having an m/z value of about 373/534 or 373/437. In other embodiments, the casein S2-specific peptide can have the amino acid sequence of SEQ ID NO: 20 identified herein, and the method can include monitoring at least one precursor-product ion pair transition having an m/z value of about 598/912, 598/701, 598/814, 598/436. In other embodiments, the casein S2-specific peptide can have the amino acid sequence of SEQ ID NO: 21 identified herein, and the method can include monitoring at least one precursor-product ion pair transition having an m/z value of about 438/629, 438/558, or 438/445. In other embodiments, the casein S2-specific peptide can have the amino acid sequence of SEQ ID NO: 22, and the method can include monitoring at least one precursor-product ion pair transition having an m/z value of about 490/648, 490/761, 490/833. In other embodiments, the casein S2-specific peptide can have the amino acid sequence of SEQ ID NO: 23 identified herein, and the method can include monitoring at least one precursor-product ion pair transition having an m/z value of about 694/1187, 694/811, or 694/940.

In one exemplary embodiment, the method can include monitoring multiple precursor-product ion pair transitions associated with each casein S2-specific peptide. By way of example, the casein S2-specific peptide having the amino acid sequence of SEQ ID NO: 19 can be identified by monitoring both of the precursor-product ion pair transitions having an m/z value of about 373/534 or 373/437. With reference to the casein S2-specific peptide having the amino acid sequence of SEQ ID NO: 20, any two, three, or all of the identified precursor-product ion pairs having an m/z value of about 598/912, 598/701, 598/814, or 598/436 can be monitored.

In one embodiment, the method for detecting or quantifying the S2 isoform of casein in the sample can include detecting multiple casein S2-specific peptides. By way of non-limiting example, casein S2 can be quantified by using any combination, or all, of the peptides having the amino acid sequences of SEQ ID NOS: 19-23 identified herein. As discussed above, for each peptide, one or more of the precursor-product ion pair transitions can be monitored.

Table 4 below shows sequences SEQ ID NOS: 19-23 of the peptides determined, according to the applicants' teachings, to be specific to the S2 isoform of casein, along with their optimal MRM Q1, Q3 transitions. According to various embodiments, these observed peptides and transitions can be used to enable a reliable quantitation of the S2 isoform of casein present in the sample.

TABLE 4

| Casein S2 (Bovine) | Q1 | Q3 | Fragment Ion |
|---|---|---|---|
| VIPYVR | 373.7 | 534.4 | 2y4 |
| (SEQ ID NO: 19) | 373.7 | 437.3 | 2y3 |
| doubly-charged | | | |

TABLE 4-continued

| Casein S2 (Bovine) | Q1 | Q3 | Fragment Ion |
|---|---|---|---|
| NAVPITPTLNR | 598.5 | 911.8 | 2y8 |
| (SEQ ID NO: 20) | 598.5 | 701.6 | 2y6 |
| doubly-charged | 598.5 | 814.7 | 2y7 |
| | 598.3 | 436.2 | |
| NMAINPSK | 438 | 629.5 | 2y6 |
| (SEQ ID NO: 21) | 438 | 558.4 | 2y5 |
| doubly-charged | 438 | 445.4 | 2y4 |
| FALPQYLK | 490.3 | 648.5 | 2y5 |
| (SEQ ID NO: 22) | 490.3 | 761.7 | 2y6 |
| doubly-charged | 490.3 | 832.8 | 2y7 |
| TVDMESTEVFTK | 694 | 1186.9 | 2y10 |
| (SEQ ID NO: 23) | 694 | 811.6 | 2y7 |
| doubly-charged | 694 | 940.7 | 2y8 |

According to some embodiments, the method can comprise detecting and/or quantifying lactoglobulin in the sample by detecting at least one isolated peptide specific to lactoglobulin, for example, one or more of the peptides having am amino acid sequence of SEQ ID NOS: 24-29 identified herein. For example, a triple quadrupole mass spectrometer can be used to monitor selected Multiple Reaction Monitoring (MRM) transitions to determine the presence and/or quantity of lysozyme-specific peptides in the sample. In some embodiments, the lactoglobulin-specific peptide can have the amino acid sequence of SEQ ID NO: 24 identified herein, and the method can include monitoring at least one precursor-product ion pair transition having an m/z value of about 533/853, 533/754, or 533/641. In other embodiments, the lactoglobulin-specific peptide can have the amino acid sequence of SEQ ID NO: 25 identified herein, and the method can include monitoring at least one precursor-product ion pair transition having an m/z value of about 458/803, 458/688, or 458/504. In other embodiments, the lactoglobulin-specific peptide can have the amino acid sequence of SEQ ID NO: 26 identified herein, and the method can include monitoring at least one precursor-product ion pair transition having an m/z value of about 1158/1453, 1158/1581, 1158/1255, 772/1026, 772/977, or 772/912. In other embodiments, the lactoglobulin-specific peptide can have the amino acid sequence of SEQ ID NO: 27, and the method can include monitoring at least one precursor-product ion pair transition having an m/z value of about 623/573, 623/918, 623/819, 623/1047. In other embodiments, the lactoglobulin-specific peptide can have the amino acid sequence of SEQ ID NO: 28 identified herein, and the method can include monitoring at least one precursor-product ion pair transition having an m/z value of about 561/806, 561/935, or 561/692. In other embodiments, the lactoglobulin-specific peptide can have the amino acid sequence of SEQ ID NO: 29, and the method can include monitoring at least one precursor-product ion pair transition having an m/z value of about 419/653, 419/556, or 419/425.

In one exemplary embodiment, the method can include monitoring multiple precursor-product ion pair transitions associated with each lactoglobulin-specific peptide. By way of example, the lactoglobulin-specific peptide having the amino acid sequence of SEQ ID NO: 24 can be identified by monitoring any two of the precursor-product ion pair transitions having an m/z value of about 533/853, 533/754, or 533/641. In one embodiment, all three of the identified precursor-product ion pairs can be monitored.

In one embodiment, the method for detecting and/or quantifying lactoglobulin in the sample can include detecting multiple lactoglobulin-specific peptides. By way of non-limiting example, lactoglobulin can be quantified by using any combination, or even all, of the peptides having the amino acid sequences of SEQ ID NOS: 24-29 identified herein. As discussed above, for each peptide, one or more of the precursor-product ion pair transitions can be monitored.

Table 5 below shows sequences SEQ ID NOS: 24-29 of the peptides determined, according to the applicants' teachings, to be specific to lactoglobulin, along with their optimal MRM Q1, Q3 transitions. According to various embodiments, these observed peptides and transitions can be used to enable a reliable quantitation of the lactoglobulin present in the sample. Additional MRM transitions specific to lactoglobulin are shown in Appendix A, B, and D, which are hereby incorporated by reference in their entireties.

TABLE 5

| Lactoglobulin (Bovine) | Q1 | Q3 | Fragment Ion |
|---|---|---|---|
| VLVLDTDYK | 533.3 | 853.6 | 2y7 |
| (SEQ ID NO: 24) | 533.3 | 754.6 | 2y6 |
| doubly-charged | 533.3 | 641.4 | 2y5 |
| IDALNENK | 458.7 | 803.6 | 2y7 |
| (SEQ ID NO: 25) | 458.7 | 688.5 | 2y6 |
| doubly-charged | 458.7 | 504.2 | 2y4 |
| VYVEELKPTPEGDLEILLQK | 1158 | 1453.5 | 2y13 |
| (SEQ ID NO: 26) | 1158 | 1581.5 | 2y14 |
| doubly-charged | 1158 | 1254.9 | 2y11 |
| VYVEELKPTPEGDLEILLQK | 772.3 | 1026.5 | 3y18d |
| (SEQ ID NO: 26) | 772.3 | 977 | 3y17d |
| triply-charged | 772.3 | 912.5 | 3y16d |
| TPEVDDEALEK | 623.3 | 572.9 | 2y10d |
| (SEQ ID NO: 27) | 623.3 | 918.5 | 2y8 |
| doubly-charged | 623.3 | 819.5 | 2y7 |
| | 623.3 | 1047.5 | |
| WENGECAQK | 561.3 | 806.4 | 2y7 |
| (SEQ ID NO: 28) | 561.3 | 935.4 | 2y8 |
| doubly-charged | 561.3 | 692.6 | 2y6 |
| ALPMHIR | 419.2 | 653.3 | 2y5 |
| (SEQ ID NO: 29) | 419.2 | 555.9 | 2y4 |
| doubly-charged | 419.2 | 424.9 | 2y3 |

According to some embodiments, the method can comprise detecting and/or quantifying barley (*Hordeum vulgare*) in the sample by detecting at least one isolated peptide specific to a barley, such as example the B1-hordein or B3-hordein which can have, for example, one or more of the peptides having an amino acid sequence of SEQ ID NOS: 30-33 identified herein. For example, a triple quadrupole mass spectrometer can be used to monitor selected Multiple Reaction Monitoring (MRM) transitions to determine the presence and/or quantity of barley-specific peptides in the sample. In some embodiments, the barley-specific peptide can have the amino acid sequence of SEQ ID NO: 30 identified herein, and the method can include monitoring at least one precursor-product ion pair transition having an m/z value of about 835/948, 835/1097, or 835/1228. In other embodiments, the barley-specific peptide can have the amino acid sequence of SEQ ID NO: 31 identified herein, and the method can include monitoring at least one precursor-product ion pair transition having an m/z value of about 336/515, 336/554, or 336/497. In other embodiments, the barley-specific peptide can have the amino acid sequence of SEQ ID NO: 32 identified herein, and the method can include monitoring at least one precursor-product ion pair transition having an m/z value of about 820/1097, 820/548, or 820/713. In other embodiments, the barley-specific peptide can have the amino acid sequence of SEQ ID NO: 33, and the method can include monitoring at least one precursor-product ion pair transition having an m/z value of about 499/785, 499/575, or 499/393.

In one exemplary embodiment, the method can include monitoring multiple precursor-product ion pair transitions associated with each barley-specific peptide. By way of example, the barley-specific peptide having the amino acid sequence of SEQ ID NO: 30 can be identified by monitoring any two of the precursor-product ion pair transitions having an m/z value of about 835/948, 835/1097, or 835/1228. In one embodiment, all three of the identified precursor-product ion pairs can be monitored. Likewise, the amino acid sequence of SEQ ID NO: 31-33 can be used in a similar fashion.

In one embodiment, the method for detecting or quantifying barley in the sample can include detecting multiple barley-specific peptides. By way of non-limiting example, barley can be quantified by using any combination, or all, of the peptides having the amino acid sequences of SEQ ID NOS: 30-33 identified herein. As discussed above, for each peptide, one or more of the precursor-product ion pair transitions can be monitored.

Table 6 below shows sequences SEQ ID NOS: 30-33 of the peptides determined, according to the present teachings, to be specific to barley, along with their optimal MRM Q1, Q3 transitions. According to various embodiments, these observed peptides and transitions can be used to enable a reliable quantitation of the barley proteins present in the sample.

TABLE 6

| Barley Proteins | Q1 | Q2 | Fragment Ion |
|---|---|---|---|
| TLPMMCSVNVPLYR | 835.4 | 947.5 | 2/y8 |
| (SEQ ID NO: 30) | 835.4 | 1096.5 | 2/y9 |
| doubly-charged | 835.4 | 1227.6 | 2/y10 |
| GVGPSVGV | 336.2 | 515.3 | 2/y6 |
| (SEQ ID NO: 31) | 336.2 | 554.3 | 2b7 |
| doubly-charged | 336.2 | 497.3 | 2b6 |
| TLPTMCSVNVPLYR | 820.4 | 1096.5 | 2/y8 |
| (SEQ ID NO: 32) | 820.4 | 548.3 | 2/y9(2) |
| doubly-charged | 820.4 | 713.4 | 2/y12(2) |
| NTDGSTDYGILQINSR | 499.3 | 785.5 | 2/y7 |
| (SEQ ID NO: 33) | 499.3 | 575.3 | 2/y5 |
| doubly-charged | 499.3 | 393.3 | 2/y7(2) |

It is understood by those skilled in the art that in some cases individual amino acids present in the sequences can be modified through the use of conventional methods in the process of sample preparation. In another embodiment, it is intended that such modified sequences also be captured. For example, SEQ ID NO: 30 contains a cysteine moiety, which can be blocked with a blocking agent in a process of sample preparation, for example, methyl methanethiosulfonate which may result in a sequence in which the cysteine has been blocked from further reacting. Other blocking agents are known in the art and can include iodoacetamide. It should therefore be realized that SEQ ID NO: 30-33 include within their scope modified peptide sequences in which individual amino acids have been modified to include such blocking agents. Persons skilled in the art would recognize that though the sequence will be substantially similar with the addition of the blocking agent, the masses will change accordingly. Such modifications are also applicable to all the sequences of all the allergens disclosed herein.

According to other embodiments, the methods can also be used to identify and quantify other allergens in addition to the allergens disclosed above, such other allergens including low and high molecular weight glutenins, and proteins from mustard, oats, rye, sesame, wheat, brazil nuts, hazelnuts, macadamia nuts, peanuts, pistachio nuts and walnuts. As exemplified above for the allergens such as ovalbumin, lysozyme, casein isoform S1, casein isoform S2, lactoglobulin, and barley, this can also be accomplished by detecting at least one isolated peptide sequence specific to the allergen, for example, one of more of the peptides having the amino acid sequence for the specific allergen previously described or as outlined in Tables 7-19.

According to some embodiments, the method can comprise detecting and/or quantifying the allergen by detecting at least one isolated peptide specific to that allergen, for example, one or more of the peptides having an amino acid sequence of disclosed in Tables 7-19 for a specific allergen. For example, a triple quadrupole mass spectrometer can be used to monitor selected Multiple Reaction Monitoring (MRM) transitions to determine the presence and/or quantity of the allergen-specific peptide in the sample. In some embodiments, the allergen specific peptide can have an amino acid sequence that is described in Tables 7-19, and the method can include monitoring at least one precursor-product ion pair transition having an m/z value specific to that allergen and described in Tables 7-19, and can also include monitoring the fragment ion, specific to that allergen as described, where available in Tables 7-19.

In one exemplary embodiment, the method can include monitoring multiple precursor-product ion pair transitions associated with each allergen-specific peptide when such a peptide has more than one precursor-product ion pair transition associated with it. By way of example, an allergen specific peptide having an amino acid sequence described in Tables 7-19 can be identified by monitoring any two (where available) of the precursor-product ion pair transitions found in Tables 7-19 for a specific allergen. In one embodiment, and where available, three or more of the identified precursor-product ion pairs can be monitored, where available.

In one embodiment, the method for detecting or quantifying other allergens, including low and high molecular weight glutenins, and proteins from mustard, oats, rye, sesame, wheat, brazil nuts, hazelnuts, macadamia nuts, peanuts, pistachio nuts and walnuts, can include detecting multiple allergen-specific peptides. By way of non-limiting example, the allergen can be quantified by using any combination, or all, of the peptides having the amino acid sequences for a specific allergen described in Tables 7-19, identified herein. As discussed above, for each peptide, one or more of the precursor-product ion pair transitions can be monitored.

Tables 7-19 below shows sequences of the peptides determined, according to the present teachings, to be specific to allergens of low and high molecular weight glutenins, and allergens from proteins from mustard, oats, rye, sesame, wheat, brazil nuts, hazelnuts, macadamia nuts, peanuts, pistachio nuts and walnuts, along with their optimal MRM Q1, Q3 transitions and fragment ion. According to various embodiments, these observed peptides and transitions can be used to enable a reliable quantitation of the allergens present in the sample.

For further clarity, according to the present teachings, each of the allergens described in Tables 7-19 shows sequences of the peptides determined for that allergen, along with their optimal MRM Q1, Q3 transitions and fragment ion information. According to various embodiments, these observed peptides and transitions can be used to enable a reliable quantitation of that allergen present in the sample.

TABLE 7

| Glutenin, low MW | Q1 | Q3 | Fragment Ion |
|---|---|---|---|
| SDCQVMR | 448.2 | 693.3 | 2/y5 |
| (SEQ ID NO: 34) | 448.2 | 533.3 | 2/y4 |
| doubly-charged | 448.2 | 808.3 | 2/y6 |
| | 448.2 | 491.2 | 2/b4 |
| | 448.2 | 590.2 | 2/b5 |
| APFASIVASIGGQ | 609.3 | 686.4 | 2/b7 |
| (SEQ ID NO: 35) | 609.3 | 757.4 | 2/b8 |
| doubly-charged | 609.3 | 1071.6 | 2/b12 |
| | 609.3 | 631.3 | 2/y7 |
| | 609.3 | 844.5 | 2/b9 |
| SLVLQTLPTMCNVYVPPYCSTIR | 904.8 | 993.5 | 3/y8 |
| (SEQ ID NO: 36) | 904.8 | 1092.6 | 3/y9 |
| triply-charged | 904.8 | 953.6 | 3/b9 |
| | 904.8 | 1084.6 | 3/b10 |
| SLVLQTLPTMCNVYVPPYCSTIR | 923.8 | 993.5 | 3/y8 |
| (SEQ ID NO: 37) | 923.8 | 1092.6 | 3/y9 |
| triply-charged | 923.8 | 1241.6 | 3/b21(2) |
| QPFPQQPQQPYPQQPQQ PFPQTQQPQQPFPQSK | 982.7 | 1056.6 | 4/y9 |
| (SEQ ID NO: 38) | 982.7 | 1079.5 | 4/b9 |
| quadruple-charged | 982.7 | 1118.6 | 4/y19(2) |
| | 982.7 | 1184.6 | 4/y10 |
| VSIILPR | 399.3 | 698.5 | 2/y6 |
| (SEQ ID NO: 39) | 399.3 | 498.3 | 2/y4 |
| doubly-charged | 399.3 | 611.4 | 2/y5 |
| GIIQPQQPAQLEGIR | 824.5 | 1236.7 | 2/y11 |
| (SEQ ID NO: 40) | 824.5 | 883.5 | 2/y8 |
| doubly-charged | 824.5 | 1011.6 | 2/y9 |
| | 824.5 | 1139.6 | 2/y10 |
| | 824.5 | 1061.6 | 2/b10 |
| AQGLGIIQPQQPAQLEGIR | 1009.1 | 1236.7 | 2/y11 |
| (SEQ ID NO: 41) | 1009.1 | 1134.6 | 2/b11 |
| doubly-charged | 1009.1 | 1139.6 | 2/y10 |
| NFLLQQCNHVSLVSSLV SIILPR | 879.8 | 1084.7 | 3/y10 |
| | 879.8 | 1183.7 | 3/y11 |
| (SEQ ID NO: 42) | 879.8 | 997.6 | 3/y9 |
| triply-charged | 879.8 | 910.6 | 3/y8 |
| | 879.8 | 1127.1 | 3/b20(2) |
| PSGQVQWPQQQPFPQP QQPFCQPQR | 1049.5 | 1182.6 | 3/y19(2) |
| | 1049.5 | 1060.5 | 3/y8 |
| (SEQ ID NO: 43) | 1049.5 | 1136.6 | 3/b10 |
| triply-charged | 1049.5 | 1188.6 | 3/y9 |
| VNVPLYR | 430.8 | 548.3 | 2/y4 |
| (SEQ ID NO: 44) | 430.8 | 647.4 | 2/y5 |
| doubly-charged | 430.8 | 451.3 | 2/y3 |
| | 430.8 | 761.4 | 2/y6 |
| LEVMTSIALR | 566.8 | 890.5 | 2/y8 |
| (SEQ ID NO: 45) | 566.8 | 791.4 | 2/y7 |
| doubly-charged | 566.8 | 660.4 | 2/y6 |
| | 566.8 | 1019.6 | 2/y9 |
| TTTSVPFGVTGVG | 640.3 | 790.4 | 2/y9 |
| (SEQ ID NO: 46) | 640.3 | 1105.6 | 2/b12 |
| doubly-charged | 640.3 | 890.5 | 2/b9 |
| | 640.3 | 693.4 | 2/y8 |
| | 640.3 | 1048.5 | 2/b11 |

TABLE 7-continued

| Glutenin, low MW | Q1 | Q3 | Fragment Ion |
|---|---|---|---|
| TTTSVPFGVTGVGA | 675.9 | 861.5 | 2/y10 |
| (SEQ ID NO: 47) | 675.9 | 890.5 | 2/b9 |
| triply-charged | 675.9 | 1105.6 | 2/b12 |
| | 675.9 | 1204.6 | 2/b13 |
| | 675.9 | 764.4 | 2/y9 |
| TTTSVPFGVTGVGAY | 757.4 | 1024.5 | 2/y11 |
| (SEQ ID NO: 48) | 757.4 | 890.5 | 2/b9 |
| doubly-charged | 757.4 | 780.4 | 2/y9 |
| ILPTMCSVNVPLYR | 831.9 | 1107.6 | 2/y9 |
| (SEQ ID NO: 49) | 831.9 | 947.5 | 2/y8 |
| doubly-charged | 831.9 | 1115.6 | 2/b10 |
| SQMLQQSSCHVMQQQCCQQ LPQIPQQSR | 875.9 | 953.5 | 4/y8 |
| | 875.9 | 1066.6 | 4/y9 |
| (SEQ ID NO: 50) | 875.9 | 1194.7 | 4/y10 |
| quadruple-charged | | | |
| SQMLQQSSCHVMQQQCC QQLPQIPQQSRYEAIR | 827.4 | 850.0 | 5/y14(2) |
| | 827.4 | 914.0 | 5/y15(2) |
| (SEQ ID NO: 51) | 827.4 | 1247.7 | 5/y10 |
| Quintuply-charged | | | |
| APFASIVAGIGGQ | 594.3 | 927.5 | 2/b10 |
| (SEQ ID NO: 52) | 594.3 | 814.5 | 2/b9 |
| Doubly-charged | 594.3 | 686.4 | 2/b7 |
| | 594.3 | 757.4 | 2/b8 |
| | 594.3 | 601.3 | 2/y7 |
| APFASIVAGIGGQ | 622.8 | 871.5 | 2/b9 |
| (SEQ ID NO: 53) | 622.8 | 743.4 | 2/b7 |
| doubly-charged | 622.8 | 814.5 | 2/b8 |
| | 622.8 | 644.3 | 2/b6 |
| | 622.8 | 984.6 | 2/b10 |
| RAPFASIVAGIGGQ | 672.4 | 1083.6 | 2/b11 |
| (SEQ ID NO: 54) | 672.4 | 970.6 | 2/b10 |
| doubly-charged | 672.4 | 913.5 | 2/b9 |
| | 672.4 | 842.5 | 2/b8 |
| | 672.4 | 1140.7 | 2/b12 |
| SLVLQTLPSMCNVYVPPECSIMR | 917.8 | 989.5 | 3/y8 |
| (SEQ ID NO: 55) | 917.8 | 1088.5 | 3/y9 |
| triply-charged | 917.8 | 1223.6 | 3/b21(2) |
| QQPFPQTQQPQQPFPQ QPQQPFPQTQQP | 1110.2 | 1180.6 | 3/b10 |
| | 1110.2 | 1198.6 | 3/y10 |
| (SEQ ID NO: 56) | 1110.2 | 1242.6 | 3/b21(2) |
| triply-charged | | | |
| QIPEQSRHESIR | 493.9 | 619.8 | 3/y10(2) |
| (SEQ ID NO: 57) | 493.9 | 641.3 | 3/y5 |
| triply-charged | 493.9 | 571.3 | 3/y9(2) |
| | 493.9 | 506.8 | 3/y8(2) |
| VFLQQQCIPVAMQR | 859.5 | 974.5 | 2/y8 |
| (SEQ ID NO: 58) | 859.5 | 1102.6 | 2/y9 |
| doubly-charged | 859.5 | 1230.6 | 2/y10 |
| | 859.5 | 1017.5 | 2/b8 |
| | 859.5 | 1213.6 | 2/b10 |
| QQQIPVIHPSVLQQLNPCK | 743.1 | 865.5 | 3/y15(2) |
| (SEQ ID NO: 59) | 743.1 | 1000.5 | 3/y8 |
| triply-charged | 743.1 | 1099.6 | 3/y9 |
| | 743.1 | 1186.6 | 3/y10 |
| | 743.1 | 986.1 | 3/y17(2) |

TABLE 8

| Gluten, high | Q1 | Q3 | Fragment Ion |
|---|---|---|---|
| ELQELQER (SEQ ID NO: 60) doubly-charged | 522.8 | 674.4 | 2/y5 |
| | 522.8 | 802.4 | 2/y6 |
| | 522.8 | 545.3 | 2/y4 |
| | 522.8 | 432.2 | 2/y3 |
| LEGGDALSASQ (SEQ ID NO: 61) doubly-charged | 524.3 | 543.2 | 2/b6 |
| | 524.3 | 656.3 | 2/b7 |
| | 524.3 | 814.4 | 2/b9 |
| | 524.3 | 743.4 | 2/b8 |
| | 524.3 | 901.4 | 2/b10 |
| | 524.3 | 234.1 | 2/y2 |
| | 524.3 | 392.2 | 2/y4 |
| IFWGIPALLK (SEQ ID NO: 62) doubly-charged | 579.4 | 897.6 | 2/y8 |
| | 579.4 | 711.5 | 2/y7 |
| | 579.4 | 898.5 | 2/b8 |
| | 579.4 | 1044.6 | 2/y9 |
| | 579.4 | 541.4 | 2/y5 |
| IFWGIPALLK (SEQ ID NO: 63) doubly-charged | 607.9 | 897.6 | 2/y8 |
| | 607.9 | 711.5 | 2/y7 |
| | 607.9 | 1044.6 | 2/y9 |
| | 607.9 | 654.5 | 2/y6 |
| | 607.9 | 541.4 | 2/y5 |
| IFWGIPALLKR (SEQ ID NO: 64) doubly-charged | 657.4 | 697.5 | 2/y6 |
| | 657.4 | 1053.7 | 2/y9 |
| | 657.4 | 867.6 | 2/y8 |
| | 657.4 | 810.6 | 2/y7 |
| | 657.4 | 1200.7 | 2/y10 |
| GEASEQLQCER (SEQ ID NO: 65) doubly-charged | 682.3 | 705.3 | 2/y5 |
| | 682.3 | 833.4 | 2/y6 |
| | 682.3 | 1177.5 | 2/y9 |
| | 682.3 | 772.4 | 2/b7 |
| | 682.3 | 592.3 | 2/y4 |
| IFWGIPALLKR (SEQ ID NO: 66) doubly-charged | 685.9 | 1053.7 | 2/y9 |
| | 685.9 | 697.5 | 2/y6 |
| | 685.9 | 867.6 | 2/y8 |
| | 685.9 | 1200.7 | 2/y10 |
| EGEASEQLQCER (SEQ ID NO: 67) doubly-charged | 718.3 | 1049.5 | 2/y8 |
| | 718.3 | 833.4 | 2/y6 |
| | 718.3 | 962.4 | 2/y7 |
| | 718.3 | 1120.5 | 2/y9 |
| | 718.3 | 592.3 | 2/y4 |
| AQQLAAQLPAMCR (SEQ ID NO: 68) doubly-charged | 729.4 | 1017.5 | 2/y9 |
| | 729.4 | 946.5 | 2/y8 |
| | 729.4 | 875.4 | 2/y7 |
| | 729.4 | 1130.6 | 2/y10 |
| | 729.4 | 747.4 | 2/y6 |
| SVAVSQVAR (SEQ ID NO: 69) doubly-charged | 458.8 | 730.4 | 2/y7 |
| | 458.8 | 560.3 | 2/y5 |
| | 458.8 | 659.4 | 2/y6 |
| | 458.8 | 473.3 | 2/y4 |
| | 458.8 | 829.5 | 2/y8 |
| QVVDQQLAGR (SEQ ID NO: 70) doubly-charged | 557.3 | 886.5 | 2/y8 |
| | 557.3 | 787.4 | 2/y7 |
| | 557.3 | 672.4 | 2/y6 |
| | 557.3 | 985.5 | 2/y9 |
| ELQESSLEACR (SEQ ID NO: 71) doubly-charged | 661.3 | 822.4 | 2/y7 |
| | 661.3 | 951.4 | 2/y8 |
| | 661.3 | 735.4 | 2/y6 |
| | 661.3 | 1079.5 | 2/y9 |
| | 661.3 | 535.2 | 2/y4 |
| AQQPATQLPTVCR (SEQ ID NO: 72) doubly-charged | 735.4 | 1142.6 | 2/y10 |
| | 735.4 | 745.4 | 2/y6 |
| | 735.4 | 974.5 | 2/y8 |
| | 735.4 | 873.4 | 2/y7 |
| | 735.4 | 1045.5 | 2/y9 |
| | 735.4 | 632.3 | 2/y5 |
| QLQCERELQESSLEACR (SEQ ID NO: 73) triply-charged | 712.7 | 822.4 | 3/y7 |
| | 712.7 | 951.4 | 3/y8 |
| | 712.7 | 735.4 | 3/y6 |
| | 712.7 | 947.9 | 3/y15(2) |
| | 712.7 | 883.9 | 3/y14(2) |
| QVVDQQLAGRLPWSTGLQMR (SEQ ID NO: 74) triply-charged | 761.7 | 1075.5 | 3/y9 |
| | 761.7 | 1028.5 | 3/y18(2) |
| | 761.7 | 793.4 | 3/y14(2) |
| | 761.7 | 979.0 | 3/y17(2) |
| | 761.7 | 857.5 | 3/y15(2) |
| QQPVQGQQPEQGQQPGQWQQGYYPTSPQQLGQGQQPR (SEQ ID NO: 75) quadruply-charged | 1048.3 | 1236.6 | 4/y11 |
| | 1048.3 | 1120.5 | 4/b10 |
| | 1048.3 | 1139.6 | 4/y10 |
| | 1048.3 | 894.4 | 4/b8 |
| | 1048.3 | 770.4 | 4/y7 |
| | 1048.3 | 761.4 | 4/y14(2) |
| QGYYPTSLQQPGQGQQIGQGQQGYYPTSPQHTGQR (SEQ ID NO: 76) quadruply-charged | 966.7 | 1166.6 | 4/b10 |
| | 966.7 | 995.5 | 4/y18(2) |
| | 966.7 | 1108.6 | 4/y10 |
| | 966.7 | 1208.6 | 4/y22(2) |
| | 966.7 | 1038.5 | 4/b9 |
| QWLQPR (SEQ ID NO: 77) doubly-charged | 414.2 | 513.3 | 2/y4 |
| | 414.2 | 428.2 | 2/b3 |
| | 414.2 | 699.4 | 2/y5 |
| LEGGDALLASQ (SEQ ID NO: 78) doubly-charged | 537.3 | 656.3 | 2/b7 |
| | 537.3 | 543.2 | 2/b6 |
| | 537.3 | 769.4 | 2/b8 |
| | 537.3 | 840.5 | 2/b9 |
| LEGGDALLASQ (SEQ ID NO: 79) doubly-charged | 565.8 | 713.4 | 2/b7 |
| | 565.8 | 600.3 | 2/b6 |
| | 565.8 | 826.4 | 2/b8 |
| | 565.8 | 897.5 | 2/b9 |

TABLE 9

| Mustard Proteins | Q1 | Q3 | Fragment Ion |
|---|---|---|---|
| PAGPFR (SEQ ID NO: 80) doubly-charged | 322.7 | 476.3 | 2/y4 |
| | 322.7 | 547.3 | 2/y5 |
| | 322.7 | 470.2 | 2/b5 |
| | 322.7 | 419.2 | 2/y3 |
| PAGPFRIPK (SEQ ID NO: 81) doubly-charged | 491.8 | 757.5 | 2/y6 |
| | 491.8 | 660.4 | 2/y5 |
| | 491.8 | 814.5 | 2/y7 |
| | 491.8 | 885.5 | 2/y8 |
| IYQTATHLPK (SEQ ID NO: 82) doubly-charged | 586.3 | 666.4 | 2/y6 |
| | 586.3 | 767.4 | 2/y7 |
| | 586.3 | 895.5 | 2/y8 |
| QVSVCPFK (SEQ ID NO: 83) doubly-charged | 482.8 | 650.3 | 2/y5 |
| | 482.8 | 737.4 | 2/y6 |
| | 482.8 | 836.4 | 2/y7 |
| | 482.8 | 818.4 | 2/b7 |
| QVSVCPFKK (SEQ ID NO: 84) doubly-charged | 546.8 | 778.4 | 2/y6 |
| | 546.8 | 865.5 | 2/y7 |
| | 546.8 | 964.5 | 2/y8 |
| QVSVCPFKK (SEQ ID NO: 85) triply-charged | 364.9 | 519.3 | 3/y4 |

TABLE 9-continued

| Mustard Proteins | Q1 | Q3 | Fragment Ion |
|---|---|---|---|
| PAGPFGIPK (SEQ ID NO: 86) doubly-charged | 442.3 442.3 442.3 442.3 | 658.4 715.4 786.5 737.4 | 2/y6 2/y7 2/y8 2/b8 |
| QQLEQQGQQGPHLQHVISR (SEQ ID NO: 87) triply-charged | 737.7 737.7 737.7 | 1143.6 989.6 1086.6 | 3/y10 3/y8 3/y9 |
| QQLEQQGQQGPHLQHVISR (SEQ ID NO: 88) quadruply-charged | 553.5 | 1086.6 | 4/y9 |
| IYQTATHLPR (SEQ ID NO: 89) doubly-charged | 600.3 600.3 600.3 | 694.4 795.5 923.5 | 2/y6 2/y7 2/y8 |
| IYQTATHLPR (SEQ ID NO: 90) triply-charged | 400.6 | 694.4 | 3/y6 |
| QVSVCPFQK (SEQ ID NO: 91) doubly-charged | 546.8 546.8 546.8 | 778.4 865.4 964.5 | 2/y6 2/y7 2/y8 |
| QVSVCPFQK (SEQ ID NO: 92) triply-charged | 364.9 | 519.3 | 3/y4 |
| VCNIPQVSVCPFK (SEQ ID NO: 93) doubly-charged | 774.4 774.4 774.4 | 1061.5 964.5 1174.6 | 2/y9 2/y8 21y10 |
| VCNIPQVSVCPFK (SEQ ID NO: 94) triply-charged | 516.6 | 964.5 | 3/y8 |
| VCNIPQVSVCPFKK (SEQ ID NO: 95) | 838.4 838.4 838.4 | 1189.6 964.5 1092.6 | 21y10 2/y8 2/y9 |
| VCNIPQVSVCPFKK (SEQ ID NO: 96) triply-charged | 559.3 | 964.5 | 3/y8 |
| QQLGQQGQQGPQVQHVISR (SEQ ID NO: 97) doubly-charged | 1058.6 1058.6 1058.6 | 1120.6 1248.7 1063.6 | 2/y10 2/y11 2/y9 |
| QQLGQQGQQGPQVQHVISR (SEQ ID NO: 98) triply-charged | 706.0 | 1063.6 | 3/y9 |
| IYQTATHLPR (SEQ ID NO: 99) doubly-charged | 600.3 | 1086.6 | 2/y9 |
| AGPFR (SEQ ID NO: 100) doubly-charged | 274.2 274.2 274.2 274.2 | 419.2 476.2 322.2 373.2 | 2/y3 2/y4 2/y2 2/b4 |
| AVKQQIR (SEQ ID NO: 101) doubly-charged | 421.8 421.8 421.8 421.8 | 672.4 771.5 668.4 555.3 | 2/y5 2/y6 2/b6 2/b5 |
| QQGQQQGQQGQQLQHEISR (SEQ ID NO: 102) triply-charged | 736.0 736.0 736.0 736.0 | 882.5 1010.5 1138.6 1195.6 | 3/y7 3/y8 3/y9 3/y10 |
| VCNIPR (SEQ ID NO: 103) doubly-charged | 379.7 379.7 379.7 379.7 | 499.3 659.3 584.3 487.2 | 2/y4 2/y5 2/b5 2/b4 |

TABLE 9-continued

| Mustard Proteins | Q1 | Q3 | Fragment Ion |
|---|---|---|---|
| VSICPFQK (SEQ ID NO: 104) doubly-charged | 489.8 489.8 489.8 | 519.3 679.3 792.4 | 2/y4 2/y5 2/y6 |
| VSICPFQK (SEQ ID NO: 105) triply-charged | 326.8 | 519.3 | 3/y4 |
| EFRQAHLR (SEQ ID NO: 106) doubly-charged | 592.8 592.8 592.8 | 1055.6 752.4 908.5 | 2/y8 2/y6 2/y7 |
| EFRQAHLR (SEQ ID NO: 107) triply-charged | 395.6 | 752.4 | 3/y6 |
| QAQHLR (SEQ ID NO: 108) doubly-charged | 376.7 376.7 376.7 376.7 | 553.3 624.4 578.3 465.2 | 2/y4 2/y5 2/b5 2/b4 |
| ACQQWLHR (SEQ ID NO: 109) doubly-charged | 549.8 549.8 549.8 549.8 | 739.4 867.5 1027.5 924.4 | 2/y5 2/y6 2/y7 2/b7 |
| QQVRQQGHQQQMQHVISR (SEQ ID NO: 110) triply-charged | 739.4 739.4 739.4 | 1218.6 998.5 1126.6 | 3/b10 3/y8 3/y9 |
| QQVRQQGHQQQMQHVISR (SEQ ID NO: 111) quadruply-charged | 554.8 | 998.5 | 4/y8 |
| IYQTATHLPR (SEQ ID NO: 112) doubly-charged | 600.3 600.3 600.3 600.3 | 694.4 795.5 923.5 1086.6 | 2/y6 2/y7 2/y8 2/y9 |

TABLE 10

| Oats Proteins | Q1 | Q3 | Fragment Ion |
|---|---|---|---|
| QFLVQQCSPVAVVPFLR (SEQ ID NO: 113) doubly-charged | 989.0 989.0 989.0 | 997.6 1084.7 1233.7 | 2/y9 2/y10 2/y11 |
| SQILQQSSCQVMR (SEQ ID NO: 114) doubly-charged | 777.4 777.4 777.4 | 984.4 1112.5 1225.6 | 2/y8 2/y9 2/y10 |
| QLEQIPEQLR (SEQ ID NO: 115) doubly-charged | 627.4 627.4 | 642.4 1012.5 | 2/y5 2/y8 |
| QLEQIPEQLR (SEQ ID NO: 116) triply-charged | 418.6 | 642.4 | 3/y5 |

TABLE 11

| Rye Proteins | Q1 | Q3 | Fragment Ion |
|---|---|---|---|
| NVLLQQCSPVALVSSLR (SEQ ID NO: 117) doubly-charged | 937.0 | 1177.6 | 2/y11 |

TABLE 11-continued

| Rye Proteins | Q1 | Q3 | Fragment Ion |
|---|---|---|---|
| NVLLQQCSPVALVSSLR (SEQ ID NO: 118) triply-charged | 625.0 625.0 | 941.6 1177.6 | 3/y9 3/y11 |
| EGVQILLPQSHQQHVGQGAL AQVQGIIQPQQLSQLEVVR (SEQ ID NO: 119) quintuply-charged | 851.7 851.7 851.7 | 1199.7 1071.6 1210.2 | 5/y10 5/y9 5/b23(2) |
| SLVLQNLPTMCNVYVPR (SEQ ID NO: 120) doubly-charged | 997.0 | 1225.6 | 2/y10 |
| SLVLQNLPTMCNVYVPR (SEQ ID NO: 121) triply-charged | 665.0 665.0 | 1225.6 1128.5 | 3/y10 3/y9 |
| QCSTIQAPFASIVTGIVGH (SEQ ID NO: 122) doubly-charged | 988.0 988.0 | 1100.6 1197.7 | 2/y11 2/y12 |
| QCSTIQAPFASIVTGIVGH (SEQ ID NO: 123) triply-charged | 659.0 | 1197.7 | 3/y12 |

TABLE 12

| Sesame Proteins | Q1 | Q3 | Fragment Ion |
|---|---|---|---|
| ISGAQPSLR (SEQ ID NO: 124) doubly-charged | 464.8 464.8 464.8 | 472.3 728.4 815.4 | 2/y4 21y7 2/y8 |
| LVYIER (SEQ ID NO: 125) doubly-charged | 396.7 396.7 396.7 | 679.4 417.3 579.8 | 2/y5 21y3 |
| AFDAELLSEAFNVPQETIR (SEQ ID NO: 126) triply-charged | 717.4 717.4 717.4 | 743.4 956.5 372.4 | 3/y6 3/y8 3/y6(2) |
| GLIVMAR (SEQ ID NO: 127) doubly-charged | 380.2 380.2 380.2 | 589.4 476.3 377.2 | 2/y5 2/y4 2/y3 |
| EADIF SR (SEQ ID NO: 128) doubly-charged | 419.2 419.2 419.2 | 522.3 637.3 409.2 | 2/y4 2/y5 2/y3 |
| SPLAGYTSVIR (SEQ ID NO: 129) doubly-charged | 582.3 582.3 582.3 | 795.4 866.5 979.6 | 2/y7 2/y8 2/y9 |
| AMPLQVITNSYQISPNQAQALK (SEQ ID NO: 130) triply-charged | 805.8 805.8 805.8 | 869.5 1069.6 956.5 | 3/y8 3/y10 3/y9 |
| HCMQWMR (SEQ ID NO: 131) doubly-charged | 519.2 519.2 519.2 | 751.3 900.3 620.3 | 2/y5 2/y6 2/y4 |
| MCGMSYPTECR (SEQ ID NO: 132) doubly-charged | 685.2 685.2 685.2 | 901.4 1089.4 1238.4 | 2/y7 2/y9 2/y10 |

TABLE 13

| Wheat Proteins | Q1 | Q3 | Fragment Ion |
|---|---|---|---|
| SVAVSQVAR (SEQ ID NO: 133) doubly-charged | 458.8 458.8 458.8 | 730.4 560.3 | 2/y7 2/y5 |
| EHGAQEGQAGTGAFPR (SEQ ID NO: 134) triply-charged | 538.3 538.3 538.3 | 547.3 776.4 705.4 | 3/y5 3/y8 3/y7 |
| QVVDQQLAGR (SEQ ID NO: 135) doubly-charged | 557.3 557.3 | 886.5 787.4 | 2/y8 2/y7 |
| IFWGIPALLK (SEQ ID NO: 136) doubly-charged | 579.4 579.4 | 897.6 711.5 | 2/y8 2/y7 |
| LPWSTGLQMR (SEQ ID NO: 137) doubly-charged | 594.8 594.8 594.8 | 792.4 978.5 538.9 | 2/y7 2/y8 2/y9(2) |
| YDPTAYNTILR (SEQ ID NO: 138) doubly-charged | 663.8 663.8 | 850.5 779.4 | 2/y7 2/y6 |

TABLE 14

| Brazil Proteins | Q1 | Q3 | Fragment Ion |
|---|---|---|---|
| QQMLSHCR (SEQ ID NO: 139) doubly-charged | 524.7 524.7 524.7 | 661.3 792.3 548.2 | 2/y5 21y6 2/y4 |
| GMEPHMSECCEQLEGMDESCR (SEQ ID NO: 140) triply-charged | 847.0 847.0 847.0 | 1085.4 843.3 972.3 | 3/y9 31y7 3/y8 |
| MMMMR (SEQ ID NO: 141) doubly-charged | 350.1 350.1 350.1 | 568.2 437.2 306.5 | 2/y4 21y3 |
| MQQEEMQPR (SEQ ID NO: 142) doubly-charged | 588.8 588.8 588.8 | 660.3 789.4 917.4 | 2/y5 2/y6 2/y7 |
| LAENIP SR (SEQ ID NO: 143) doubly-charged | 450.3 450.3 450.3 | 586.3 715.4 786.4 | 2/y5 2/y6 2/y7 |
| CNLSPMR (SEQ ID NO: 144) doubly-charged | 433.7 433.7 433.7 | 603.3 490.2 403.2 | 2/y5 2/y4 2/y3 |
| QQQLNHCR (SEQ ID NO: 145) doubly-charged | 536.7 536.7 536.7 | 688.3 816.4 575.2 | 2/y5 2/y6 2/y4 |
| MDEMCR (SEQ ID NO: 146) doubly-charged | 415.6 415.6 415.6 415.6 | 584.2 699.2 507.2 455.2 | 2/y4 2/y5 2/b4 2/y3 |
| CNLSPQR (SEQ ID NO: 147) doubly-charged | 432.2 432.2 432.2 | 600.4 487.3 400.2 | 2/y5 2/y4 2/y3 |
| CAGVAALR (SEQ ID NO: 148) doubly-charged | 403.7 403.7 403.7 403.7 403.7 | 529.4 586.4 657.4 519.2 430.3 | 2/y5 2/y6 2/y7 2/b6 2/y4 |

TABLE 14-continued

| Brazil Proteins | Q1 | Q3 | Fragment Ion |
|---|---|---|---|
| LYYVTQGR | 500.3 | 723.4 | 2/y6 |
| (SEQ ID NO: 149) | 500.3 | 886.4 | 2/y7 |
| doubly-charged | 500.3 | 461.3 | 2/y4 |
| HFFLAGNIQR | 601.8 | 771.5 | 2/y7 |
| (SEQ ID NO: 150) | 601.8 | 918.5 | 2/y8 |
| doubly-charged | 601.8 | 658.4 | 2/y6 |
| GGQQILADNVFK | 645.4 | 806.4 | 2/y7 |
| (SEQ ID NO: 151) | 645.4 | 919.5 | 2/y8 |
| doubly-charged | 645.4 | 693.4 | 2/y6 |
| GFNMEALADVLGFGMDTETAR | 749.0 | 880.4 | 3/y8 |
| (SEQ ID NO: 152) | 749.0 | 1084.5 | 3/y10 |
| triply-charged | 749.0 | 692.3 | 3/y6 |
| GVLYENAMMAPLWR | 825.9 | 1089.5 | 2/y9 |
| (SEQ ID NO: 153) | 825.9 | 904.5 | 2/y7 |
| doubly-charged | 825.9 | 571.3 | 2/y4 |
| GIPVGVLANAYR | 615.4 | 863.5 | 2/y8 |
| (SEQ ID NO: 154) | 615.4 | 962.5 | 2/y9 |
| doubly-charged | 615.4 | 707.4 | 2/y6 |
| DEAVLFQPGSR | 609.8 | 804.4 | 2/y7 |
| (SEQ ID NO: 155) | 609.8 | 903.5 | 2/y8 |
| doubly-charged | 609.8 | 691.4 | 2/y6 |

TABLE 15

| Hazelnuts Proteins | Q1 | Q3 | Fragment Ion |
|---|---|---|---|
| YFGECNLDR | 581.7 | 666.3 | 2/y5 |
| (SEQ ID NO: 156) | 581.7 | 852.3 | 2/y7 |
| doubly-charged | 581.7 | 999.4 | 2/y8 |
| LNALEPTNR | 514.3 | 729.4 | 2/y6 |
| (SEQ ID NO: 157) | 514.3 | 800.4 | 2/y7 |
| doubly-charged | 514.3 | 914.5 | 2/y8 |
| TIEPNGLLLPQYSNAPELIYIER | 881.8 | 1032.6 | 3/y8 |
| (SEQ ID NO: 158) | 881.8 | 580.3 | 3/y4 |
| triply-charged | 881.8 | 806.5 | 3/y6 |
| HFYLAGNPDDEHQR | 566.9 | 448.8 | 3/y7(2) |
| (SEQ ID NO: 159) | 566.9 | 684.3 | 3/y5 |
| triply-charged | 566.9 | 799.3 | 3/y6 |
| QGQQQFGQR | 538.8 | 763.4 | 2/y6 |
| (SEQ ID NO: 160) | 538.8 | 948.5 | 2/y8 |
| doubly-charged | 538.8 | 635.3 | 2/y5 |
| QEWER | 374.2 | 619.3 | 2/y4 |
| (SEQ ID NO: 161) | 374.2 | 490.2 | 21y3 |
| doubly-charged | 374.2 | 304.2 | 2/y2 |
| ADIYTEQVGR | 576.3 | 689.4 | 2/y6 |
| (SEQ ID NO: 162) | 576.3 | 852.4 | 21y7 |
| doubly-charged | 576.3 | 588.3 | 2/y5 |
| INTVNSNTLPVLR | 720.9 | 899.5 | 2/y8 |
| (SEQ ID NO: 163) | 720.9 | 1013.6 | 2/y9 |
| doubly-charged | 720.9 | 484.3 | 2/y4 |
| WLQLSAER | 501.8 | 703.4 | 2/y6 |
| (SEQ ID NO: 164) | 501.8 | 816.5 | 21y7 |
| doubly-charged | 501.8 | 575.3 | 2/y5 |
| QGQVLTIPQNFAVAK | 807.5 | 874.5 | 2/y8 |
| (SEQ ID NO: 165) | 807.5 | 987.6 | 2/y9 |
| doubly-charged | 807.5 | 1088.6 | 2/y10 |

TABLE 15-continued

| Hazelnuts Proteins | Q1 | Q3 | Fragment Ion |
|---|---|---|---|
| AESEGFEWVAFK | 700.3 | 983.5 | 2/y8 |
| (SEQ ID NO: 166) | 700.3 | 464.3 | 2/y4 |
| doubly-charged | 700.3 | 365.2 | 2/y3 |
| TNDNAQISPLAGR | 678.9 | 841.5 | 2/y8 |
| (SEQ ID NO: 167) | 678.9 | 600.4 | 2/y6 |
| doubly-charged | 678.9 | 713.4 | 2/y7 |
| ALPDDVLANAFQISR | 815.4 | 906.5 | 2/y8 |
| (SEQ ID NO: 168) | 815.4 | 835.4 | 2/y7 |
| doubly-charged | 815.4 | 723.6 | 2/y13(2) |
| QETTLVR | 423.7 | 589.4 | 2/y5 |
| (SEQ ID NO: 169) | 423.7 | 718.4 | 2/y6 |
| doubly-charged | 423.7 | 488.3 | 2/y4 |
| VEEIDHANFK | 601.3 | 973.5 | 2/y8 |
| (SEQ ID NO: 170) | 601.3 | 616.3 | 2/y5 |
| doubly-charged | 601.3 | 731.4 | 2/y6 |
| AVEAYLLAHPDAYC | 791.4 | 935.4 | 2/y8 |
| (SEQ ID NO: 171) | 791.4 | 1211.5 | 2/y10 |
| doubly-charged | | | |
| AVEAYLLAHPDAYC | 527.9 | 614.2 | 3/y5 |
| (SEQ ID NO: 172) | | | |
| triply-charged | | | |

TABLE 16

| Macadamia Proteins | Q1 | Q3 | Fragment Ion |
|---|---|---|---|
| QCMQLETSGQMR | 729.3 | 921.5 | 2/y8 |
| (SEQ ID NO: 173) | 729.3 | 1049.5 | 2/y9 |
| doubly-charged | | | |
| CVSQCDK | 437.7 | 626.2 | 2/y5 |
| (SEQ ID NO: 174) | 437.7 | 725.3 | 2/y6 |
| doubly-charged | | | |
| FEEDIDWSK | 584.8 | 892.4 | 2/y7 |
| (SEQ ID NO: 175) | 584.8 | 763.4 | 2/y6 |
| doubly-charged | | | |
| HMQICQQR | 545.2 | 821.4 | 2/y6 |
| (SEQ ID NO: 176) | 545.2 | 952.4 | 2/y7 |
| doubly-charged | | | |
| HCEQQEPR | 536.7 | 786.4 | 2/y6 |
| (SEQ ID NO: 177) | 536.7 | 935.4 | 2/y7 |
| doubly-charged | | | |
| LQYQCQR | 492.7 | 743.3 | 2/y5 |
| (SEQ ID NO: 178) | 492.7 | 580.2 | 2/y4 |
| doubly-charged | | | |
| EGVIIR | 343.7 | 500.4 | 2/y4 |
| (SEQ ID NO: 179) | 343.7 | 401.3 | 2/y3 |
| doubly-charged | | | |
| ESEFDR | 391.7 | 566.3 | 2/y4 |
| (SEQ ID NO: 180) | 391.7 | 437.2 | 2/y3 |
| doubly-charged | | | |
| QQYQCQR | 500.2 | 743.3 | 2/y5 |
| (SEQ ID NO: 181) | 500.2 | 580.2 | 2/y4 |
| doubly-charged | | | |

TABLE 17

| Peanut Proteins | Q1 | Q3 | Fragment Ion |
|---|---|---|---|
| NLPQQCGLR | 543.3 | 858.4 | 2/y7 |
| (SEQ ID NO: 182) | 543.3 | 429.7 | 2/y7(2) |
| doubly-charged | 543.3 | 633.3 | 2/y5 |
| NNPFYFPSR | 571.3 | 913.5 | 2/y7 |
| (SEQ ID NO: 183) | 571.3 | 669.3 | 2/y5 |
| doubly-charged | 571.3 | 506.3 | 2/y4 |
| TANDLNLLILR | 628.4 | 854.6 | 2/y7 |
| (SEQ ID NO: 184) | 628.4 | 741.5 | 2/y6 |
| doubly-charged | 628.4 | 514.4 | 2/y4 |
|  | 628.4 | 969.6 | 2/y8 |
| DLAFPGSGEQVEK | 688.8 | 833.4 | 2/y8 |
| (SEQ ID NO: 185) | 688.8 | 930.5 | 2/y9 |
| doubly-charged | 688.8 | 1077.5 | 2/y10 |
| SPDIYNPQAGSLK | 695.4 | 700.4 | 2/y7 |
| (SEQ ID NO: 186) | 695.4 | 814.4 | 2/y8 |
| doubly-charged | 695.4 | 977.5 | 2/y9 |
| VLLEENAGGEQEER | 786.9 | 804.4 | 2/y7 |
| (SEQ ID NO: 187) | 786.9 | 989.4 | 2/y9 |
| doubly-charged | 786.9 | 1118.5 | 2/y10 |

TABLE 18

| Pistachio Proteins | Q1 | Q3 | Fragment Ion |
|---|---|---|---|
| CAGVAVAR | 396.7 | 515.3 | 2y5 |
| (SEQ ID NO: 188) | 396.7 | 572.4 | 2y6 |
| doubly-charged | 396.7 | 416.3 | 2y4 |
| HTIQPNGLR | 518.3 | 556.3 | 2y5 |
| (SEQ ID NO: 189) | 518.3 | 797.5 | 2y7 |
| doubly-charged |  |  |  |
| ILAEVFQVEQSLVK | 802.0 | 1077.6 | 2y9 |
| (SEQ ID NO: 190) | 802.0 | 802.5 | 2y7 |
| doubly-charged | 802.0 | 930.5 | 2y8 |
| GFESEEESEYER | 745.8 | 1157.5 | 2y9 |
| (SEQ ID NO: 191) | 745.8 | 941.4 | 2y7 |
| doubly-charged | 745.8 | 683.3 | 2y5 |
| SDIYTPEVGR | 568.8 | 821.4 | 2y7 |
| (SEQ ID NO: 192) | 568.8 | 557.3 | 2y5 |
| doubly-charged | 568.8 | 658.4 | 2y6 |
| ITSLNSLNLPILK | 713.4 | 1011.6 | 2y9 |
| (SEQ ID NO: 193) | 713.4 | 470.3 | 2y4 |
| doubly-charged |  |  |  |
| WLQLSAER | 501.8 | 703.4 | 2y6 |
| (SEQ ID NO: 194) | 501.8 | 816.5 | 2y7 |
| doubly-charged | 501.8 | 575.3 | 2y5 |
| FEWISFK | 478.8 | 680.4 | 2y5 |
| (SEQ ID NO: 195) | 478.8 | 809.4 | 2y6 |
| doubly-charged | 478.8 | 381.2 | 2y3 |
| AMISPLAGSTSVLR | 701.9 | 790.4 | 2y8 |
| (SEQ ID NO: 196) | 701.9 | 903.5 | 2y9 |
| doubly-charged | 701.9 | 1087.6 | 2y11 |
| AMPEEVLANAFQISR | 838.4 | 1019.6 | 2y9 |
| (SEQ ID NO: 197) | 838.4 | 835.4 | 2y7 |
| doubly-charged | 838.4 | 906.5 | 2y8 |
| FQTQC[MSH]QIQNLNALEPK | 961.0 | 1026.6 | 2y9 |
| (SEQ ID NO: 198) | 961.0 | 898.5 | 2y8 |
| doubly-charged | 961.0 | 671.4 | 2y6 |

TABLE 18-continued

| Pistachio Proteins | Q1 | Q3 | Fragment Ion |
|---|---|---|---|
| IESEAGVTEFWDQNEEQLQC[MSH]ANVAVFR | 790.4 | 1053.5 | 4y9 |
| (SEQ ID NO: 199) | 790.4 | 492.3 | 4y4 |
| doubly-charged | 790.4 | 925.4 | 4y8 |
| LVLVALADVGNSENQLDQYLR | 777.4 | 694.4 | 3y5 |
| (SEQ ID NO: 200) | 777.4 | 807.4 | 3y6 |
| triply-charged | 777.4 | 579.3 | 3y4 |
| GIIVR | 279.2 | 500.4 | 2y4 |
| (SEQ ID NO: 201) | 279.2 | 274.2 | 2y2 |
| doubly-charged |  |  |  |
| GLPLDVIQNSFDISR | 837.5 | 1079.6 | 2y9 |
| (SEQ ID NO: 202) | 837.5 | 966.5 | 2y8 |
| doubly-charged | 837.5 | 752.6 | 2y13(2) |
| SEMTIFAPGSR | 598.3 | 747.4 | 2y7 |
| (SEQ ID NO: 203) | 598.3 | 848.5 | 2y8 |
| doubly-charged | 598.3 | 634.3 | 2y6 |

TABLE 19

| Walnut Proteins | Q1 | Q3 | Fragment Ion |
|---|---|---|---|
| QQNLNHCQYYLR | 813.4 | 1142.5 | 2y8 |
| (SEQ ID NO: 204) |  |  |  |
| doubly-charged |  |  |  |
| QCCQQLSQMDEQCQCEGLR | 805.3 | 900.3 | 3y7 |
| (SEQ ID NO: 205) | 805.3 | 623.3 | 3y5 |
| triply-charged | 805.3 | 345.2 | 3y3 |
| GEEMEEMVQSAR | 698.3 | 820.4 | 2y7 |
| (SEQ ID NO: 206) | 698.3 | 949.4 | 2y8 |
| doubly-charged | 698.3 | 461.3 | 2y4 |
| DLPNECGISSQR | 682.8 | 1136.5 | 2y10 |
| (SEQ ID NO: 207) | 682.8 | 796.3 | 2y7 |
| doubly-charged | 682.8 | 925.4 | 2/y8 |
|  | 682.8 | 1039.4 | 2/y9 |
|  | 682.8 | 568.7 | 2/y10(2) |
| LDALEPTNR | 514.8 | 729.4 | 2/y6 |
| (SEQ ID NO: 208) | 514.8 | 487.3 | 2/y4 |
| doubly-charged | 514.8 | 616.3 | 2/y5 |
| GLGNNVFSGFDADFLADAFNVDTETAR | 955.1 | 692.3 | 3/y6 |
| (SEQ ID NO: 209) | 955.1 | 905.4 | 3/y8 |
| triply-charged | 955.1 | 577.3 | 3/y5 |
| WLQLSAER | 501.8 | 703.4 | 2/y6 |
| (SEQ ID NO: 210) | 501.8 | 816.5 | 2/y7 |
| doubly-charged | 501.8 | 575.3 | 2/y5 |
| ALPEEVLATAFQIPR | 792.4 | 903.5 | 2/y8 |
| (SEQ ID NO: 211) | 792.4 | 1016.6 | 2/y9 |
| doubly-charged |  |  |  |
| ALPEEVLATAFQIPR | 528.6 | 1016.6 | 3/y9 |
| (SEQ ID NO: 212) |  |  |  |
| triply-charged |  |  |  |

In some embodiments, two or more of the above allergens can be detected and/or quantified by detecting, via LC-MS/MS, one or more peptides specific for each allergen, such as those discussed above, where for each peptide multiple MRM transitions, such as those discussed above, can be monitored. In one embodiment, for example, egg proteins can be detected in a sample by monitoring multiple MRM transitions for two peptides specific to ovalbumin (e.g., monitoring the MRM transitions of 930/1116, 930/888, and 930/1017 for the peptide having the amino acid sequence of SEQ. ID NO. 1 and monitoring the MRM transitions 390/667, 390/504, and 390/433 for the peptide having the amino acid sequence of SEQ. ID NO. 7) and one peptide specific to lysozyme (e.g., monitoring the MRM transitions of 437/452, 437/680, and 437/737 for the peptide having the amino acid sequence of SEQ. ID NO. 8). In one embodiment, for example, milk proteins can be detected in a sample by monitoring multiple MRM transitions for two peptides specific to casein isoform S1 (e.g., monitoring the MRM transitions of 693/920, 693/991, and 693/1090 for the peptide having the amino acid sequence of SEQ. ID NO. 12 and monitoring the MRM transitions of 880/1324, 880/436, 587/758, 587/871, and 587/790 for the peptide having the amino acid sequence of SEQ. ID NO. 16), one peptide specific to casein isoform S2 (e.g., monitoring the MRM transitions of 598/911 and 598/456 for the peptide having the amino acid sequence of SEQ. ID NO. 20), and one specific to lactoglobulin (e.g. monitoring the MRM transitions of 623/1047, 623/918, 623/819 for the peptide having the amino acid sequence of SEQ. ID NO. 27). In other embodiments, any combination of any of the allergens disclosed in Tables 1 to 19 can be detected and/or quantified using similar procedures.

According to some embodiments, a kit for use in the mass spectrometric testing of a sample for at least one of ovalbumin, lysozyme, casein, lactoglobulin, high or low glutenins, and proteins from wheat, rye, oats, barley, mustard, sesame and various nuts including macadamia, pistachio, brazil, walnuts, peanuts and hazelnuts is provided. The kit can include one or more isolated peptides specific to chicken ovalbumin, chicken lysozyme, bovine casein, or bovine lactoglobulin, high or low glutenins, wheat, rye, oats, barley, mustard, sesame and various nuts including macadamia, pistachio, brazil, walnuts, peanuts and hazelnuts. For example, the kit can include one or more isolated ovalbumin-specific peptides having the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7. In one aspect, the kit can include one or more isolated lysozyme-specific peptides having the amino acid sequence of SEQ ID NO: 8, SEQ ID NO: 9, SEQ ID NO: 10, or SEQ ID NO: 11. In one embodiment, the kit can include one or more isolated casein-specific peptides. For example, the kit can include one or more isolated peptides specific to the S1 isoform of casein, such as those peptides having the amino acid sequence of SEQ ID NO: 12, SEQ ID NO: 13, SEQ ID NO: 14, SEQ ID NO: 15, SEQ ID NO: 16, SEQ ID NO: 17, or SEQ ID NO: 18. Alternatively or in addition, the kit can include one or more isolated peptides specific to the S2 isoform of casein, such as those peptides having the amino acid sequence of SEQ ID NO: 19, SEQ ID NO: 20, SEQ ID NO: 21, SEQ ID NO: 22, or SEQ ID NO: 23. In one embodiment, the kit can include one or more isolated lactoglobulin-specific peptides having the amino acid sequence of SEQ ID NO: 24, SEQ ID NO: 25, SEQ ID NO: 26, SEQ ID NO: 27, SEQ ID NO: 28, or SEQ ID NO: 29. In some embodiments, the kit can comprise at least one isolated peptide specific to each of ovalbumin, lysozyme, casein (S1 and/or S2), lactoglobulin, high or low glutenins, and proteins from wheat, rye, oats, barley, mustard, sesame and various nuts including macadamia, pistachio, brazil, walnuts, peanuts and hazelnuts. For example, the kit can comprise one of each of the isolated peptides corresponding to SEQ ID NOS: 1-212 identified herein. Alternatively, the kit can comprise one peptide selected from the group corresponding to SEQ ID NOS. 1-7, one peptide selected from the group corresponding to SEQ ID NOS. 8-11, peptide selected from the group corresponding to SEQ ID NOS. 12-18, one peptide selected from the group corresponding to SEQ ID NOS. 19-23, one peptide selected from the group corresponding to SEQ ID NOS. 24-29 and one peptide selected from each of the allergens in Tables 6-19. In some embodiments, the peptides can be isotopically labeled (e.g., using $^{15}N$, $^{13}C$). In other embodiments, one or more peptides can be chosen from some, but not all of the allergens disclosed herein.

According to some embodiments, a kit for use in the mass spectrometric testing of a sample for at least one of ovalbumin, lysozyme, casein, lactoglobulin, high or low glutenins, and proteins from wheat, rye, oats, barley, mustard, sesame and various nuts including macadamia, pistachio, brazil, walnuts, peanuts and hazelnuts is provided. The kit can include, for example, at least one proteolytic enzyme for fragmenting one or more of ovalbumin, lysozyme, casein, lactoglobulin, high or low glutenins and proteins from wheat, rye, oats, barley, mustard, sesame and various nuts including macadamia, pistachio, brazil, walnuts, peanuts and hazelnuts into a plurality of peptides. For example, the proteolytic enzyme can be effective to fragment the allergens into a plurality of peptides, at least one of which has the amino acid sequence of SEQ ID NOS. 1-212. The kit can also include at least one reagent for quantifying at least one of the plurality of peptides having an amino acid sequence of SEQ ID NO: 1-212 using a mass spectrometer.

Various processes and reagents can be effective to prepare the sample for mass spectrometric analysis and/or fragment the allergens into a plurality of peptides. For example, in one exemplary embodiment, the proteolytic enzyme can be trypsin that can lyse the allergens into a plurality of peptides. In some embodiments, the kit can include an LC column on which a proteolytic enzyme, such as trypsin, is immobilized. The kit can also comprise digestion components, including buffers enzymes, alkylating agents, reducing agents, and optionally, other reagents and/or components. In some embodiments, the kit can comprise, for example, a homogeneous assay such that the user need only add a sample.

In some embodiments, the kit can comprise calibration or normalization reagents or standards. For example, the kit can comprise at least one peptide specific to each of ovalbumin, lysozyme, casein (S1 and/or S2), lactoglobulin, high or low glutenins and proteins from wheat, rye, oats, barley, mustard, sesame and various nuts including macadamia, pistachio, brazil, walnuts, peanuts and hazelnuts for calibrating the quantitation of the allergen-specific peptides. By way of non-limiting example, the kit can contain solutions for each of the allergen-specific peptides at known concentrations such that a calibration curve can be constructed. In some embodiments, the kit can contain at least one of the allergens of interest (e.g., ovalbumin, lysozyme, casein, lactoglobulin, high or low glutenins and proteins from wheat, rye, oats, barley, mustard, sesame and various nuts including macadamia, pistachio, brazil, walnuts, peanuts and hazelnuts) for calibrating the quantitation of the allergen-specific peptides or the allergen(s) themselves. For example, the kit can include a known amount of each of ovalbumin, lysozyme, casein, lactoglobulin, high or low glutenins and proteins from wheat, rye, oats, barley, mustard, sesame and various nuts including macadamia, pistachio, brazil, walnuts, peanuts and hazelnuts. Alternatively or in addition, calibration can be performed by spiking the sample with at least one isotopically-enriched peptide having the same amino acid sequence as that a peptide of interest. Accordingly, the kit can include one or more isotopically-enriched peptides corresponding to each or some of SEQ ID NOS. 1-212.

According to some embodiments, different transitions can be used to measure and benchmark assay results, depending on various factors. Accordingly, the kit can comprise different transition values and/or suggested settings, useful for enabling comparative measurements between a sample and one or more control reagents. The kit can include information relating to Q1 and Q3 transition values for each of the allergen-specific peptides. For example, in one embodiment, the kit can comprise each of the isolated peptides of SEQ ID NOS: 1-2 identified herein, and further can comprise instructions for quantifying the at least one of the peptides using a mass spectrometer. Information pertaining to instrument settings that can or should be used to perform an assay can also be included in the kit. Information pertaining to sample preparation, operating conditions, volumetric amounts, temperature settings, and the like, can be included with the kit.

According to some embodiments, different transitions can be used to measure and benchmark assay results, depending on various factors. Accordingly, the kit can comprise different transition values and/or suggested settings, useful to make comparative measurements between a sample and one or more control reagents. The kit can include instructions to measure specific pairs of transition values, for example, the Q1/Q3 transition pair, or the values of one or more different transition pairs.

The kit can be packaged in a hermetically sealed container containing one or more reagent vessels and appropriate instructions. An electronic medium can also be contained within the kit and can store and/or provide electronic information pertaining to one or more assays, measurement values, transition pairs, operating instructions, software for carrying out operations, a combination thereof, or the like.

According to some aspects, software is provided which can control the processes and/or perform the calculations described herein. For example, the software can provide instructions to a mass spectrometer to monitor one or more specific precursor-product ion pair transitions.

The software can include modules for generating calibration data, e.g., based on mass spectrometric analysis of calibrations standards provided with a kit, and modules for receiving and analyzing mass spectrometric data (e.g., LC-MS/MS data) to identify one or more of the above peptides and MRM transitions. Upon identification of one or more peptides specific to one of the above allergens, the software can utilize the calibration data to quantify those peptides and the associated allergen.

In other embodiments, a method is provided in which screening a sample for an allergen can be achieved, comprising: obtaining a sample; digesting the sample with at least one proteolytic enzyme to fragment at least one allergen present in the sample, if any, into a plurality of peptides, wherein said at least one allergen is selected from the group consisting of ovalbumin, lysozyme, casein, lactoglobulin, high molecular weight gluten, low molecular weight gluten, wheat, rye, oats, barley, mustard, sesame, macadamia nuts, pistachio nuts, brazil nuts, walnuts, peanuts and hazelnuts; and quantifying at least one of said allergens present in the sample by determining an amount of at least one said plurality of peptides using liquid chromatography tandem mass spectrometry (LC-MS/MS), wherein at least one of said plurality of peptides comprises a peptide having an amino acid sequence of SEQ ID NOS: 1-212. In other embodiments, two or more of the allergens are quantified. In another embodiment, two or more of said plurality of peptides is determined to quantify said at least one of said allergens. In another embodiment, at least one selected MRM transition is monitored for each of said plurality of peptides. In an alternative embodiment, two or more selected MRM transitions are monitored for each of said plurality of peptides. In yet another embodiment, the proteolytic enzyme is trypsin.

EXAMPLES

Figure 1:
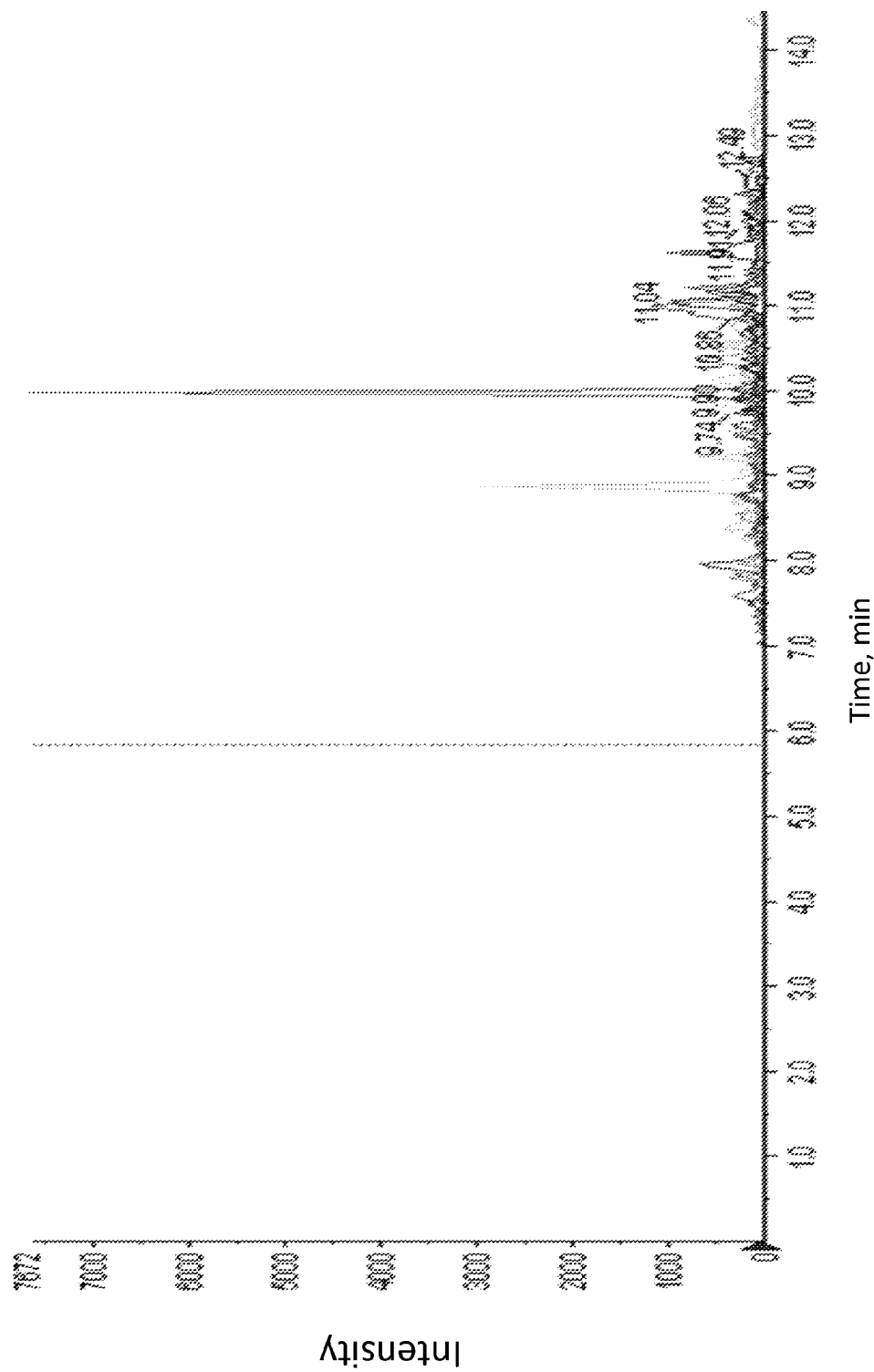
FIG. 1 shows an exemplary chromatogram resulting from an exemplary "blank" sample of bread.
Figure 2:
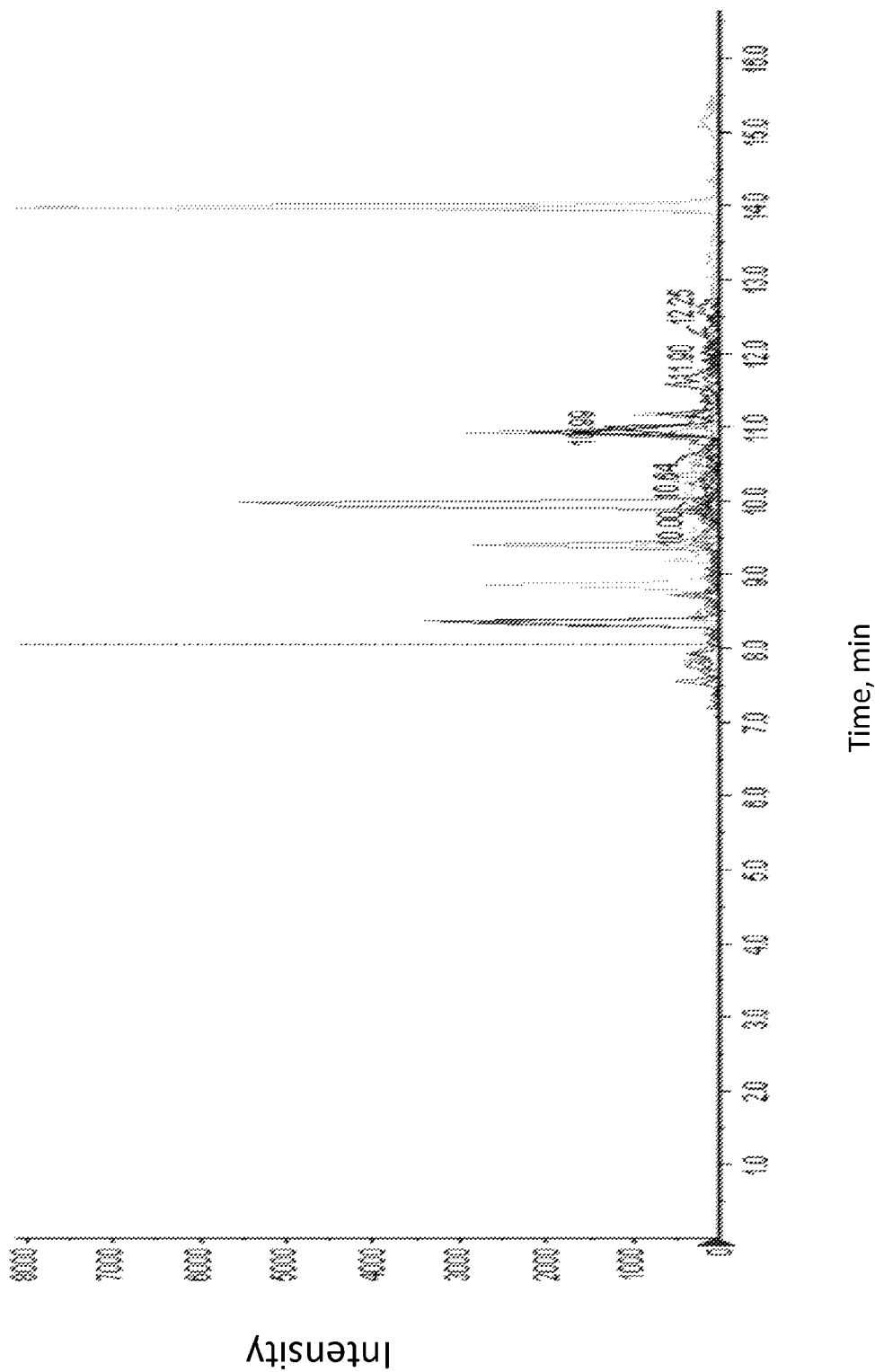
FIG. 2 shows an exemplary chromatogram resulting from a bread sample spiked with milk, and containing milk peptides.
Figure 3A:
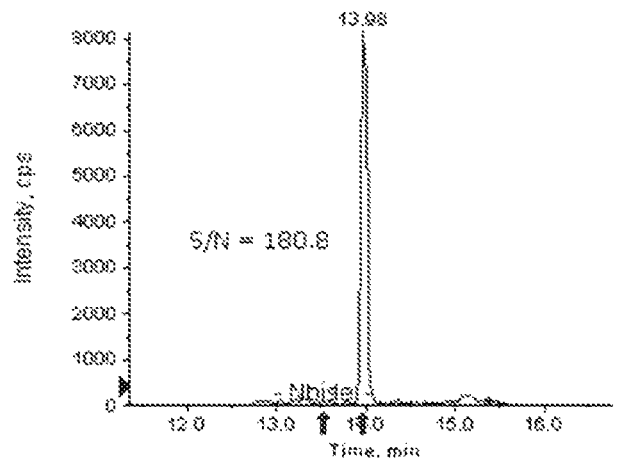
FIGS. 3A, 3B, 3C depict the signals obtained for three specific milk peptides.
Figure 3B:
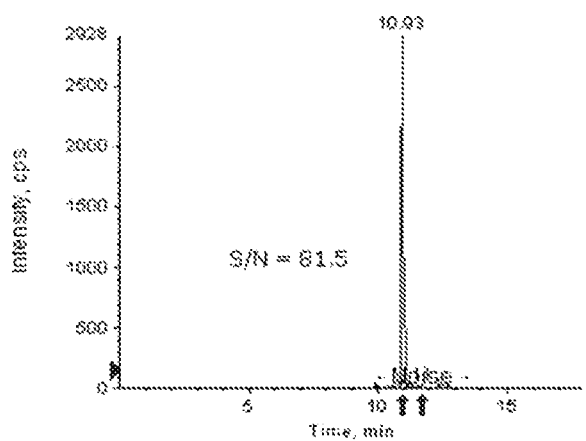
Figure 3C:
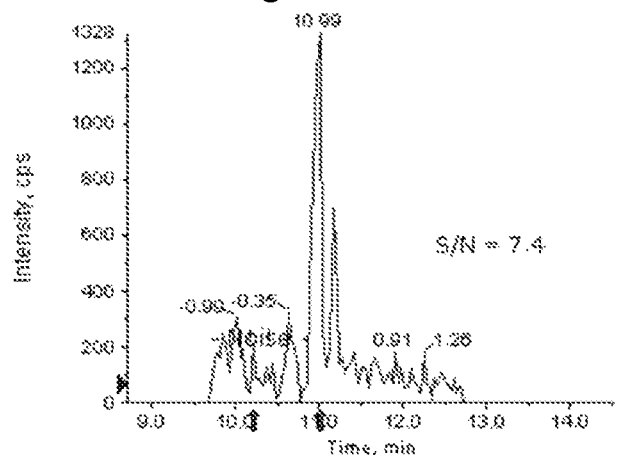

The applicants' teachings can be even more fully understood with reference to the examples and resulting data that follow. Other embodiments of the applicants' teachings will be apparent to those skilled in the art from consideration of the present specification and practice of the present teachings disclosed herein. It is intended that these examples be considered as exemplary only.

Example 1

Preparation of Solutions

Extraction Buffer—Tris (2-Amino-2-hydroxymethyl-propane-1,3-diol, 3.03 g) and Urea (60 g) were dissolved into water (480 mL) make a 50 mM Tris buffer/2 M Urea extraction solvent. The resulting solution had a pH of approximately 10.

Digestion Buffer—Ammonium bicarbonate (3.16 g) was dissolved in water (400 mL). The resulting solution had a pH of approximately 7.8.

Enzyme solution—Trypsin (1 g) was dissolved in digestion buffer (20 mL) to make a stock solution at a concentration of 50 mg/mL. The stock solution (100 μL) was further diluted into 10 mL of digestion buffer to make a final trypsin solution of 500 μg/mL solution. All enzyme solution were frozen at −20° C. (or lower) for storage and thawed prior to use.

Iodoacetamide solution—Iodoacetamide (0.925 g) was added to 10 mL of water and sonicated to dissolve the solid. The 0.5M iodoacetamide solution was prepared fresh prior to use and discarded after use.

Preparation of Mixed Allergen spike solution—20.0 mg (0.0200 g) of each protein (Egg lysozyme, Egg albumin, Milk α-casein, and Milk β-lactoglobulin) is dissolved in 10.0 mL of extraction buffer in a 15 mL polypropylene centrifuge tube to make a combined spiking solution containing 2000 µg/mL of each allergen. The resulting Mixed Allergen Spiking solution is stable for 1 month when stored in a refrigerator. Longer term stability has not been determined.

Sample Preparation

As discussed above, the samples can be derived from a variety of sources. In this example, the sample was obtained from dry baked foodstuffs. Finely powdered sample (5.0 g) was mixed in a centrifuge tube (50 mL) with 30 mL of extraction buffer and the mixture was broken up by vigorous shaking and agitated further using a roller mixer (60 minutes). The centrifuge tubes were spun down for 5 minutes at 3500 rpm and 15° C. 200 µL of 1M DTT solution is added to 6 mL of the supernatant. The samples were mixed and heated for 60 minutes at 37° C. The samples were then cooled to room temperature and 2.0 mL of freshly prepared 0.5M iodoacetamide solution in water was added. The samples were shaken to mix and stored protected from light (30 minutes at room temperature). To each sample, 6 mL of digestion buffer (0.1M ammonium bicarbonate) was added, followed by 400 µL of trypsin enzyme solution (200 µg total enzyme per sample). The samples were incubated overnight at 37° C. The samples were centrifuged (5 minutes, 10° C. at 3000 rpm) and filtered through 0.45µ RC filter. The filtrate was acidified with 0.5 mL of formic acid.

Strata™ X SPE cartridges were conditioned with 6 mL of acetonitrile containing 0.1% formic acid followed with 6 mL of water containing 0.5% TFA (trifluoroacetic acid). Supernatant from the centrifuged samples were loaded onto the SPE cartridges at a rate of 1-2 drops per second. The SPE cartridges were washed with 3 mL of 0.5% TFA in water. Allergen peptides were eluted with 6 mL of acetonitrile and evaporated to dryness using a centrifugal evaporator.

The sample residue was reconstituted by adding 300 µL of a water/acetonitrile solution (95% water with 5% acetonitrile and 0.5% formic acid). The samples were vortexed for 20-30 seconds and sonicated for 30 minutes to complete dissolution of material. The contents were transferred to a 1.5 mL Eppendorf tube and centrifuged (5 minutes at 13000 rpm). The supernatant was removed and transferred to a 300 µL polypropylene HPLC vial with press fit cap for HPLC analysis.

Chromatography was performed using a Shimadzu Prominence LC system using a Phenomenex Analytical Column, 4 µm, Synergi Hydro-RP 80A Column 150×2.1 mm using a mobile phase solutions of 1.00 ml of formic acid in 999 ml of water and 1.00 ml of formic acid in 999 ml of acetonitrile. Flow rate was 0.300 ml/min at a column oven temperature of 30 C.

Samples were analyzed on an Applied Biosystems 4000QTRAP® LC/MS/MS system using a TurboIonSpray® ion source. The compounds were analyzed using scheduled MRM (sMRM) with a MRM detection window of 90 s and a target scan time of 0.40 s. Q1 was set to low and Q3 was set to unit resolution to obtain maximum signal response.

Example 2

Another method to prepare the samples is described in which in this example. A NANOSEP 10k OMEGA (100/pk) and a Phenex RC membrane, 0.45 µm, 26 mm syringe filters. In addition, the following HPLC Solvents and Consumables were utilized: Water, Methanol (MeOH), Acetonitrile (CAN), 50 mL polypropylene centrifuge tubes, 15 mL polypropylene centrifuge tubes, Disposable glass culture tubes (13×100 mm), Polypropylene microcentrifuge tubes (1.5 mL), Conical polypropylene HPLC vials and caps (300 µL), Disposable syringe, 10 mL capacity, luer end. Furthermore, the following equipment was necessary for extractions and sample processing: Ultracentrifuge for 50 mL tubes, Microcentrifuge for 1.5 mL tubes, SPE manifold for sample processing (with vacuum pump), Forced air incubator (set to 37° C.), roller shaker, Centrifugal evaporator/concentrator.

Preparation of Solutions

Extraction Buffer—Tris (2-amino-2-hydroxymethyl-propane-1,3-diol, 3.03 g) and urea (60 g) was dissolved into water (480 ml) and stirred until complete dissolution to make a 50 mM Tris buffer/2 M Urea extraction solvent.

Digestion Buffer—Ammonium bicarbonate (3.16 g) was dissolved in water (378 mL). To this was added 2 ml of 1M calcium chloride and 20 ml of acetonitrile. The pH was approximately 7.8.

Enzyme solution—Trypsin (1 g) was dissolved in digestion buffer (20 mL) to make a stock solution at a concentration of 50 mg/mL. The stock solution (100 µL) was further diluted into 10 mL of digestion buffer to make a final trypsin solution of 500 µg/mL solution. All enzyme solution were frozen at −20° C. (or lower) for storage and thawed prior to use.

Preparation of Individual Allergen Stock Solution—A 10 mg/ml stock solution was prepared by dissolving 30.0 mg each of egg albumin, milk casein and lactoglobulin) in 3.0 ml of extraction buffer in a 5 ml Eppendorf tube. The resulting allergen stock solutions were stable for three months when stored at −20 C or lower, though longer term stability has not been determined.

Preparation of Mixed Allergen spike solution—1.0 ml of each allergen stock solution (10 mg/ml) (egg albumin, mile casein and milk lactoglobulin) is transferred into a 5 ml Eppendorf tube and to this 2.0 ml of the extraction buffer was added and mixed. The mixed allergen stock solution contained 2 mg/ml of each allergen and is stable for one month when stored at −20 C or lower though longer term stability has not been determined.

Preparation of Mixed Allergen Spike Solution—100 µL of the mixed allergen stock solution (2 mg/ml) was added to a 2 mL eppendorf tube containing 900 µL of the extraction buffer. The resulting solution contained 200 µg/ml of each allergen protein.

Sample Preparation 1.00 g of a finely powdered sample was weighed into a 15 ml centrifuge tube. Serial addition calibration samples from each individual sample were prepared from each individual samples following table 20.

TABLE 20

| Calibration Standard | Sample Weight (g) | Spike Solution Used | Spike Volume (µL) | Extraction Buffer Volume (mL) |
|---|---|---|---|---|
| Sample | 1.00 | Mixed Allergens | 0 | 6.00 |
| Sample + 4 ppm | 1.00 | Mixed Allergens | 20 | 5.98 |
| Sample + 10 ppm | 1.00 | Mixed Allergens | 50 | 5.95 |
| Sample + 40 ppm | 1.00 | Mixed Allergens | 200 | 5.80 |
| Sample + 100 ppm | 1.00 | Mixed Allergens | 500 | 5.50 |

Each mixture was shaken vigorously to break the mixture down and then agitated further for 60 minutes using a roller mixer. The centrifugal tubes were spun down for 20 minutes at 3500 rpm and 15 C. 500 µL of each supernatant was added to a 2 ml eppendorf tube and 50 µL of TCEP solution and vortex mixed in incubated for 60 minutes at 60 C. The tubes were then allowed to cool to room temperature at 25 µL of MMTS were added, vortexed again to mix and incubated for 10 minutes. 500 µL of digestion buffer were added to each sample followed by 20 µL of trypsin enzyme solution (containing 20 µf total enzyme per sample). Solution was mixed thoroughly by vortex. The samples were then incubated overnight at 37 C. The next day 30 µL of formic acid was added to each sample and mixed well. The samples were then centrifuged for 5 minutes at 13000 rpm. 500 µL of the supernatant were taken into a 10K-MwCO filter and centrifuged for 20 minutes at 13000 rpm. 200 µL of the filtrate were transferred into an appropriate polypropylene HPLC autosampler vial for LC/MS/MS analysis with the remainder being stored at −20 C for further analysis if necessary.

Chromatography was performed using a Shimadzu Prominence LC system using a Phenomenex Analytical Column, 4 µm, Synergi Hydro-RP 80A Column 150×2.1 mm using a mobile phase solutions of 1.00 ml of formic acid in 999 ml of water and 1.00 ml of formic acid to 999 ml of acetonitrile. The system also consisted of System controller (CBM-20A), 2 Isocratic pumps LC-20AD (with semi-micro 50 µL mixer), an Autosampler SIL-20AC and a Column oven CTO-20AC. In addition, a Guard Column (Phenomenex trap cartridge, 4 µm, Synergi Hydro-RP 80A Mercury, 20×2.0 mm), a cartridge holder (Phenomenex MercuryMS 20 mm Cartridge Holder) were utilizes and a needle rinse of 95:5 (v:v) acetonitrile: water+0.05% TFA was utilized with a Flow Rate: 0.300 mL/min, Equilibration time: 0.5 min, Column oven temperature: 30° C., and an Injection volume: 30 µL. The Autosampler needle rinse sequence included Rinsing Volume: 1000 µL, Needle stroke: 52 mm, Rinsing speed: 35 µL/sec, Sampling speed: 2.0 µL/sec, Rinse dip time: 5 sec, Rinse mode: Before and after aspiration.

Samples were analyzed on an Applied Biosystems 4000QTRAP® LC/MS/MS system using a TurboIonSpray® ion source with positive polarity. The compounds were analyzed using scheduled MRM (sMRM) with a MRM detection window of 90 s and a target scan time of 0.40 s. Q1 was set to low and Q3 was set to unit resolution to obtain maximum signal response. Other parameters utilizes included Source/Gas Parameters IS: 5500, CUR: 30 psi, TEM: 500° C., GS1: 35 psi, GS2: 46 psi, Ihe: On, and CAD: High.

The Compound MRM Parameters and Retention Times included DP: variable, EP: 10, CXP: variable, Dwell time: variable, Q1 Resolution: LOW, Q3 and Resolution: UNIT Calibration curves were derived from absolute peak areas using a least squares regression of the area versus the nominal concentrations of the serial spiked samples. Deviations from the regression line are calculated by using the regression equation to back calculate the concentration at each spiking level. Concentrations of target peptides are obtained from the regression curves calculated from the apparent concentration of the unspiked samples. The linear ranges for each of the egg albumin, egg lysozyme, milk casein and lactoglobulin ranges between 10 and 100 µg/g Each sample has its own linear range for quantitation. Calibration standards in the full calibration curve should be excluded from the regression to meet the applicable range. The calibration curves are depicted in FIGS. 5 to 9.

Figure 5:
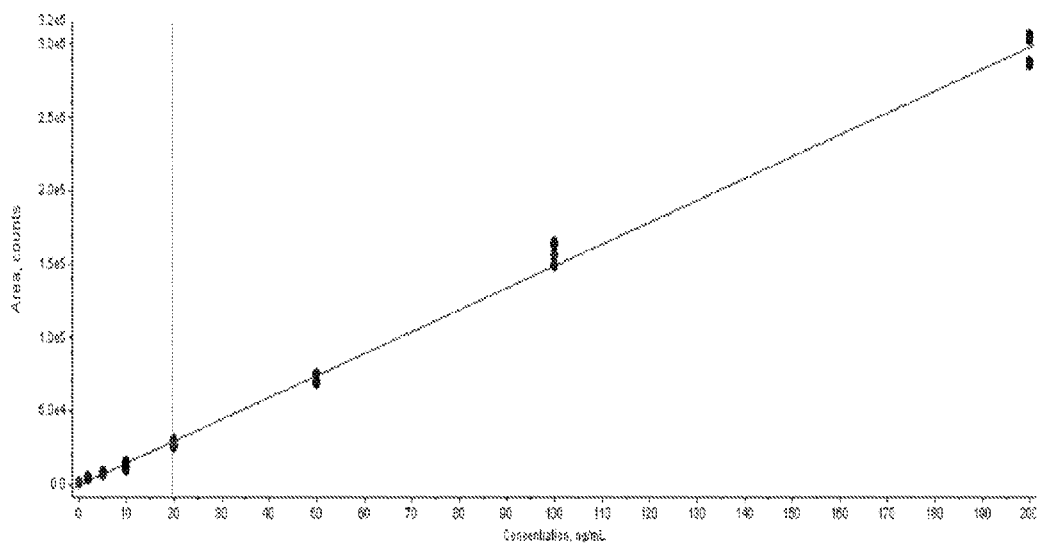
FIG. 5 show a calibration line for a peptide of SEQ ID NO. 20.
Figure 6:
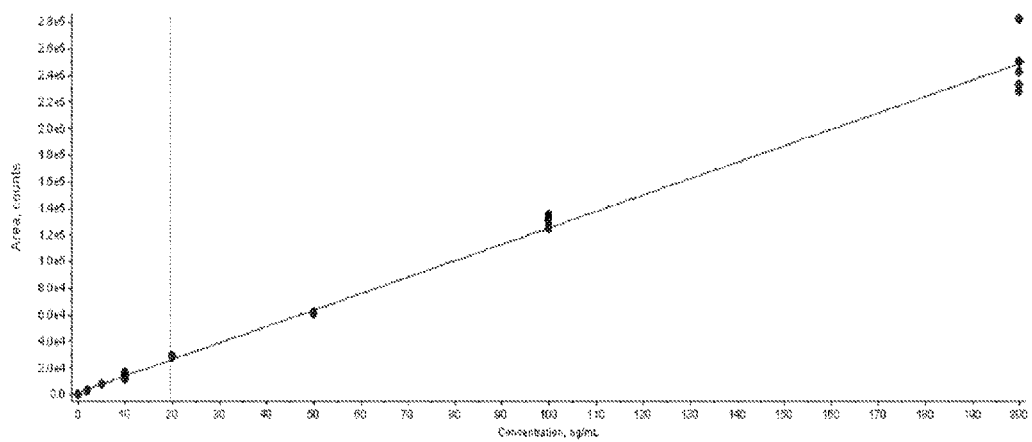
FIG. 6 show a calibration line for a peptide of SEQ ID NO. 16.
Figure 7:
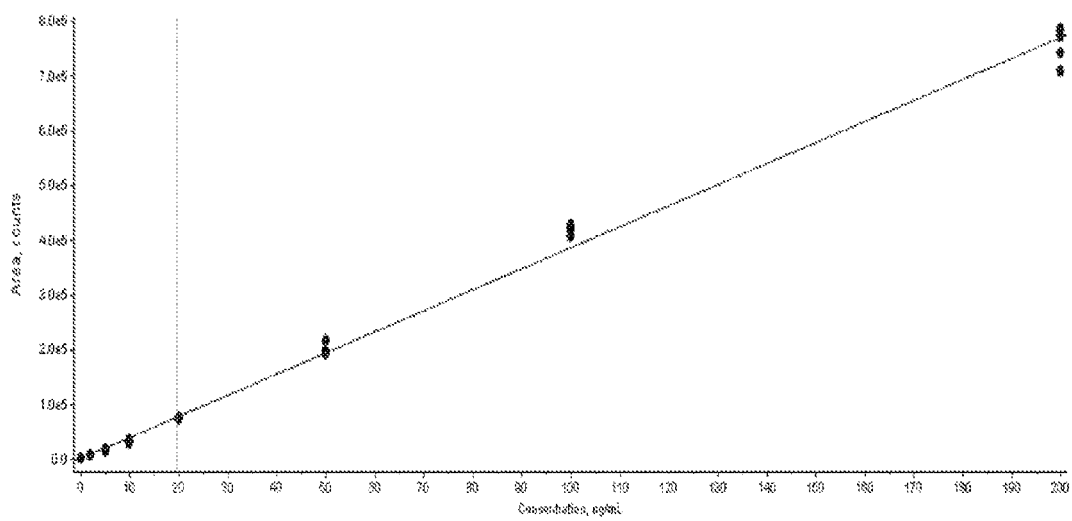
FIG. 7 show a calibration line for a peptide of SEQ ID NO. 12.
Figure 8:
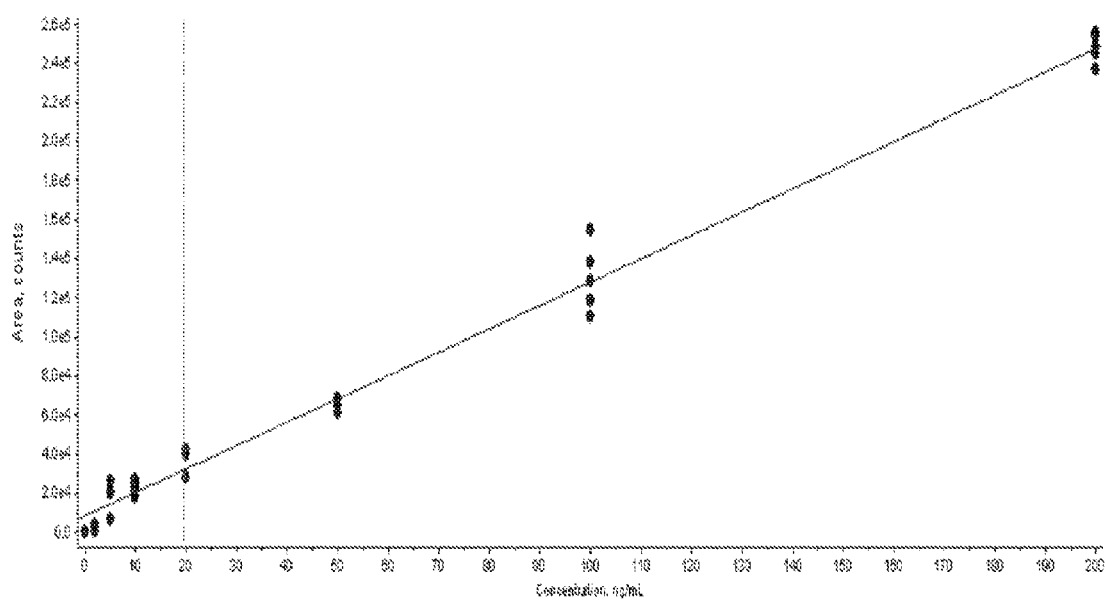
FIG. 8 show a calibration line for a peptide of SEQ ID NO. 27.
Figure 9:
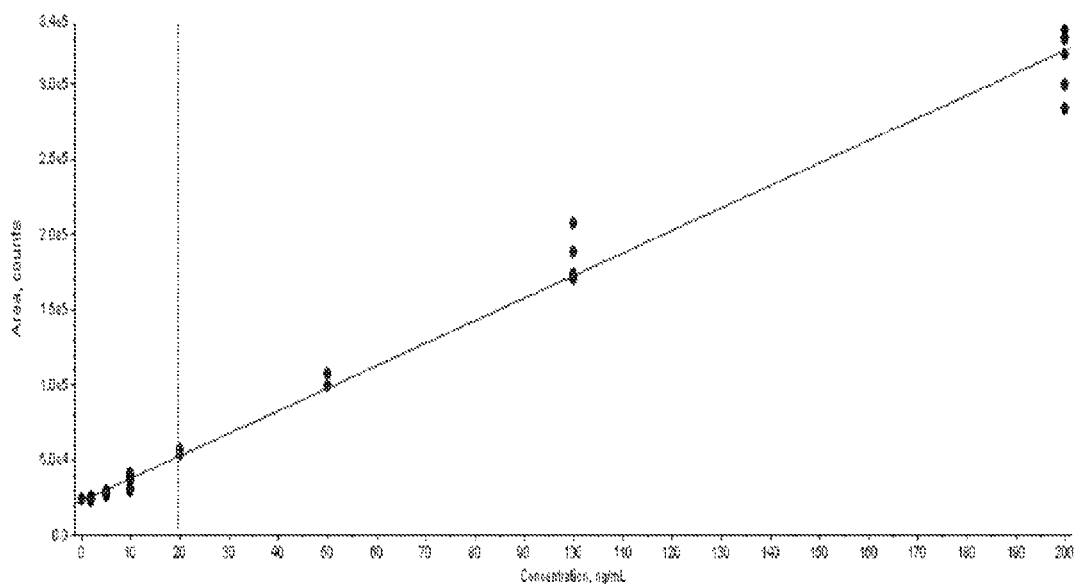
FIG. 9 show a calibration line for a peptide of SEQ ID NO. 7.

FIG. 5 depicts the calibration line for a casein peptide of SEQ ID NO. 20 when 200 ppm spiked into bread. FIG. 6 depicts the calibration line for a casein peptide of SEQ ID NO. 16 when 200 ppm is spiked into bread. FIG. 7 depicts the calibration line for a casein peptide of SEQ ID NO. 12 when 200 ppm is spiked into bread. FIG. 8 depicts the calibration line for a bovine peptide of SEQ ID NO. 27 when 200 ppm is spiked into bread. FIG. 8 depicts the calibration line for an ovalbumin peptide of SEQ ID NO. 7 when 200 ppm is spiked into bread.

Example 3

Figure 4:
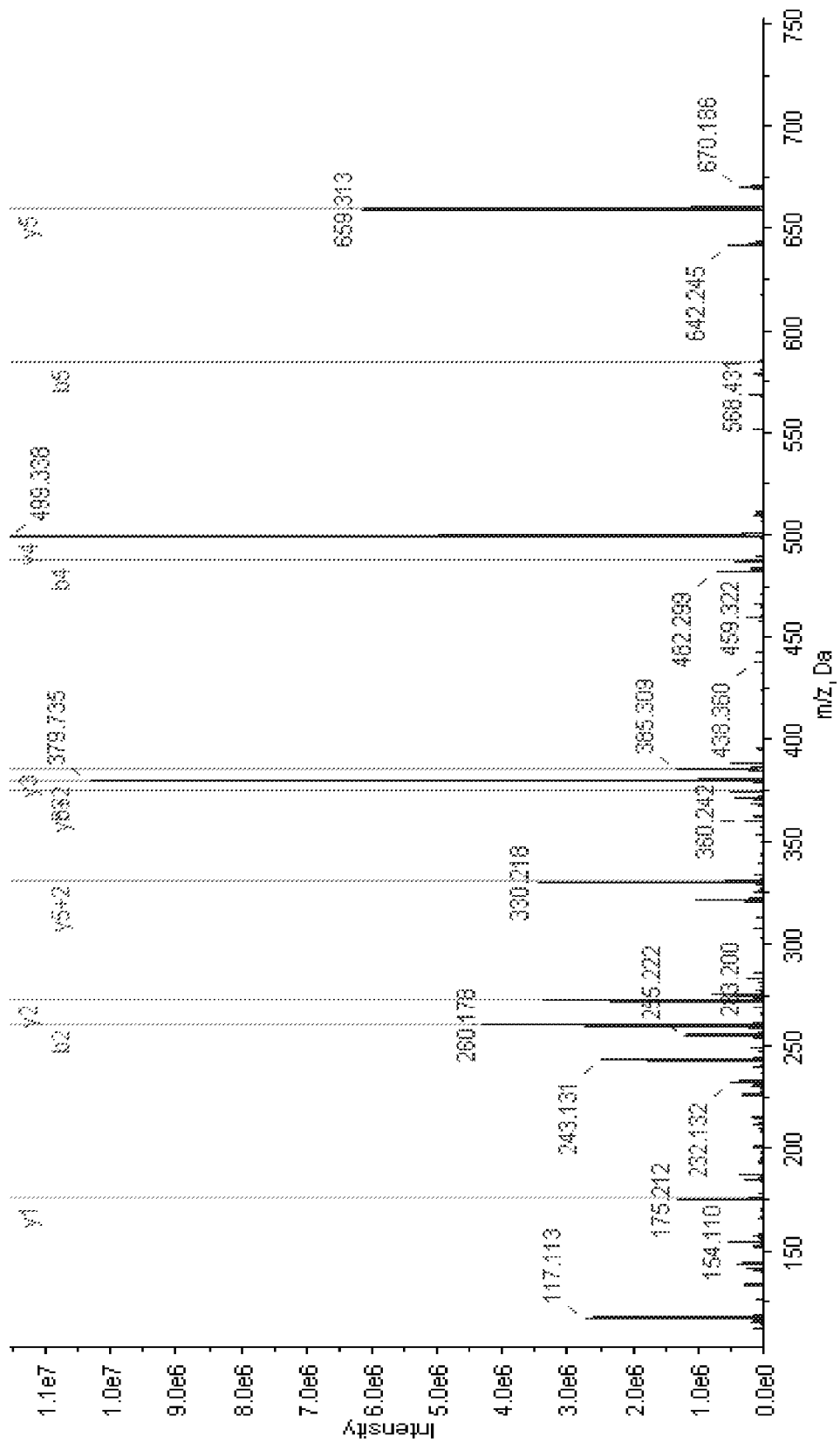
FIG. 4 shows a mass spectra of a sample containing mustard.

A package of mustard was combined with 100 mM of Tris and 2M Urea. The pH was adjusted to a pH of 9 and 9.5 using ammonium hydroxide to extract relevant proteins. The sample was subjected to similar preparation and analysis technique as described in Examples 1 or 2 with an additional process in which iodoacetamide was added to block the cysteine. The peptide sequence SEQ ID NO. 103 that had its cysteine modified with iodoacetamide was isolated and analyzed. FIG. 4 depicts a mass spectra of this sample. As is evident, the mass spectra peaks are identified at 380/499 corresponding to fragment ion at 2/y4, at 380/659 corresponding to a fragment ion at 2/y5, at 380/584 correspond to a fragment ion at 2/b5 (minor peak) and at 380/487, corresponding to a fragment ion at 2/b4.

The quantification of peptides and/or allergens of interest can utilize various calibration techniques. For example, a calibration standard containing a known amount of a selected peptide can be added to the sample prior to mass spectrometric analysis to generate a calibration curve that allows for the quantitation of samples that are subsequently run through an LC-MS/MS. In some embodiments, a known amount of the allergen(s) of interest can be added to the sample prior to preparing the sample for mass spectrometric analysis. By way of example, a known amount of one or more of ovalbumin, lysozyme, casein, lactoglobulin, high or low glutenins, wheat, rye, oats, barley, mustard, sesame and various nuts including macadamia, pistachio, brazil, walnuts, peanuts and hazelnuts can be added to the sample prior to digesting the sample with a proteolytic enzyme. By spiking the sample with a known concentration of the allergen(s) of interest, the quantitation of the allergen(s) or their specific peptides can be calibrated. In some embodiments, multiple samples spiked with various known amounts of the allergen(s) of interest can be iteratively tested to generate a calibration curve, for example, using a serial dilution or standard addition method. Calibration curves of the data resulting from the mass spectrometric analysis can be used to calculate, for example, the apparent concentration of peptides and/or allergen(s) in the "unspiked" samples. Various calibration curves and further detail regarding one embodiment of a calibration protocol are further shown in FIGS. 5 to 9 depict calibration curves for various peptides, which are hereby incorporated by reference in their entireties.

In some embodiments, the quantity of the peptide can be determined, for example, by Isotope Dilution Mass Spectrometry, wherein the prepared sample is spiked with an isotopically-enriched form of a peptide of interest. In one exemplary embodiment, the calibration standard can be "spiked" into the sample using various concentrations for different runs (e.g., serial dilution). Calibration curves of the data resulting from the mass spectrometric analysis can be used to calculate, for example, the apparent concentration of "unspiked" samples.

One skilled in the art will appreciate further features and advantages of methods and systems in accord with applicants' teachings based on the above-described embodiments. Accordingly, the applicants' disclosure is not to be limited by what has been particularly shown and described, except as indicated by the appended claims. All publications and references cited herein are expressly incorporated herein by reference in their entirety.

What is claimed is:

1. A method of detecting casein in a sample said method comprising:
   adding a proteolytic enzyme to the sample to lyse at least a portion of the casein present in the sample, into a plurality of peptides; and
   utilizing liquid chromatography tandem mass spectrometry (LC-MS/MS) to determine whether at least one peptide is in the sample
   wherein said determining whether at least one peptide is in the sample comprises monitoring at least one precursor-product ion pair transition with specified m/z value associated with a specific amino acid sequence selected from the group consisting of:
   i) SEQ ID NO: 14, m/z value of 416/488, 416/587, or 416/702; and
   ii) SEQ ID NO: 15, m/z value of 634/771, or 634/935.

2. A method of detecting lactoglobulin in a sample, said method comprising:
   adding a proteolytic enzyme to the sample to lyse at least a portion of the lactoglobulin present in the sample, into a plurality of peptides; and
   utilizing liquid chromatography tandem mass spectrometry (LC-MS/MS) to determine whether at least one peptide is in the sample, wherein
   said determining whether at least one peptide is in the sample comprises monitoring at least one precursor-product ion pair transition with specified m/z value associated with a specific amino acid sequence SEQ ID NO: 27, m/z value of 623/573, 623/918, 623/819, or 623/1047.

3. The method of claim 1, wherein the proteolytic enzyme comprises trypsin.

4. The method of claim 1, wherein said determining comprises quantifying an amount of said at least one peptide in the sample, utilizing at least one isotopically-enriched peptide having the same amino acid sequence as that of said at least one peptide to calibrate the quantitation of said at least one peptide, and utilizing a standard comprising a known concentration of said at least one peptide to calibrate the quantitation of said at least one peptide.

5. The method of claim 2, wherein the proteolytic enzyme comprises trypsin.

6. The method of claim 2, wherein said determining comprises:
   quantifying an amount of at least one peptide in the sample,
   utilizing at least one isotopically-enriched peptide having the same amino acid sequence as that of said at least one peptide to calibrate the quantitation of said at least one peptide, and
   utilizing a standard comprising a known concentration of said at least one peptide to calibrate the quantitation of said at least one peptide.

\* \* \* \* \*